United States Patent
Howell et al.

(10) Patent No.: US 9,844,568 B2
(45) Date of Patent: Dec. 19, 2017

(54) POROUS CARBON PARTICLES FOR USE IN THE TREATMENT OR PREVENTION OF LIVER DISEASE

(71) Applicants: UCL Business PLC, London (GB); University of Brighton, Brighton, Sussex (GB)

(72) Inventors: Carol Angela Howell, Littlehampton (GN); Sergey Victorovich Mikhalovsky, Saltdean (GB); Susan Rachel Sandeman, Brighton (GB); Rajiv Jalan, London (GB); Jane MacNaughtan, London (GB)

(73) Assignees: UCL Business PLC, London (GB); University of Brighton, Brighton, Sussex (GB)

( * ) Notice: Subject to any disclaimer, the term of this patent is extended or adjusted under 35 U.S.C. 154(b) by 268 days.

(21) Appl. No.: 14/385,332

(22) PCT Filed: Mar. 15, 2013

(86) PCT No.: PCT/GB2013/050673
§ 371 (c)(1),
(2) Date: Sep. 15, 2014

(87) PCT Pub. No.: WO2013/136094
PCT Pub. Date: Sep. 19, 2013

(65) Prior Publication Data
US 2015/0064256 A1   Mar. 5, 2015

(30) Foreign Application Priority Data
Mar. 16, 2012 (GB) .................................. 1204696.7

(51) Int. Cl.
*A61K 9/14* (2006.01)
*A61K 33/44* (2006.01)
*A61K 9/00* (2006.01)
*A61K 9/16* (2006.01)

(52) U.S. Cl.
CPC ............ *A61K 33/44* (2013.01); *A61K 9/0053* (2013.01); *A61K 9/14* (2013.01); *A61K 9/1688* (2013.01); *Y10T 428/2982* (2015.01)

(58) Field of Classification Search
None
See application file for complete search history.

(56) References Cited

U.S. PATENT DOCUMENTS

| | | | |
|---|---|---|---|
| 4,681,764 | A | 7/1987 | Endo et al. |
| 7,651,974 | B2 | 1/2010 | Sonobe et al. |
| 8,357,366 | B2 | 1/2013 | Sonobe et al. |
| 8,440,228 | B2 | 5/2013 | Sonobe et al. |
| 2007/0141046 | A1 | 6/2007 | Von Blucher et al. |
| 2008/0025907 | A1 | 1/2008 | Tennison et al. |
| 2010/0086469 | A1 | 4/2010 | Tennison et al. |
| 2010/0098615 | A1 | 4/2010 | Tennison et al. |
| 2013/0202664 | A1 | 8/2013 | Kurokawa et al. |

FOREIGN PATENT DOCUMENTS

| | | | |
|---|---|---|---|
| CN | 1942196 A | 4/2007 | |
| EP | 1525886 A1 | 4/2005 | |
| EP | 1745793 A1 | 1/2007 | |
| EP | 1407772 B9 | 2/2007 | |
| EP | 1500397 B1 | 3/2007 | |
| EP | 1249241 B1 | 6/2007 | |
| EP | 2628483 A1 | 4/2012 | |
| GB | 1560556 A | 2/1980 | |
| JP | S50-000691 A | 1/1975 | |
| JP | 551-151693 A | 12/1976 | |
| JP | S57-031864 A | 2/1982 | |
| JP | 2005-089306 A | 9/2003 | |
| JP | 2004123672 A | 4/2004 | |
| JP | 2006-111604 A | 4/2006 | |
| JP | 2007045775 A | 2/2007 | |
| JP | 2013-520467 A | 8/2013 | |
| RU | 2177319 C2 * | 12/2001 | ........... A61K 31/714 |
| WO | 0212380 A2 | 2/2002 | |
| WO | 20050094845 A1 | 10/2005 | |
| WO | WO/2007/132022 | 11/2007 | |
| WO | 2008043983 A2 | 4/2008 | |
| WO | 2010138519 A2 | 12/2010 | |
| WO | 2011070363 A1 | 6/2011 | |
| WO | 20110104275 A1 | 9/2011 | |
| WO | WO/2011/104275 | 9/2011 | |
| WO | 2012050025 A1 | 4/2012 | |

OTHER PUBLICATIONS

Liver Diseases, Retrieved [Sep. 27, 2016], Retrieved online URL:<https://medlineplus.gov/liverdiseases.html>.*
International Search Report, dated Aug. 5, 2013, of the PCT International Search Authority of PCT Application No. PCT/GB2013/050673 filed on Mar. 15, 2013 titled "Porous Carbon Particles for Use In the Treatment or Prevention on Liver Disease." Applicant: UCL Business PLC.
International Preliminary Report on Patentability and Written Opinion dated Sep. 16, 2014, issued by the Patent Cooperation Treaty in International Application No. PCT/GB2013/050673 (Applicant: UCL Business PLC) filed Mar. 15, 2013.
Keshavarzian A, Farhadi A, Forsyth CB, Rangan J, Jakate S, Shaikh M, et al. Evidence that chronic alcohol exposure promotes intestinal oxidative stress, intestinal hyperpermeability and endotoxemia prior to development of alcoholic steatohepatitis in rats. J Hepatol 2009; 50: 538-547.

(Continued)

*Primary Examiner* — Nannette Holloman
(74) *Attorney, Agent, or Firm* — Sorell, Lenna & Schmidt LLP; William D. Schmidt, Esq.

(57) ABSTRACT

The invention provides porous carbon particles for use in the treatment or prevention of liver disease, wherein at least 20% of the total pore volume is made up of pores having a mean diameter of from 2 to 200 nm and/or wherein the particles comprise micropores of diameter 2 nm or less and small macropores of diameter 50 nm to 500 nm, but substantially no mesopores of diameter greater than 2 nm and less than 50 nm, and substantially no large macropores of diameter greater than 500 nm.

28 Claims, 42 Drawing Sheets

(56) References Cited

OTHER PUBLICATIONS

Rao R. Endotoxaemia and Gut Barrier Dysfunction in Alcoholic Liver Disease. Hepatology 2009; 50:638-644.
Basuroy S, Sheth P, Mansbach CM, Rao RK. Acetaldehyde disrupts tight junctions and adherens junctions in human colonic mucosa: protection by EGF and L-glutamine. Am J Physiol Gastrointest Liver Physiol 2005; 289: G367-G375.
Stadlbauer V, Mookerjee RP, Wright GA, Davies NA, Jurgens G, Hallström S, Jalan R. Role of Toll-like receptors 2, 4, and 9 in mediating neutrophil dysfunction in alcoholic hepatitis. Am J Physiol Gastrointest Liver Physiol. Jan. 2009;296 (1):G15-22.
Stadlbauer V, Mookerjee RP, Hodges S, Wright GA, Davies NA, Jalan R. Effect of probiotic treatment on deranged neutrophil function and cytokine responses in patients with compensated alcoholic cirrhosis. J Hepatol. Jun. 2008;48(6):945-51.
Yang SQ, Lin HZ, Lane MD, Clemens M, Diehl AM.Obesity increases sensitivity to endotoxin liver injury: implications for the pathogenesis of steatohepatitis. Proc Natl Acad Sci U S A. Mar. 18, 1997;94(6):2557-62.
Cani PD, Amar J, Iglesias MA, Poggi M, Knauf C, Bastelica D, Neyrinck AM, Fava F, Tuohy KM, Chabo C, Waget A, Delmee E, Cousin B, Sulpice T, Chamontin B, Ferrieres J, Tanti JF, Gibson GR, Casteilla L, Delzenne NM, Alessi MC, Burcelin R. Metabolic endotoxemia initiates obesity and insulin resistance. Diabetes. 2007;56(7):1761-72.
Nair S, Cope K, Risby TH, Diehl AM. Obesity and female gender increase breath ethanol concentration: potential implications for the pathogenesis of nonalcoholic steatohepatitis. Am J Gastroenterol. 2001;96(4):1200-4.
Cope K, Risby T, Diehl AM. Increased gastrointestinal ethanol production in obese mice: implications for fatty liver disease pathogenesis. Gastroenterology. 2000;119(5):1340-7.
Li Z, Yang S, Lin H, Huang J, Watkins PA, Moser AB, Desimone C, Song XY, Diehl Am. Probiotics and antibodies to TNF inhibit inflammatory activity and improve nonalcoholic fatty liver disease. Hepatology. Feb. 2003;37(2):343-50.
Solga SF, Buckley G, Clark JM, Horska A, Diehl AM.The effect of a probiotic on hepatic steatosis. J Clin Gastroenterol. Nov.-Dec. 2008;42(10):1117-9.
Fernandez J, Navasa M, Planas R, Montoliu S, Monfort D, Soriano G, Vila C, Pardo A, Quintero E, Vargas V, Such J, Gines P, Arroyo V. Primary prophylaxis of spontaneous bacterial peritonitis delays hepatorenal syndrome and improves survival in cirrhosis. Gastroenterology. Sep. 2007;133(3):818-24.
Keshavarzian A, Holmes EW, Patel M, Iber F, Fields JZ, Pethkar S. Leaky gut in alcoholic cirrhosis: a possible mechanism for alcohol-induced liver damage. Am J Gastroenterol 1999; 94: 200-207.
Keshavarzian A, Farhadi A, Forsyth CB, Rangan J, Jakate S, Shaikh M, Banan A, Fields JZ. Evidence that chronic alcohol exposure promotes intestinal oxidative stress, intestinal hyperpermeability and endotoxemia prior to development of alcoholic steatohepatitis in rats. J Hepatol. 2009;50(3):538-47.
Stadlbauer V, Davies NA, Wright GA, Mookerjee RP, Jalan R. Endotoxemia during liver transplantation. Liver Transpl. Nov. 2007;13(11):1616-7.
Mookerjee RP, Stadlbauer V, Lidder S, Wright GA, Hodges SJ, Davies NA, Jalan R. Neutrophil dysfunction in alcoholic hepatitis superimposed on cirrhosis is reversible and predicts the outcome. Hepatology. Sep. 2007;46(3):831-40.
Wright G, Davies NA, Shawcross DL, Hodges SJ, Zwingmann C, Brooks HF, Mani AR, Harry D, Stadlbauer V, Zou Z, Williams R, Davies C, Moore KP, Jalan R. Endotoxemia produces coma and brain swelling in bile duct ligated rats. Hepatology. Jun. 2007;45(6):1517-26. Erratum in: Hepatology. Aug. 2007;46(2):610.
Stadlbauer V, Shah N, de Oca Arjona MM, Mookerjee RP, Jalan R. Alcohol takes the toll on immune function. Liver Int. Aug. 2010;30(7):934-6.
Bellot P, García-Pagán JC, Francés R, Abraldes JG, Navasa M, Pérez-Mateo M, Such J, Bosch J. Bacterial DNA translocation is associated with systemic circulatory abnormalities and intrahepatic endothelial dysfunction in patients with cirrhosis. Hepatology. Aug. 20, 2010. [Epub ahead of print].
Zapater P, Francés R, González-Navajas JM, de la Hoz MA, Moreu R, Pascual S, Monfort D, Montoliu S, Vila C, Escudero A, Torras X, Cirera I, Llanos L, Guarner-Argente C, Palazón JM, Carnicer F, Bellot P, Guarner C, Planas R, Solá R, Serra MA, Muñoz C, Pérez-Mateo M, Such J. Serum and ascitic fluid bacterial DNA: a new independent prognostic factor in noninfected patients with cirrhosis. Hepatology. Dec. 2008;48(6):1924-31.
Seki E, De Minicis S, Osterreicher CH, Kluwe J, Osawa Y, Brenner DA, Schwabe RF, TLR4 enhances TGF-beta signaling and hepatic fibrosis. Nat. Med. Nov. 2007;13(11):1324-32.
M. Montes de Oca; N. Shah; D. K. Dhar; M. Jover-Cobos; N. Davies; R. P. Mookerjee; R. Jalan. Treatment with TLR 4 antagonist restores the inflammatory cellular immune dysfunction in acetaminophen (APAP) induced acute liver failure (ALF) mice. Hepatology 2010; AASLD: 1084A.
J. Macnaughtan; N. Davies; V. Stadlbauer; S. W. Olde Damink; R. P. Mookerjee; R. Jalan. Evidence for compartmentalised endotoxemia and its effect on neutrophil function in the portal circulation in cirrhosis. Hepatology 2010; AASLD: 342A
N. Shah; D. K. Dhar; R. P. Mookerjee; N. Davies; R. Jalan. Gut sterilisation with Norfloxacin modulates cerebral inflammation in cirrhosis and prevents deterioration in brain oedema and delays coma in cirrhotic rats. Gut 2010; 59: A24.
N. Shah; D. K. Dhar; F. Mohamed; R. P. Mookerjee; N. Davies; R. Jalan. The role of Toll like receptor-4 in the pathogenesis of Hepatorenal syndrome in a Bile duct ligated model of cirrhosis in the rat. Gut 2010; 59: A9.
M. Montes de Oca; N. Shah; D. K. Dhar; N. Davies; R. P. Mookerjee; M. Jover-Cobos; A. Habtesion; R. Jalan. Evidence of Dendritic Cell dysfunction in Cirrhosis and its restoration by Toll-like Receptor 4 antagonism Gut 2010; 59: A34.
S.R Sandeman, C.A Howell, GJ Phillips, JG Davies, AW Lloyd, SV Mikhalovsky, S.R Tennison, A.P. Rawlinson, O.P. Kozynchemko. (2008) Inflammatory cytokine removal by an activated carbon device in a flowing system. Biomaterials 29:1683-1644.
Howell, CA; Sandeman, S; Webb, LS; Phillips, GJ; Mikhalovky, SV; Tennison, S; Rawlinson, AP; Kozynchenko. (2008) Cytokine and superantigen adsorption by novel, activated carbon beads. International journal of artificial organs. 31,7 656.
Lukichev BG, Shostka GD, Strelko VV, Azizova TS, Kavraĭskiĭ IuR, Panina Ilu. Ter Arkh. 10-years' experience in using enterosorption for treating chronic kidney failure. 1992;64(8):52-6.
Ryss ES, Riabov SI, Lutoshkin MB. A comparative evaluation of the efficacy of the clinical use of SKN-4M-, SKT-6A-and polifepan-type sorbents in treating patients with chronic kidney failure (clinical and experimental studies). Ter Arkh. 1996;68(8):39-43.
Ryss ES, Lutoshkin MB. The effect of enterosorbents on stomach functional activity and the parameters of nitrogen metabolism in patients with nephrogenous gastropathies Ter Arkh. 1991;63(7):112-6.
Nykula TD, Bondur VV, Pluzhnyk KH. Lik Sprava. The effect of the SKN charcoal enterosorbent on the clinico-laboratory indices of patients with chronic circulatory failure. Lik Sprava. Jul.-Sep. 1996;(7-9):106-9.
Sledzevskaia IK, Bul'da VI, Babov KD. Enterosorbent SKN in the combined rehabilitative treatment of patients who have had a myocardial infarct. Vrach Delo. Sep. 1991;(9):87-9.
Riabov SI, Tsiura VI, Lukichev BG, Shostka GD, Natochin IuV. Reduced experimental blood creatinine as affected by the SKN enterosorbent. Urol Nefrol (Mosk). Mar.-Apr. 1987;(2):49-52.
Davydov VI, Stavitskaia SS, Galinskaia VI, Gerasimenko NV, Strelko VV. The possibility of using carbon enterosorbents for normalizing cholesterol metabolism. Biokhimiia. Feb. 1994;59(2):304-12.
Hnatiuk MS, Soroka NIeFiziol Zh. The effect of enterosorption on the local immune processes in a toxic lesion of the large intestine. Fiziol Zh.1999;45(5):85-90.

(56) References Cited

OTHER PUBLICATIONS

Dedenko IK. The efficacy of enterosorption in an intensive contamination by radionuclides Lik Sprava Jan.-Feb. 1996; (1-2):11-5.

Neimark AI, Iakovets IaV. Changes in the hemostatic system indices of patients with chronic kidney failure under the influence of enterosorption and plasmapheresis. Ter Arkh 1994; 66(8):57-60.

Nedeliaeva AV, Levin Gla, Sosin Elu. The effect of enterosorption on the severity of endogenous intoxication in burns. Klin Khir 1994; (9):36-8.

Andreĭchyn MA, Ivakhiv OL. Enterosorption in the combined treatment of patients with salmonellosis. Lik Sprava Aug. 1992;(8):81-4.

Tarakhovskiĭ ML, Tsypkun AG, Sergeev VP, Zadorozhnaia TD, Tishchenko VK, Litvinov VF. Efficiency of enterosorbents and detoxication mechanisms in immature rats with simulated hepatitis. Fiziol Zh Nov.-Dec. 1991; 37(6):48-55.

Donish RM, Mansur O, Kirienko DV. The tolerance of diabetic patients for physical loading before and after enterosorption treatment.Vrach Delo Jul. 1991; (7):63-5.

Grin'ko IV, Krivchik AA, Ivankova OV. Functional state of the liver during development of extrahepatic cholestasis and during use of enterosorption.Vopr Med Khim May-Jun. 1991; 37(3):26-8.

Nikolaev VG. Peroral application of synthetic activated charcoal in USSR. Biomater Artif Cells Artif Organs. 1990. 18(4):555-68.

Nikolaev VG. Enterosorption. Proceedings of the fifth international symposium on hemoperfusion and artificial organs. Nov. 20-22, 1983, Tianjin, China. p. 87-99. Chief Ed Thomas Ming Swi Change, He Bing-Lin. China Academic Publishers.

Bobkova LP, Beĭko VA, Grishilo PV, Shevchuk AV, Glinskiĭ VV, Mikhalovskiĭ SV, Strelko VV, Berezhnaia NM. Enterosorption in the treatment of patients with chronic urticaria. Vrach Delo. Jul. 1990;(7):87-90.

Murayskaya GV, Nikolaev VG, Sergeev VP, Krutilina NI, Bonatskaya LV, Klevtsov VN, Surovikina VV, Sinajko VV. Enterosorption in oncotherapy. Biomater Artif Cells Immobilization Biotechnol. 1991;19(1):167-74.Research Institute of Oncology and Medical Radiology, Byelorussian SSR, Minsk,USSR.

Nikolaev VG, Sarnatskaya VV, Sigal VL, Klevtsov VN, Makhorin KE, Yushko LA. High- porosity activated carbons for bilirubin removal.Int J Artif Organs. Mar. 1991;14(3):179-85.Kavetsky Institute for Oncology, Academy of Sciences of the Ukrainian SSR, Kiev.

Huang, et al. Formation of Mesoporous Carbon With a Face-Centered-Cubic Fd3⁻ m Structure and Bimodal Architectural Pores From the Reverse Amphiphilic TriblockCopolyme r PPO-PEO-PPO. Angew. Chem. Int. Ed. 2007, 46, 1089-1093.

Malik, et al. Preparation of novel mesoporous carbons for the adsorption of an inflammatory cytokine (IL-1b). Biomaterials 25 (2004) 2933-2940.

Biomacromolecules, Aug. 15, 2011, vol. 12, p. 3733-3740. (dx.doi.org/10.1021/bm200982g).

Carbon, 2006, vol. 44, pp. 1258-1262. (doi:10.1016/j.carbon.2005.10.038).

* cited by examiner

A

B

A

B

Sham

BDL

BDL+Carbon

*P<0.05 compared to sham

*P<0.05 compared to sham

ObOb=889+280
ObOb+C=408+42

| Ob- heterozygote untreated | Ob- heterozygote + carbon |
|---|---|
|  |  |
| Ob-/Ob- untreated | Ob-Ob- + carbon |
|  |  |

HMCD untreated

HMCD + carbon

Sham

HMCD untreated

HMCD + carbon

Mean ALT (IU/ml)

MCD=314+39
MCD+C=120+29

MCD untreated

MCD + carbon

MCD untreated

MCD + carbon

POROUS CARBON PARTICLES FOR USE IN THE TREATMENT OR PREVENTION OF LIVER DISEASE

FIELD OF THE INVENTION

The invention relates to the treatment or prevention of liver disease using porous carbon particles comprising micropores of diameter 2 nm or less and meso pores/small macropores of diameter 30 nm to 500 nm, but substantially no mesopores of diameter greater than 2 nm and less than 30 nm, and substantially no large macropores of diameter greater than 500 nm. Also disclosed herein is the treatment or prevention of liver disease using porous carbon particles wherein at least 20% of the total pore volume is made up of pores having a mean diameter of from 2 to 200 nm. The invention also relates to methods for the treatment or prevention of liver disease, using such porous carbon particles.

BACKGROUND TO THE INVENTION

In the United States alone it is estimated that 60,000 people die each year of liver failure, whereas the donor pool remains constant at approximately 4000 with 16-18,000 on the waiting list. The odds of receiving a donor liver for subjects waiting on the list are only 1 in 8, yet there is no effective treatment or prevention available to extend the lifetime of this group of patients.

Liver failure results in multiple organ dysfunction and mortality rates are in the order of 80%. Bacterial-derived toxin and toxic metabolites such as acetaldehyde play key roles in disease pathogenesis. For example, gut-derived endotoxaemia and bacterial translocation play a central role in the pathogenesis of cirrhosis and its complications. However therapeutic options to target these factors are currently limited to long-term antibiotics with the attendant problem of infection with resistant organisms.

Orally administered adsorbent porous carbon particles have been used for centuries for the treatment or prevention of various disorders without any major side effects. Activated carbons are widely used to treat poisoning. A microporous carbon, AST-120 (available under the trade name KREMEZIN® from Kureha Corp., Japan) is used to treat patients with renal failure. However clinical trials evaluating the efficacy of AST-120 in the management of hepatic encephalopathy have proven negative.

SUMMARY OF THE INVENTION

The invention relates to the treatment or prevention of liver disease.

Accordingly the invention provides porous carbon particles for use in the treatment or prevention of liver disease wherein 20% to 90% of the total pore volume is made up of pores having a mean diameter of 2 nm or less and 75% or more of the remainder of the total pore volume is made up of pores having a mean diameter of from 30 nm to 500 nm.

The invention also provides a method of treating or preventing liver disease, comprising administering an effective amount of such porous carbon particles.

The invention also provides use of such porous carbon particles in the manufacture of a medicament for the treatment or prevention of liver disease.

[studied 4 weeks after], LPS: animals administered lipolysaccharide intraperitoneally; BDL Carbon refers to the carbon treated group).

Figure 13:
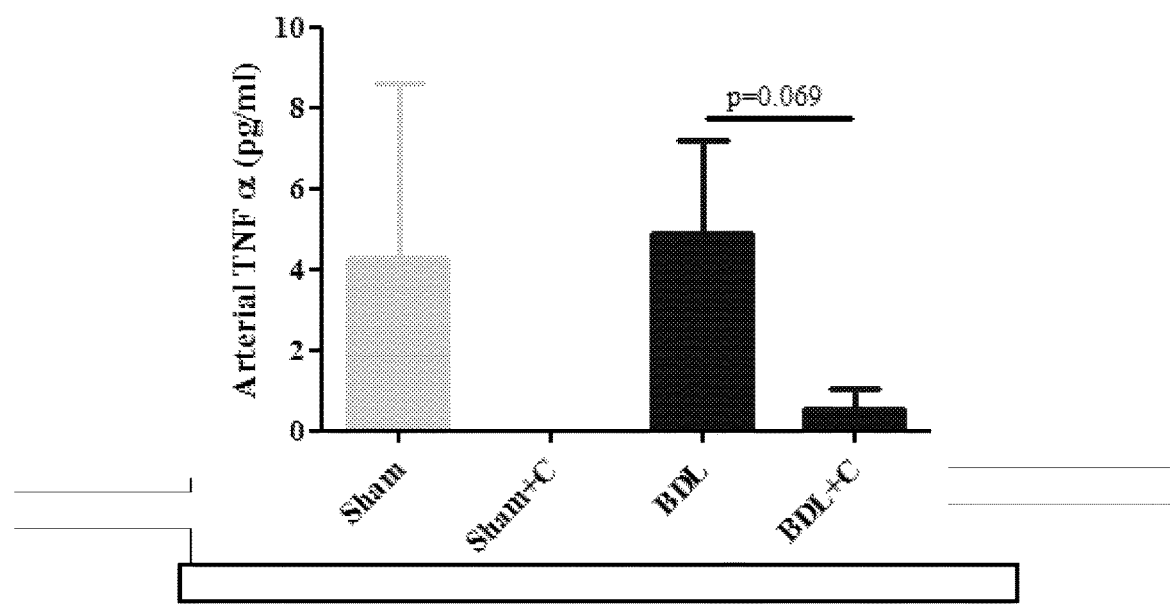

FIG. 13: Arterial TNFα. TNF alpha is significantly reduced in the Carbon treated BDL animals.

Figure 14:
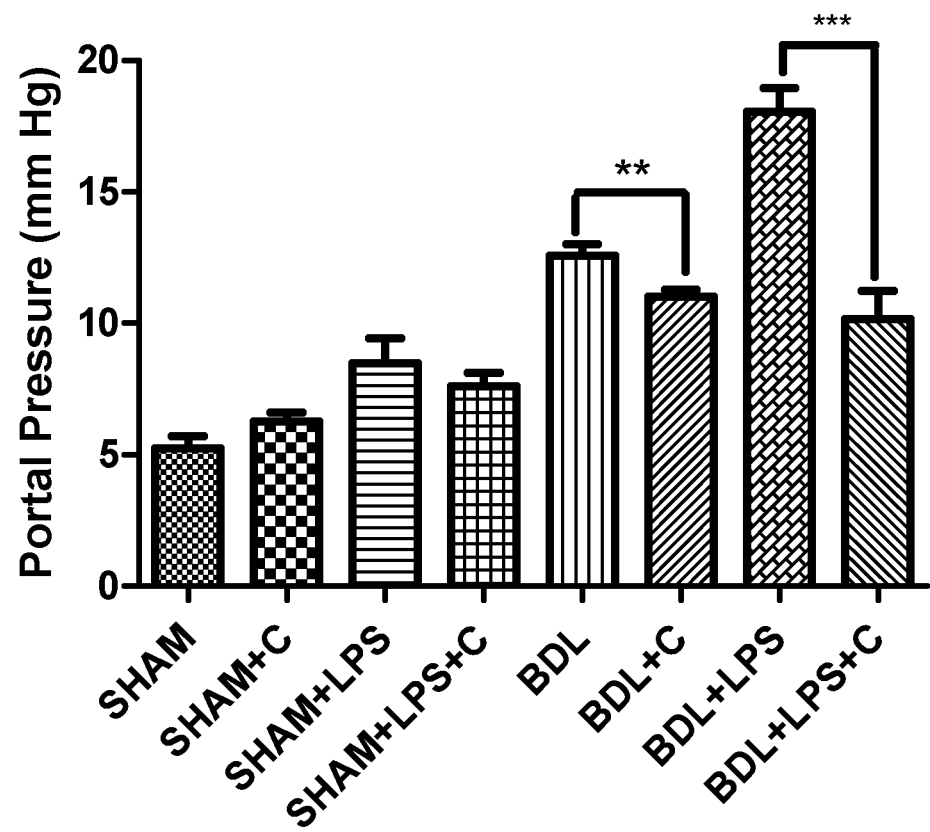

FIG. 14: Portal pressure: A significant reduction in portal pressure was observed in BDL+LPS (mean 18.05 mmHg untreated, 10.17 mmHg with carbon, p=0.0007) and BDL (mean 12.57 mmHg untreated, 11.02 mmHg with carbon, p=0.0043) groups following carbon treatment. (Sham: Sham operated, BDL: Bile-duct ligation [studied 4 weeks after], LPS: animals administered lipolysaccharide intraperitoneally; BDL Carbon refers to the carbon treated group).

Figure 15:
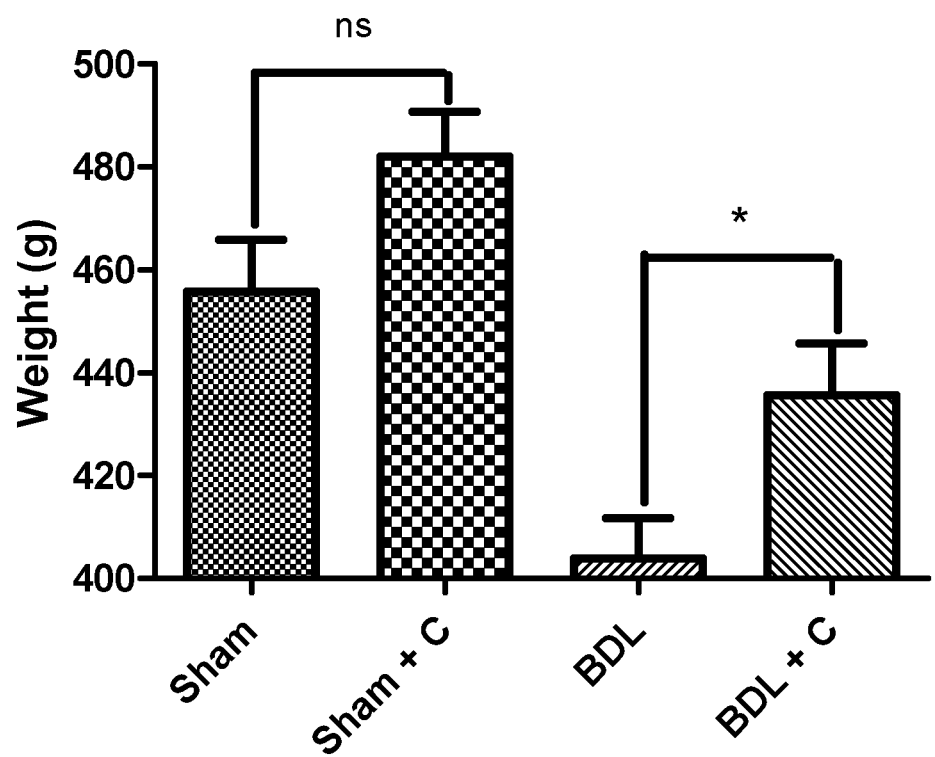

FIG. 15: Body weight. A significant increase in the dry final body weight was observed in the BDL animals treated with Carbon compared with the untreated group (p=0.0271). The data suggest that administration of carbon may reduce the cachexia associated with cirrhosis. (Sham: Sham operated, BDL: Bile-duct ligation [studied 4 weeks after], BDL Carbon refers to the carbon treated group).

Figure 16:
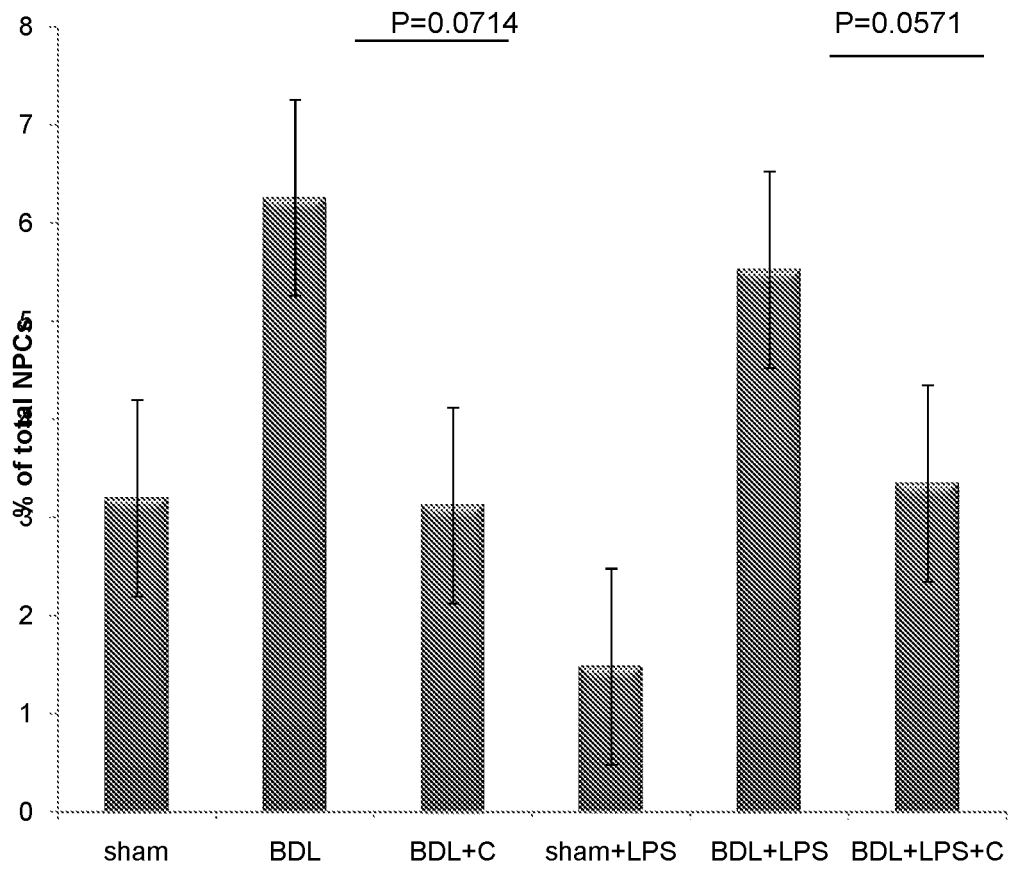

FIG. 16: Kupffer Cell (CD163+) Population. Treatment with Carbon resulted in a reduction in the activated Kupffer cell population in the BDL animals treated with Carbon compared with the untreated group. The data provide a potential mechanism of reduced liver injury seen in the BDL animals. (Sham: Sham operated, BDL: Bile-duct ligation [studied 4 weeks after], LPS: animals administered lipolysaccharide intraperitoneally; BDL Carbon refers to the carbon treated group).

Figure 17:
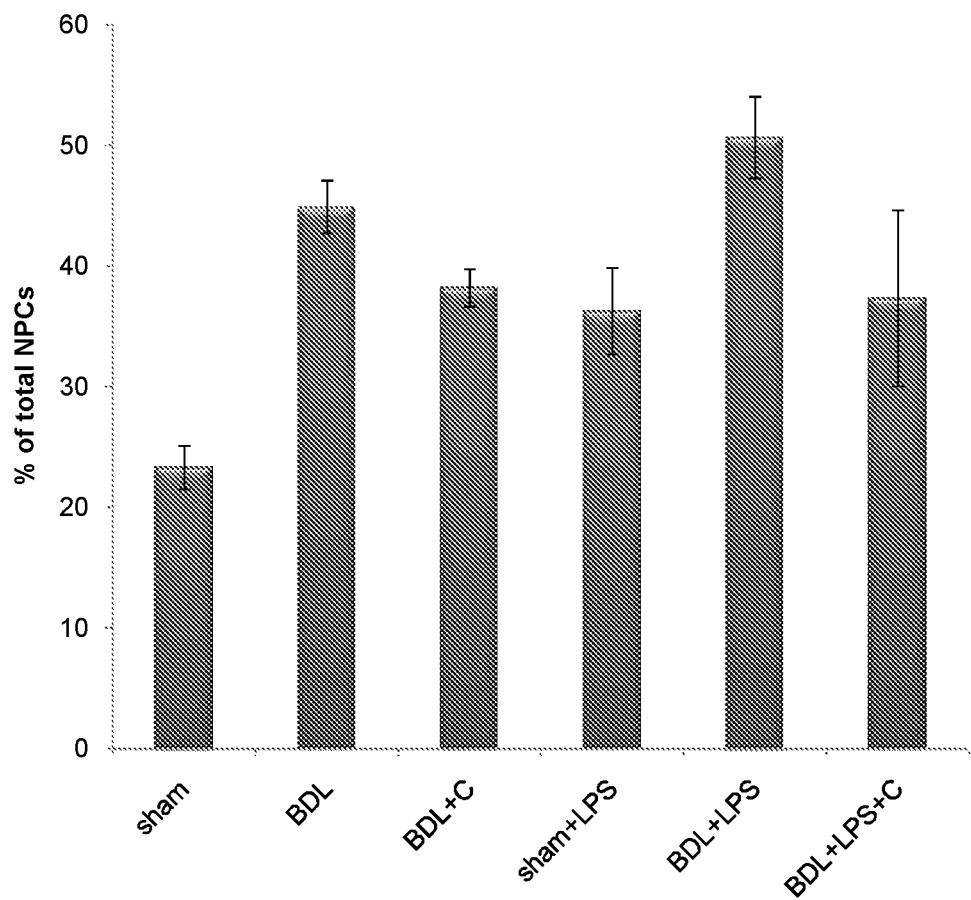

FIG. 17: Activated Macrophage (CD63+) Population. Treatment with Carbon resulted in a reduction in the activated Kupffer cell population in the BDL animals treated with Carbon compared with the untreated group. The data provide a potential mechanism of reduced liver injury seen in the BDL animals. (Sham: Sham operated, BDL: Bile-duct ligation [studied 4 weeks after], LPS: animals administered lipolysaccharide intraperitoneally; BDL Carbon refers to the carbon treated group).

Figure 18:
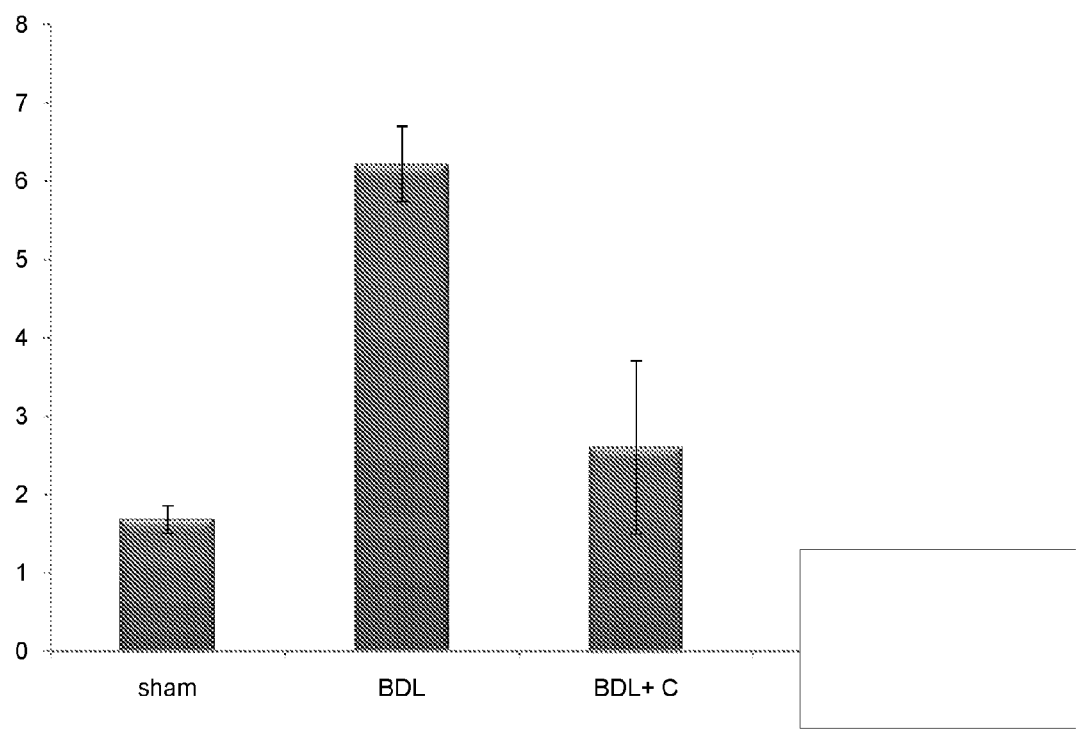

FIG. 18: Total Liver ROS Activity. Treatment with Carbon resulted in a reduction in hepatic oxidative stress in the BDL animals treated with Carbon compared with the untreated group. The data provide a potential mechanism of reduced liver injury seen in the BDL animals. (Sham: Sham operated, BDL: Bile-duct ligation [studied 4 weeks after], BDL Carbon refers to the carbon treated group).

Figure 19:
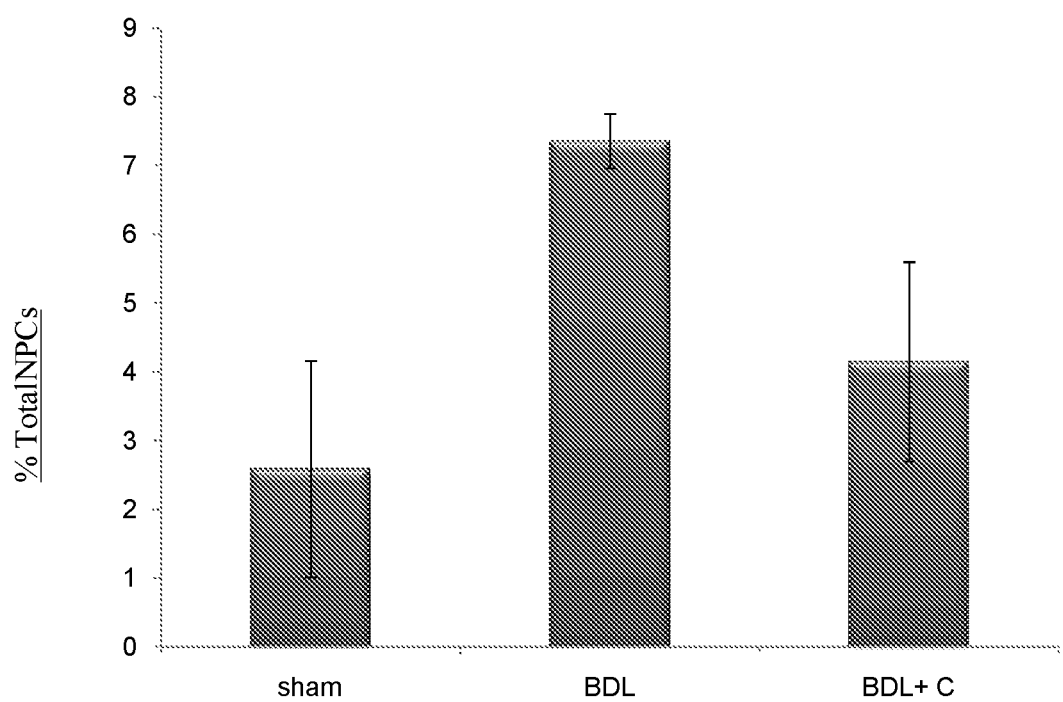

FIG. 19: Kupffer Cell ROS Activity. Treatment with Carbon resulted in a reduction in hepatic oxidative stress through modulation of the Kupffer cell production of the reactive oxygen species in the BDL animals treated with Carbon compared with the untreated group. The data provide a potential mechanism of reduced liver injury seen in the BDL animals. (Sham: Sham operated, BDL: Bile-duct ligation [studied 4 weeks after], BDL Carbon refers to the carbon treated group).

Figure 20:
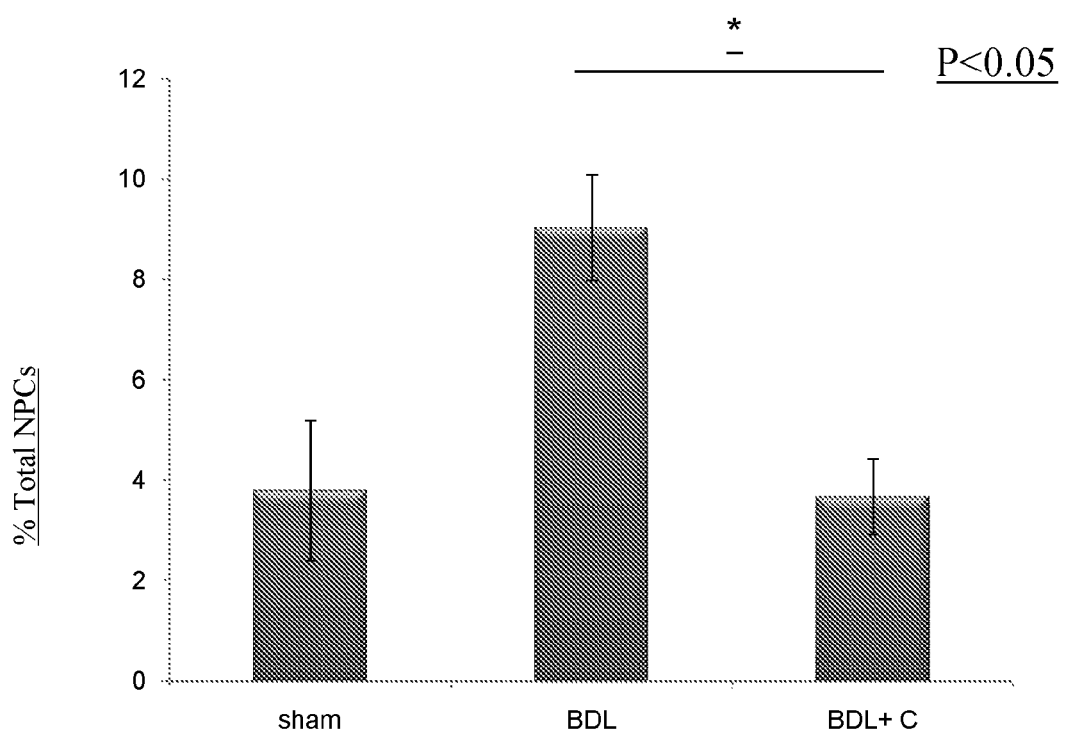

FIG. 20: Kupffer Cell LPS ROS Activity. Treatment with Carbon resulted in a reduction in endotoxin induced Kupffer cell generation of reactive oxygen species in the BDL animals treated with Carbon compared with the untreated group. The data provide a potential mechanism of reduced liver injury seen in the BDL animals. (Sham: Sham operated, BDL: Bile-duct ligation [studied 4 weeks after], LPS: animals administered lipolysaccharide intraperitoneally; BDL Carbon refers to the carbon treated group).

Figure 21:
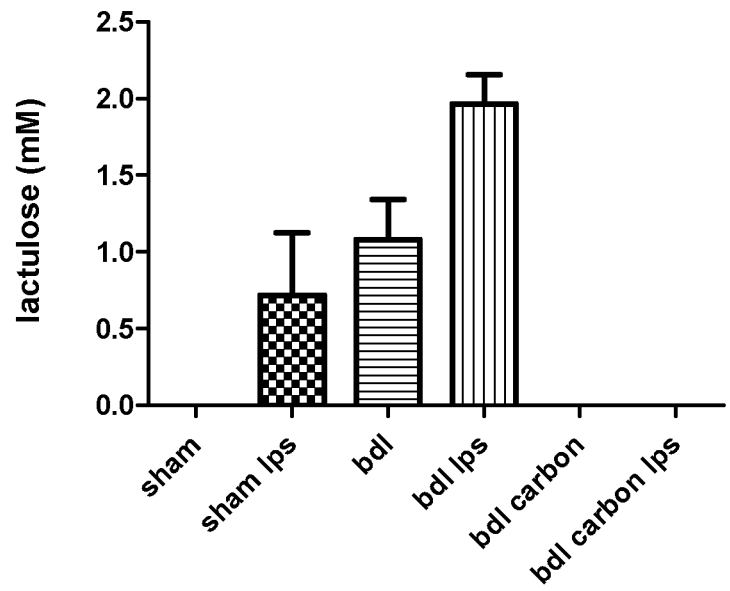
Figure 21:
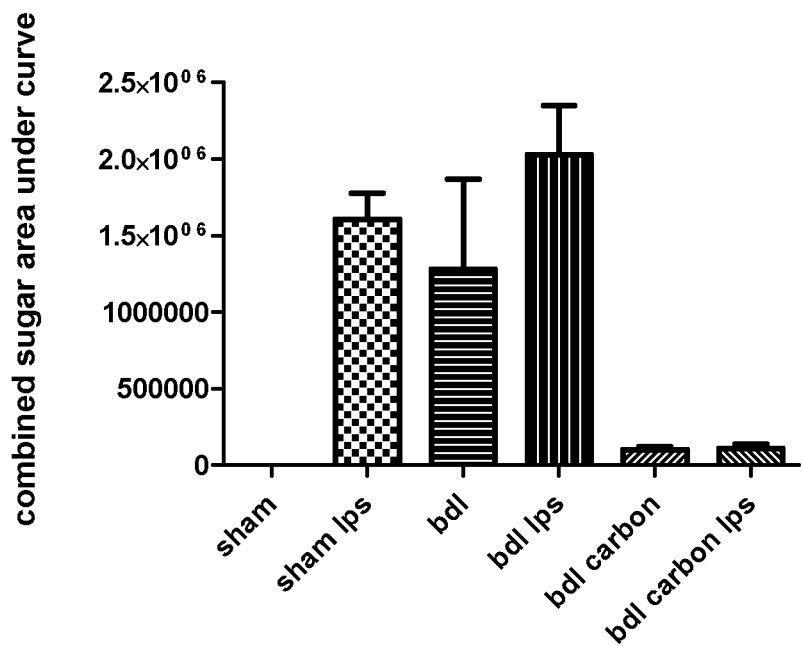

FIG. 21: Intestinal Permeability. Gut permeability was normalised in the BDL animals treated with Carbon compared with the untreated group. The data demonstrates that the carbon treated group normalized the increased permeability that was observed in the BDL animals. (Sham: Sham operated, BDL: Bile-duct ligation [studied 4 weeks after], BDL Carbon refers to the carbon treated group).

Figure 22:
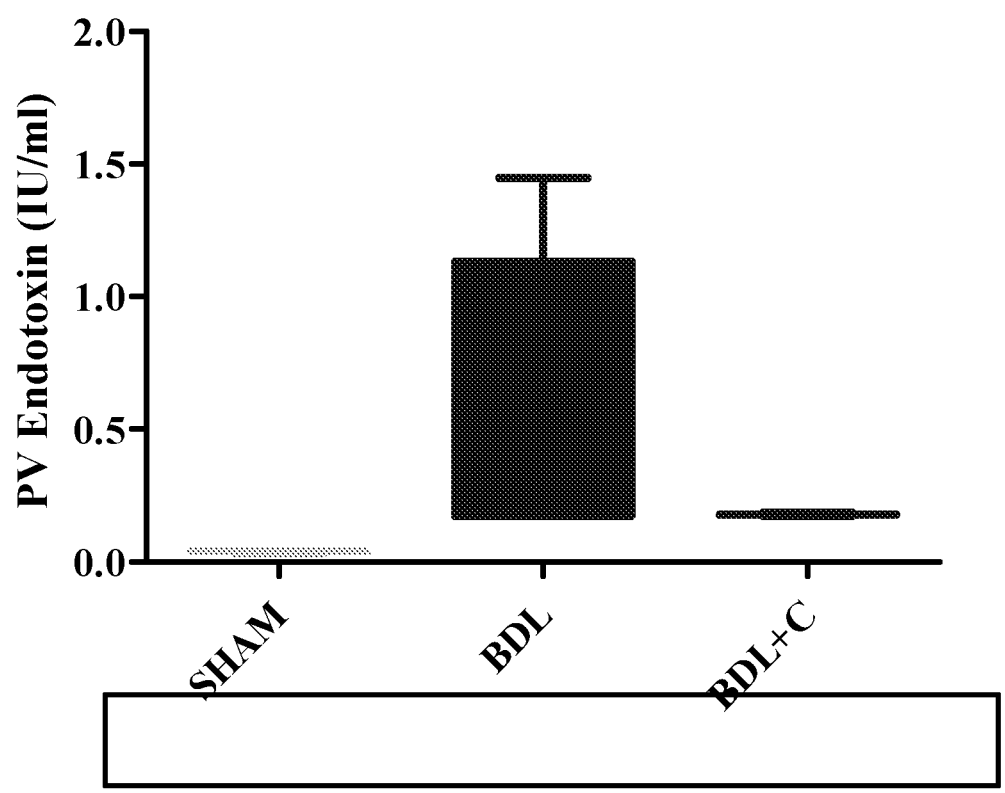

FIG. 22: Markers of Bacterial Translocation (Portal venous endotoxin). Treatment with Carbon markedly reduced endotoxemia, altered gut permeability and bacterial translocation.

Figure 23:
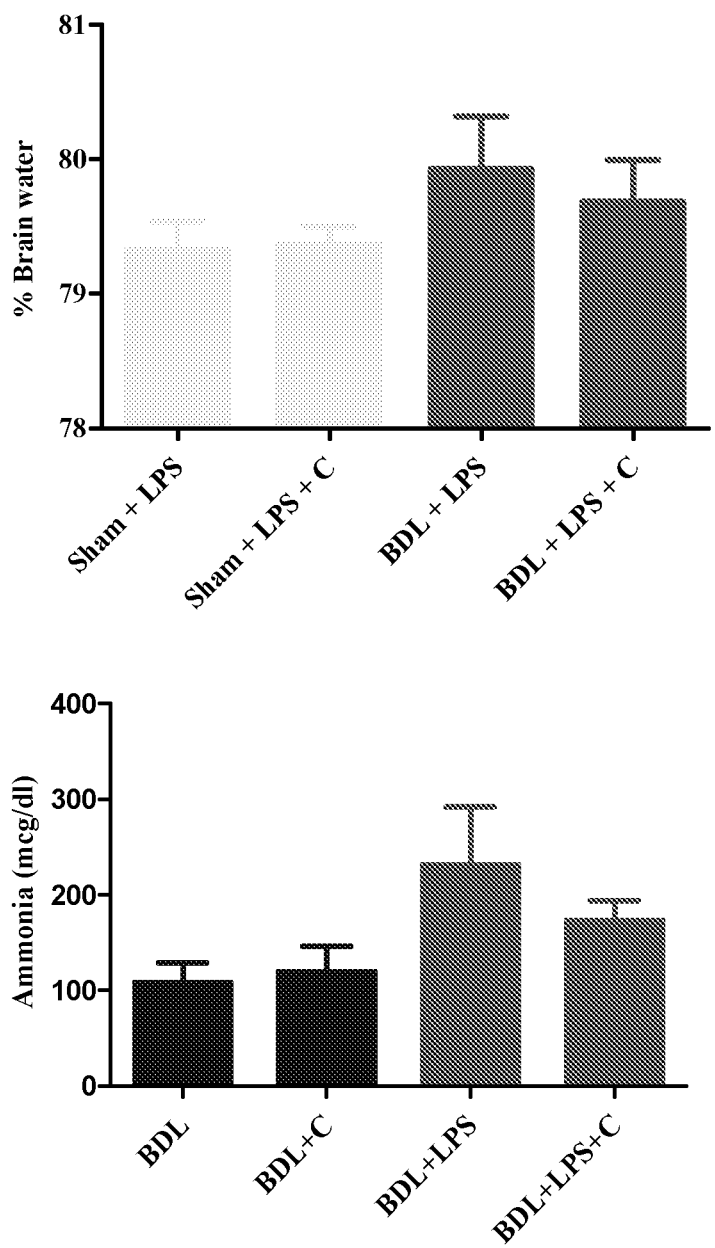

FIG. 23: Distant Organ Effects (Hepatic Encephalopathy). Treatment with carbon resulted in reduction in brain water and serum ammonia levels.

Figure 24:
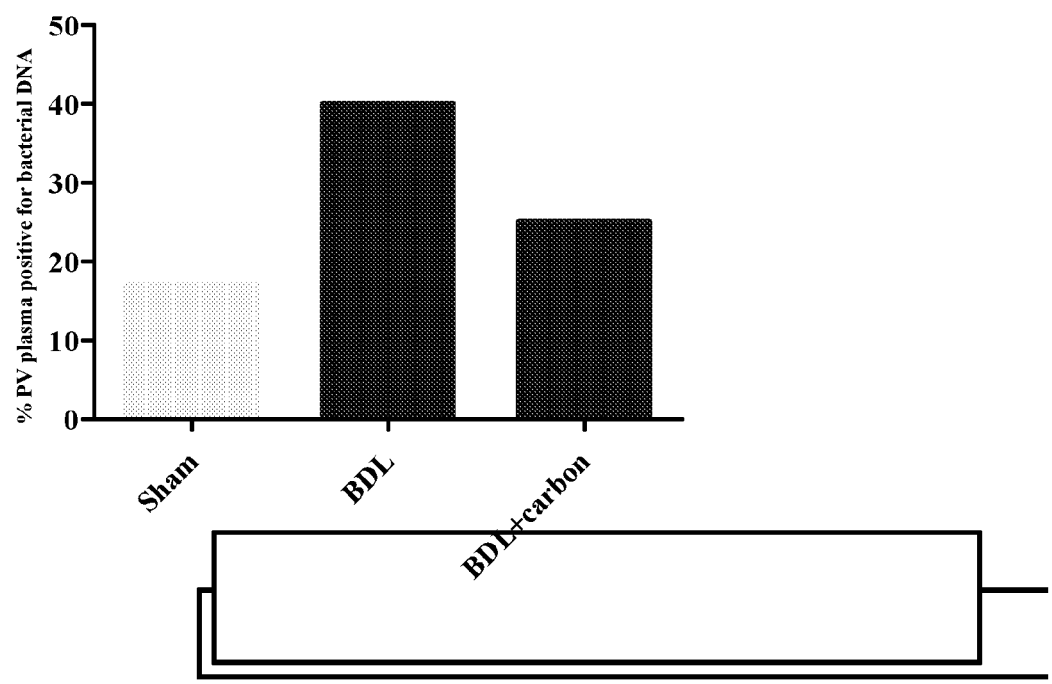

FIG. 24: Markers of Bacterial Translocation (Bacterial PCR Positivity). Treatment with Carbon resulted in a marked reduction in bacterial translocation.

Figure 25:
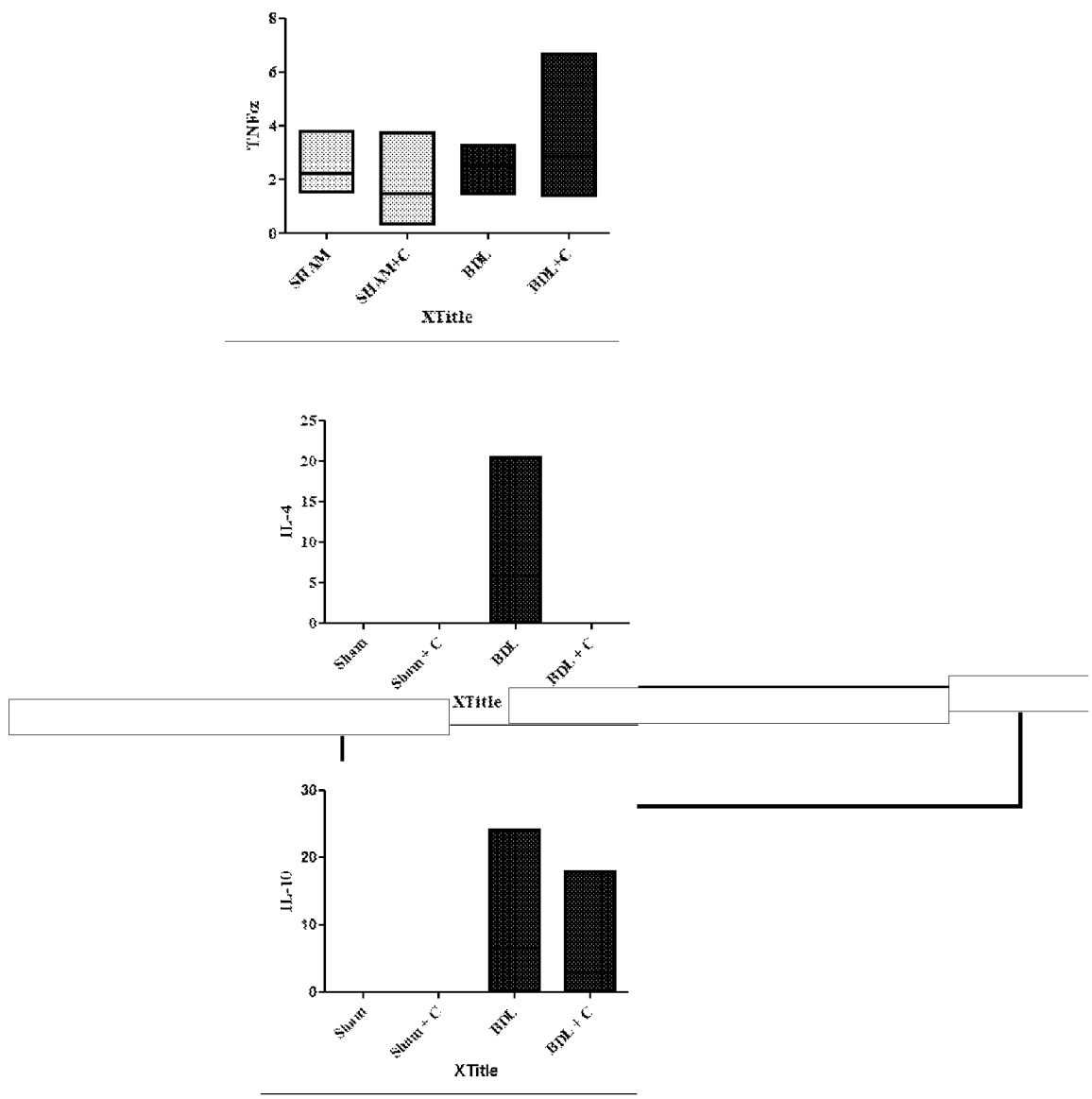

FIG. 25: Portal Venous Cytokines. A non-significant reduction in portal venous IL-4 and IL-10 was observed with carbon therapy.

Figure 26:
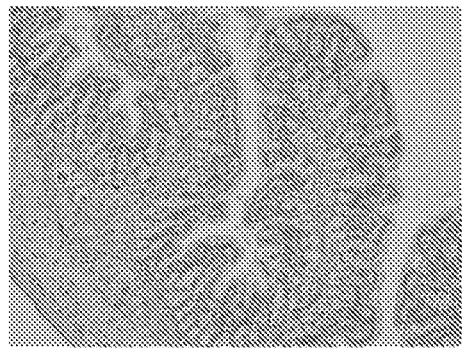
Figure 26:
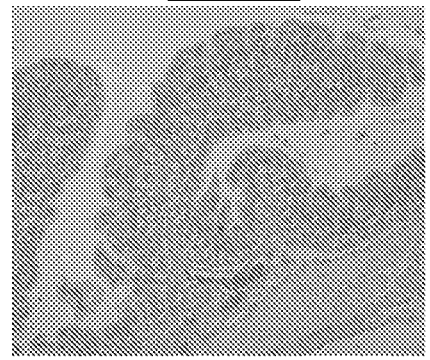
Figure 26:
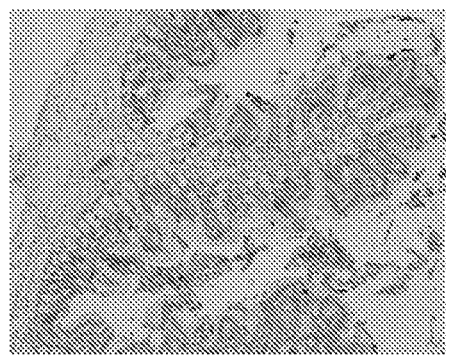

FIG. 26: Histology of Colon. Histology of the ileum, jejunum and colon remained unaffected following treatment with the Carbon showing that the treatment was safe to the intestinal mucosa. (Sham: Sham operated, BDL: Bile-duct ligation [studied 4 weeks after], BDL Carbon refers to the carbon treated group).

Figure 27:
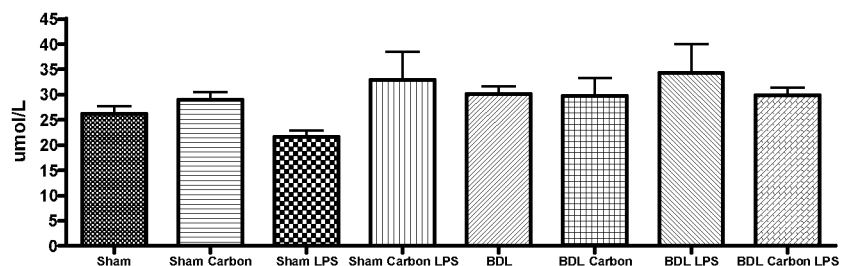

FIG. 27: Serum creatinine. The rise in serum creatinine representing renal function deteriorated in the BDL animals following administration of LPS, which was prevented in the BDL animals treated with carbon suggesting that it reduces acute kidney injury of cirrhosis. (Sham: Sham operated, BDL: Bile-duct ligation [studied 4 weeks after], LPS: animals administered lipolysaccharide intraperitoneally; BDL Carbon refers to the carbon treated group).

Figure 28:
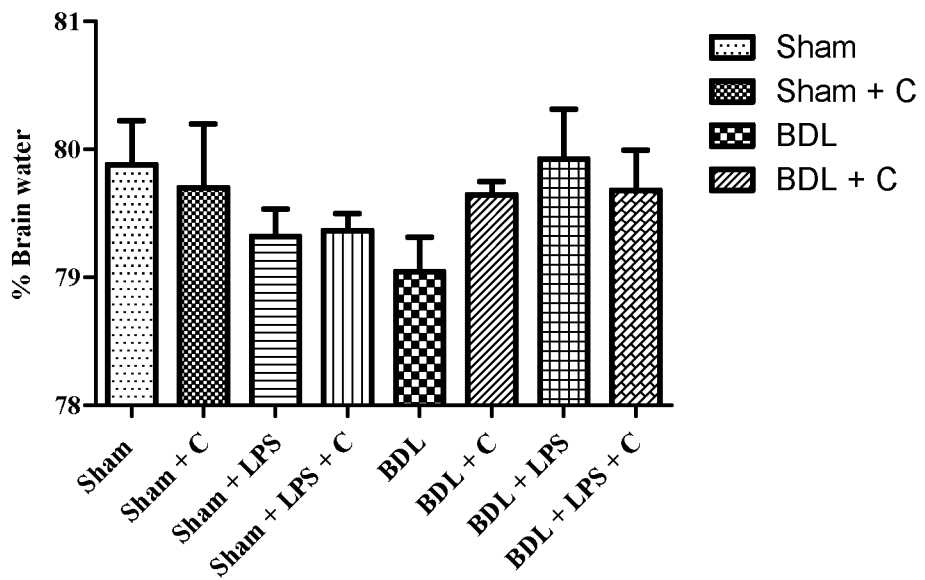

FIG. 28: Brain water (%). In the BDL animals treated with LPS brain water increased which was prevented in the animals treated with the carbons suggesting that treatment of BDL animals reduces the brain complication of cirrhosis and therefore hepatic encephalopathy. (Sham: Sham operated, BDL: Bile-duct ligation [studied 4 weeks after], LPS: animals administered lipolysaccharide intraperitoneally; BDL Carbon refers to the carbon treated group).

Figure 29:
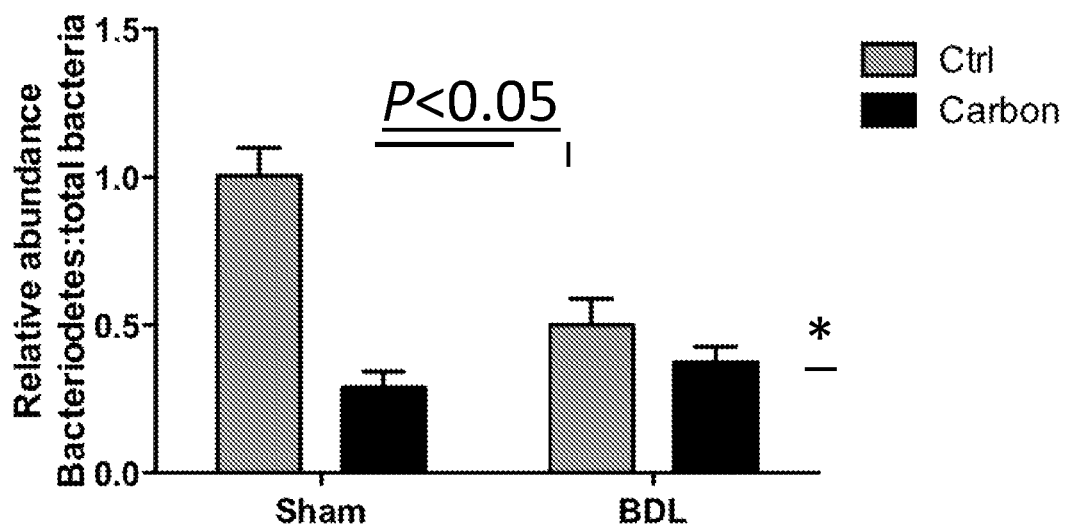

FIG. 29: *Bacteroides*/total bacteria ratio in the stool. The data suggests that the *bacteroides* species is increased in the stool of BDL animals which is reduced towards normality in the carbon treated BDL animals but the total number of bacteria remain the same. (Sham: Sham operated, BDL: Bile-duct ligation [studied 4 weeks after], BDL Carbon refers to the carbon treated group).

Figure 30:
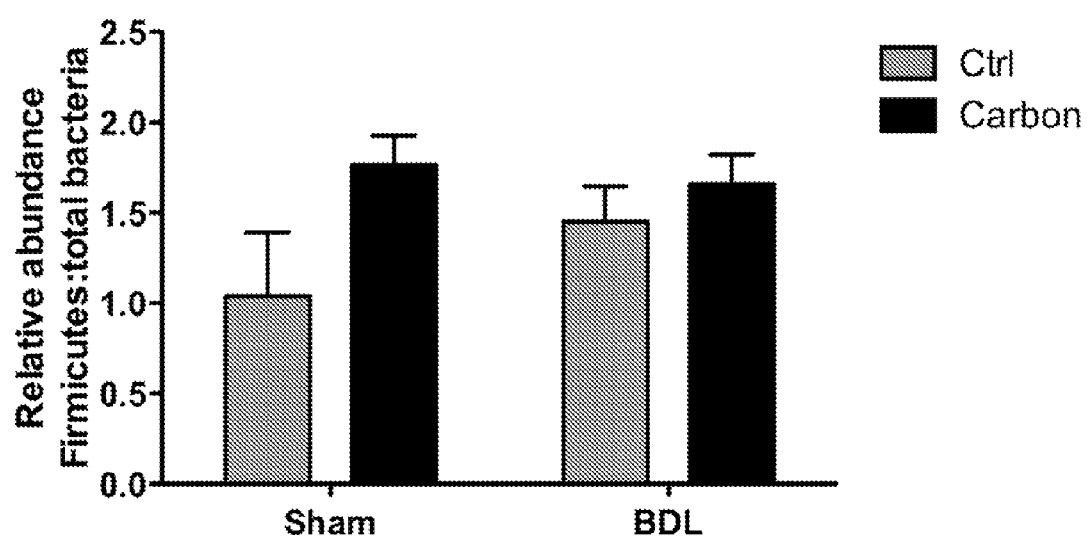

FIG. 30: Firmicutes/total bacteria ratio in the stool. The data suggests that the fermicutes species is reduced in the stool of BDL animals which is increased towards normality in the carbon treated BDL animals but the total number of bacteria remain the same. (Sham: Sham operated, BDL: Bile-duct ligation [studied 4 weeks after], BDL Carbon refers to the carbon treated group).

Figure 31:
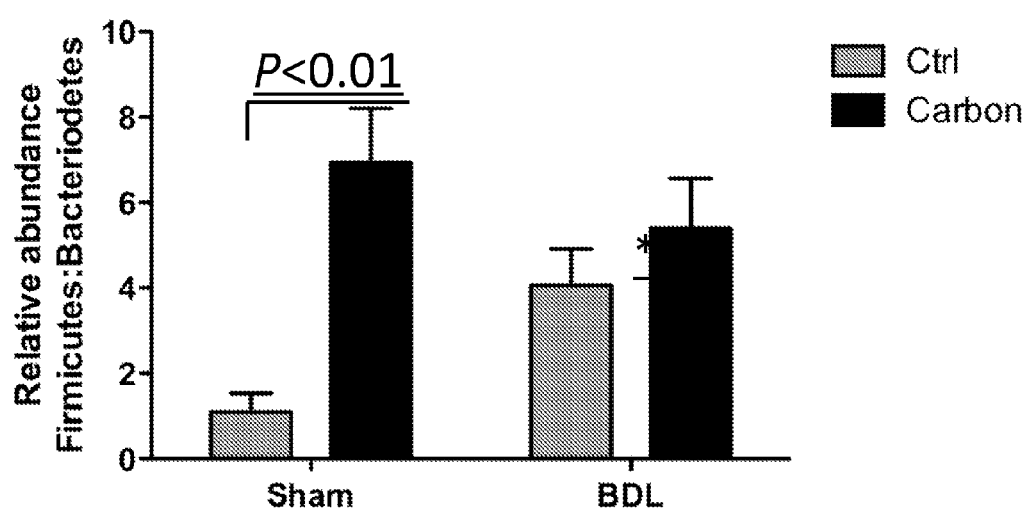

FIG. 31: Firmicutes/Bacteriodetes ratio in the stool. The data suggests that the fermicutes to *bacteroides* species ratio is reduced in the stool of BDL animals which is increased towards normality in the carbon treated BDL animals. (Sham: Sham operated, BDL: Bile-duct ligation [studied 4 weeks after], BDL Carbon refers to the carbon treated group).

Figure 32:
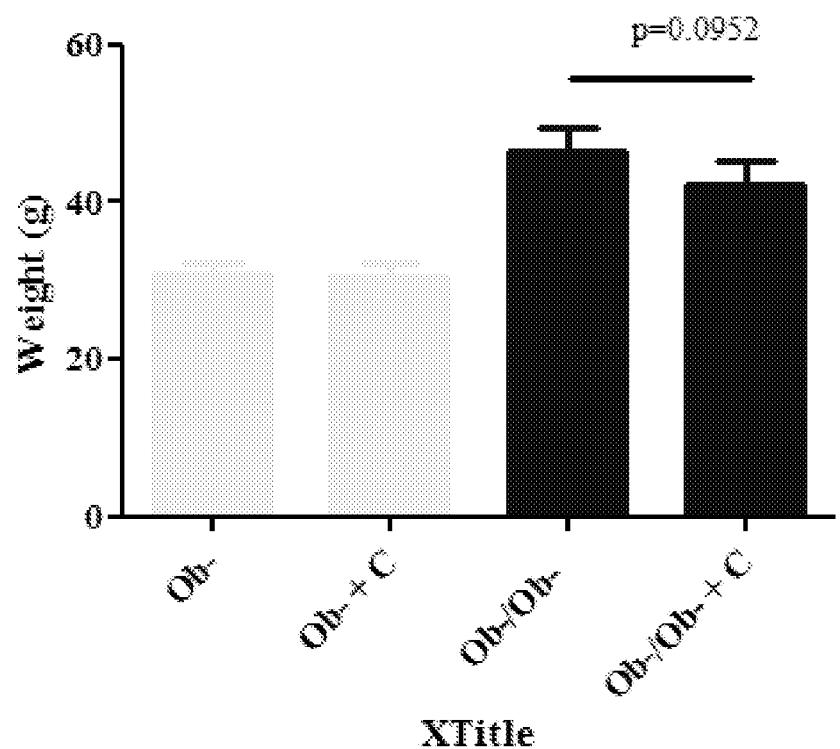

FIG. 32: Weight. Obese mice lose weight on treatment with the carbons towards normality in Leptin deficient Ob/Ob mice. The data suggest that the carbons may be a useful treatment of obesity. (Ob−: Heterozygote for the ob gene; Ob−/Ob−: Homozygote for the Ob/Ob gene; +C: groups treated with Carbon for 4 weeks).

Figure 33:
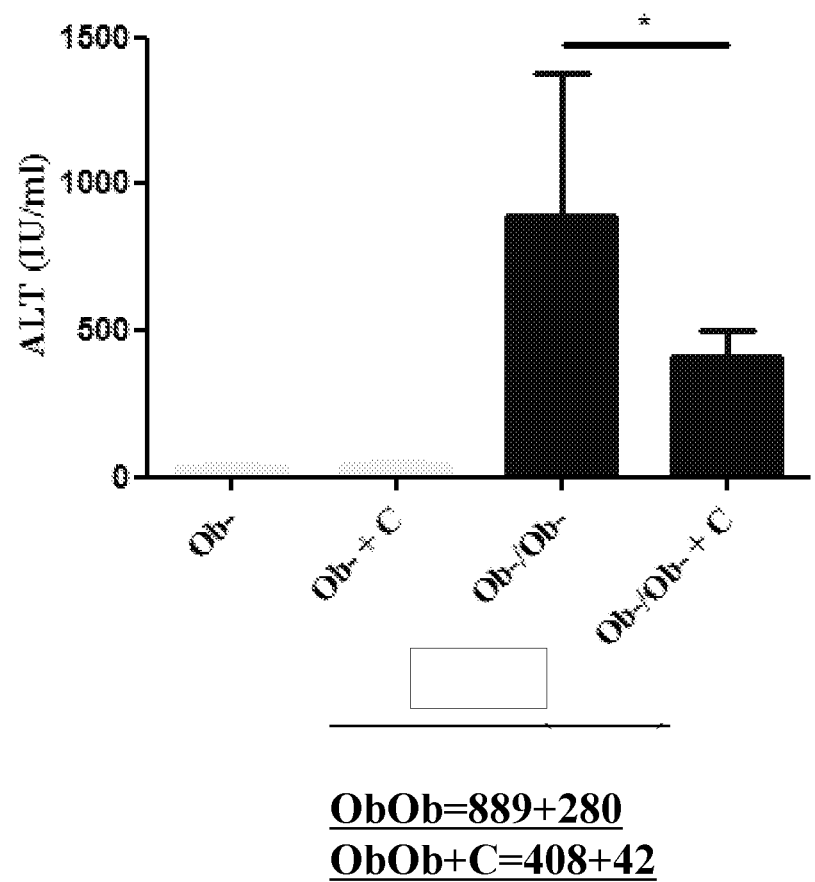

FIG. 33: ALT. Treatment of obese (Ob/Ob) mice with carbon results in a reduction in liver injury suggesting that carbon may be a treatment for non-alcoholic fatty liver disease. (Ob−: Heterozygote for the ob gene; Ob−/Ob−: Homozygote for the Ob/Ob gene; +C: groups treated with Carbon for 4 weeks).

Figure 34:
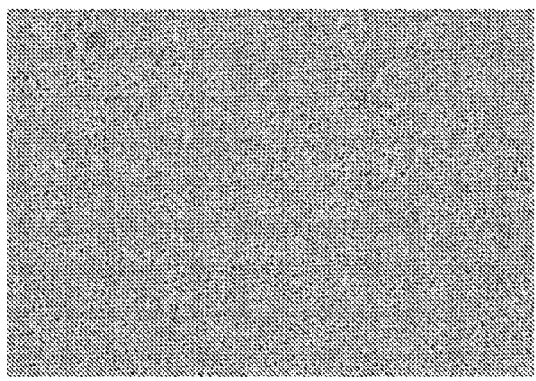
Figure 34:
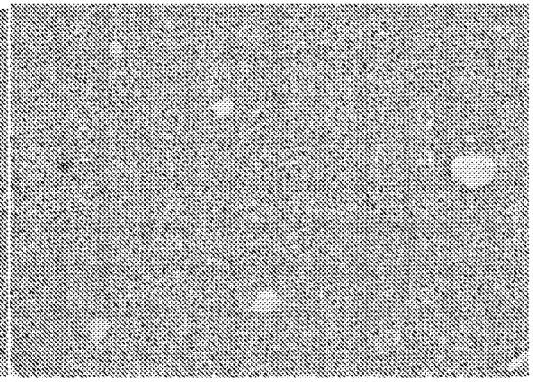
Figure 34:
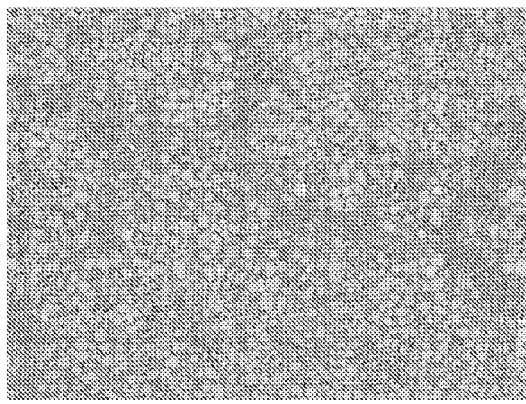
Figure 34:
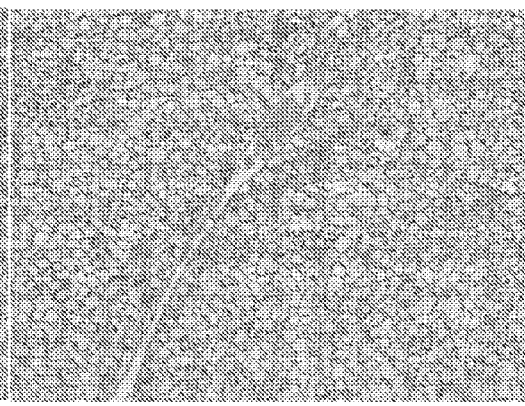

FIG. 34: Liver Histology. Treatment of obese mice with carbon results in a reduction in hepatic fat accumulation and inflammatory cell infiltration. (Ob−: Heterozygote for the ob gene; Ob−/Ob−: Homozygote for the Ob/Ob gene; +C: groups treated with Carbon for 4 weeks).

Figure 35:
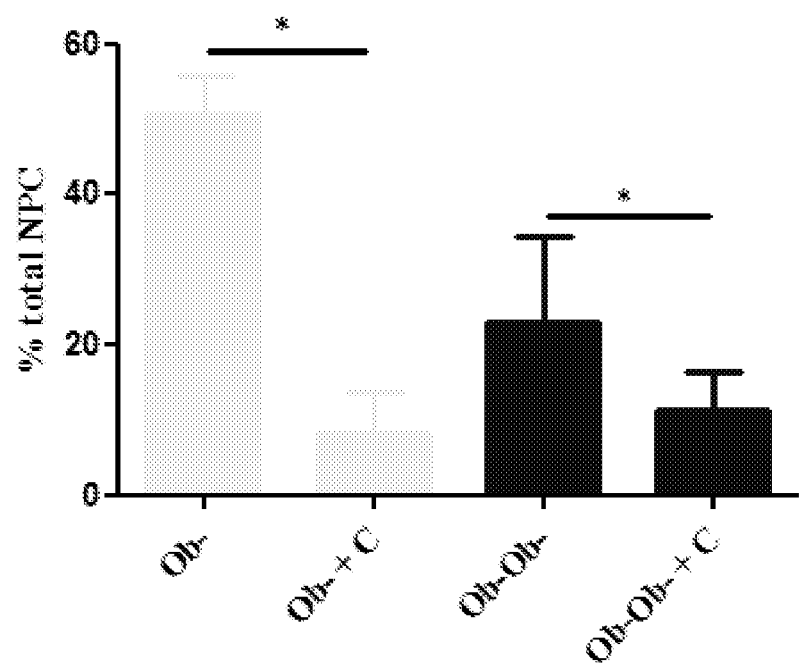

FIG. 35: Kupffer cell population (F4/80+/CD68−/CD11b+). Treatment of obese mice with carbon results in a reduction in the activation of the Kupffer cells. (Ob−: Heterozygote for the ob gene; Ob−/Ob−: Homozygote for the Ob/Ob gene; +C: groups treated with Carbon for 4 weeks).

Figure 36:
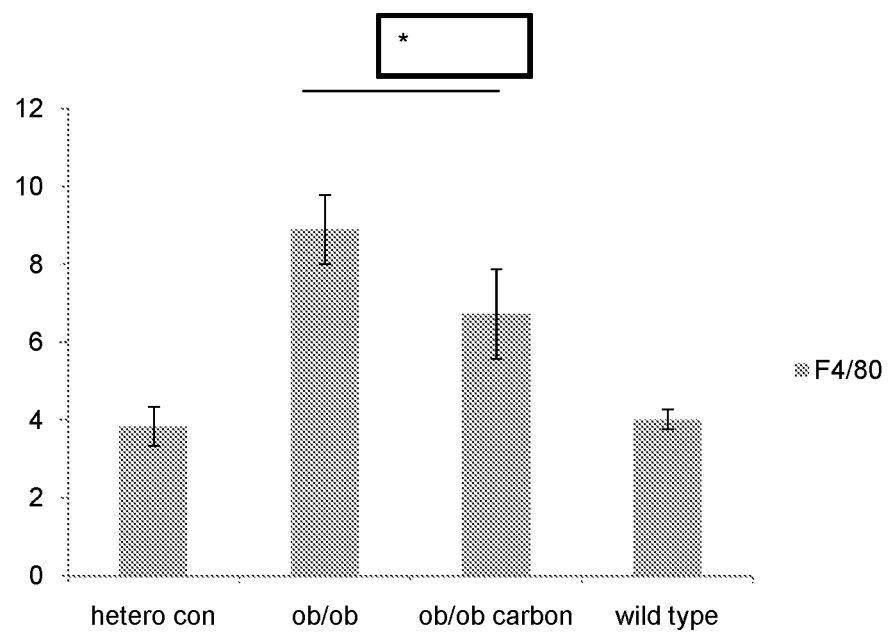

FIG. 36: Kupffer cell population (F4/80+). Treatment of obese mice with carbon results in a reduction in the activation of the Kupffer cells. This provides a possible mechanism by which liver injury is reduced in the Ob/Ob mice treated with the carbon. (Ob−: Heterozygote for the ob gene; Ob−/Ob−: Homozygote for the Ob/Ob gene; +C: groups treated with Carbon for 4 weeks).

Figure 37:
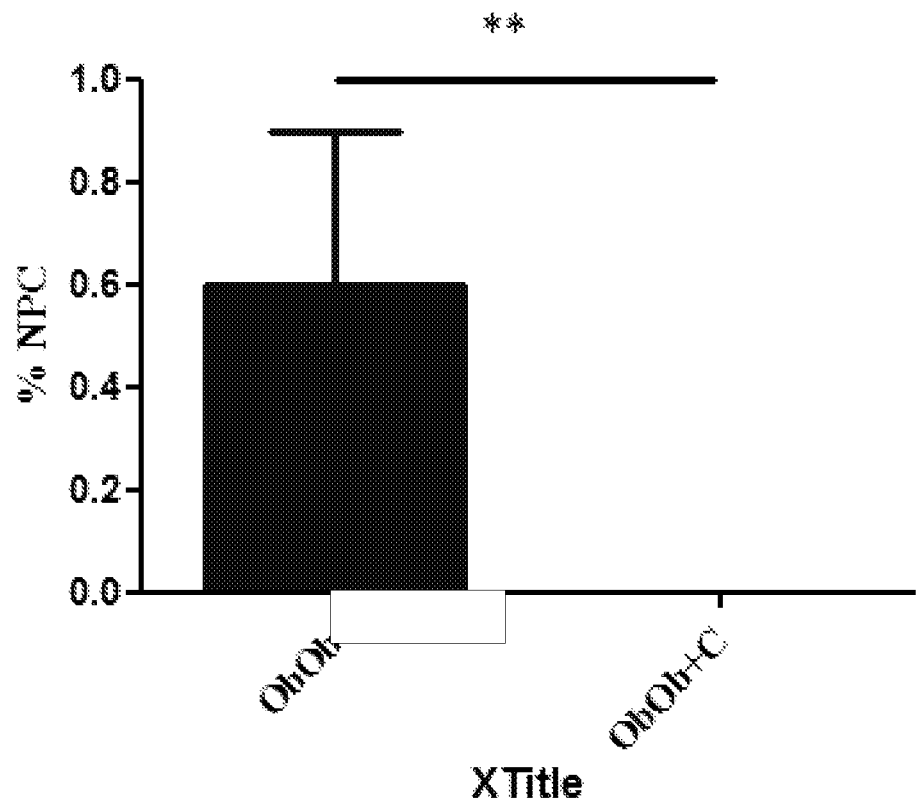

FIG. 37: Kupffer cell population F4/80+LPS: ROS production. Treatment of obese mice with carbon results in a reduction in the production of reactive oxygen species by the Kupffer cells. (Ob−: Heterozygote for the ob gene; Ob−/Ob−: Homozygote for the Ob/Ob gene; +C: groups treated with Carbon for 4 weeks).

Figure 38:
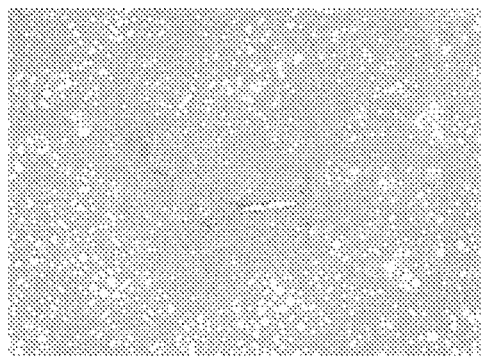
Figure 38:
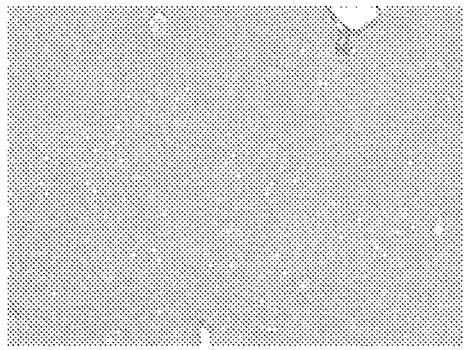

FIG. 38: Liver Histology (Collagen staining). In the half methionine choline deficient diet (HMCD) model of non-alcoholic fatty liver disease, Carbon reduces histological fibrosis suggesting that Carbon treatment may be a treatment for hepatic fibrosis. (HMCD untreated: Diet alone; HMCD Carbon: Diet+Carbon treatment for 4 weeks).

Figure 39:
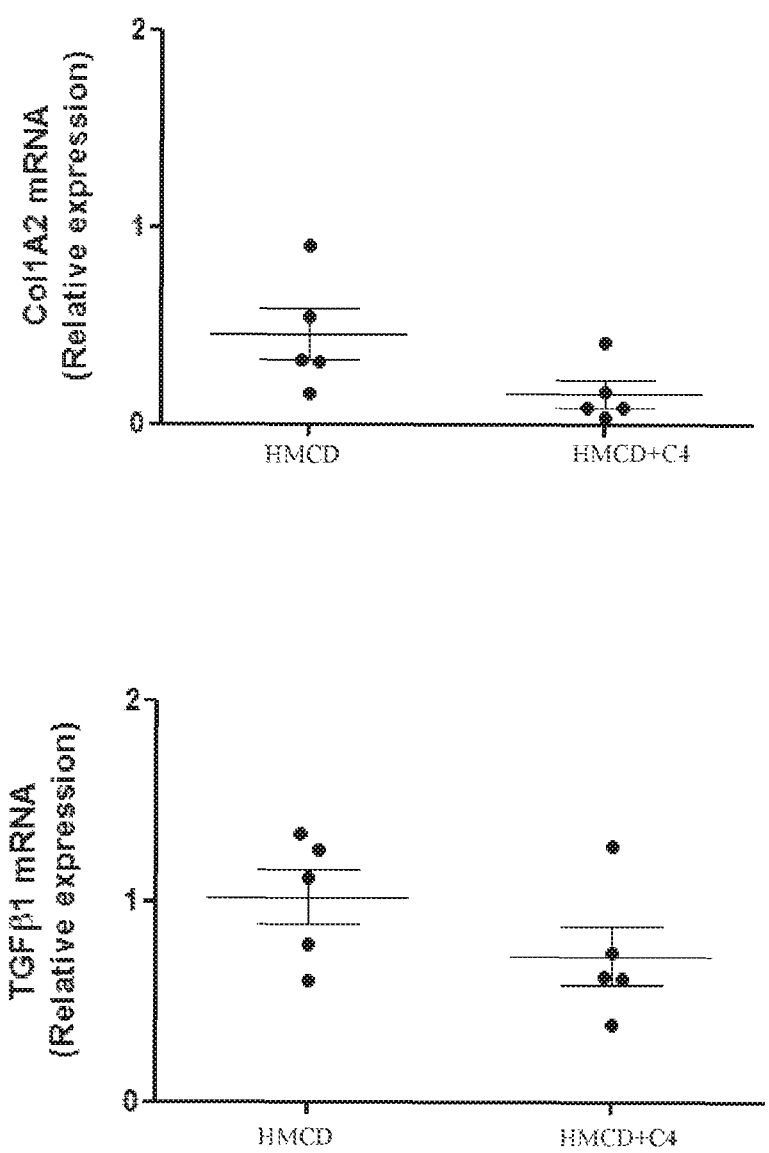

FIG. 39: Liver; Gene Expression for markers of fibrosis. In the half methionine choline deficient diet (HMCD) model of non-alcoholic fatty liver disease, Carbon reduces the gene expression of Collagen A2 and TGFB1. The data support that Carbon may be a treatment for the prevention of hepatic fibrosis (HMCD untreated: Diet alone; HMCD C4: Diet+Carbon treatment for 4 weeks).

Figure 40:
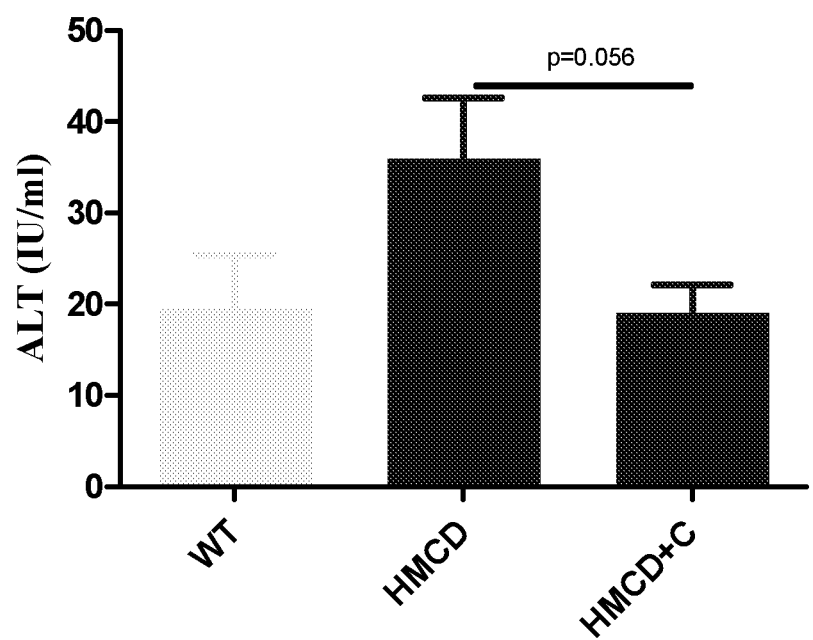

FIG. 40: ALT. In the half methionine choline deficient diet (HMCD) model of non-alcoholic fatty liver disease, administration of Carbon reduces liver injury suggesting that carbon may be a treatment for non-alcoholic fatty liver disease. (HMCD: Diet alone; HMCD+C: Diet+Carbon treatment for 4 weeks; WT: Untreated control).

Figure 41:
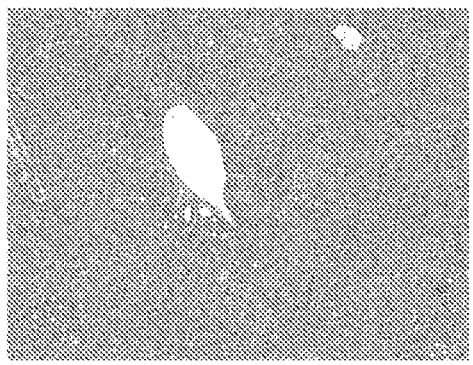
Figure 41:
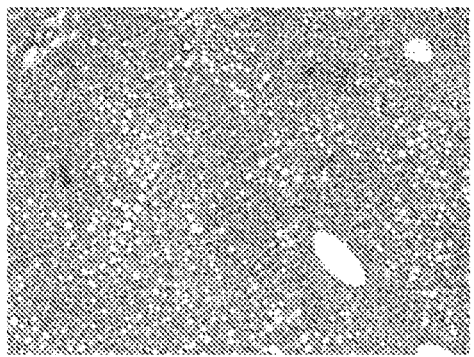
Figure 41:
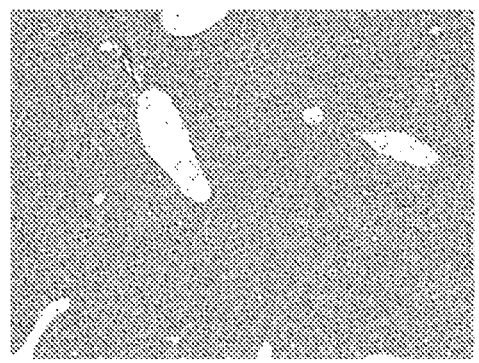

FIG. 41: Liver Histology (H&E staining). In the half methionine choline deficient diet (HMCD) model of non-alcoholic fatty liver disease, Carbon reduces fat accumulation in the liver suggesting that carbon may be a treatment for non-alcoholic fatty liver disease. (HMCD untreated: Diet alone; HMCD Carbon: Diet+Carbon treatment for 4 weeks).

Figure 42:
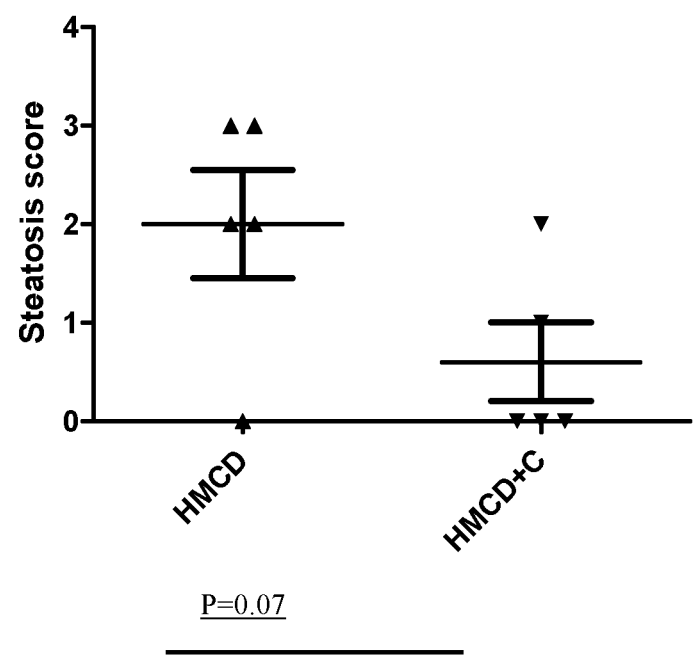

FIG. 42: Liver Histology (Steatosis scores). In the HMCD model of non-alcoholic fatty liver disease, Carbon reduces fat accumulation suggesting that carbon may be a treatment for non-alcoholic fatty liver disease. (HMCD untreated: Diet alone; HMCD Carbon: Diet+Carbon treatment for 4 weeks).

Figure 43:
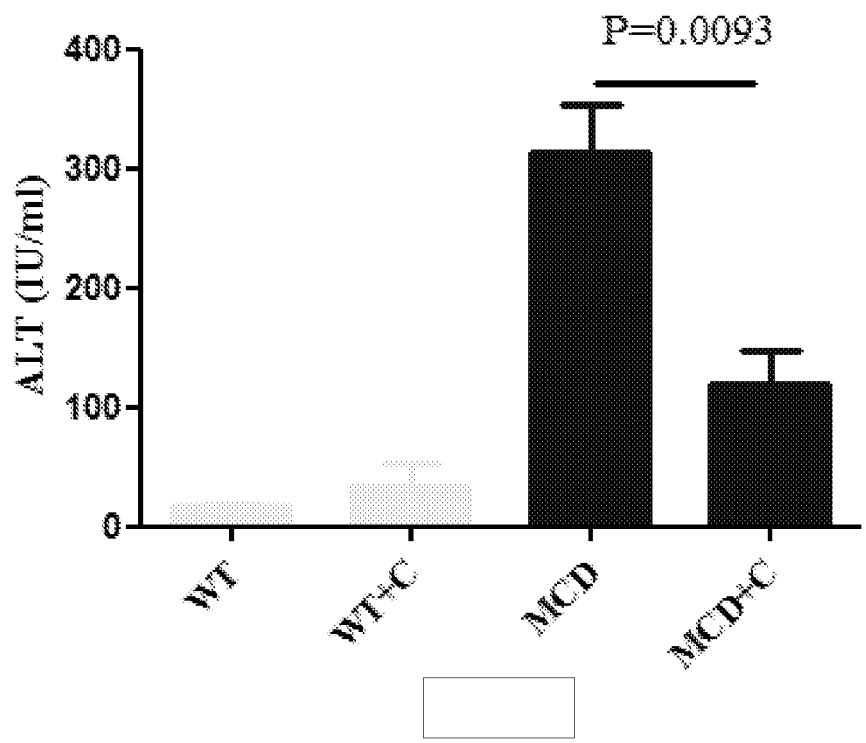

FIG. 43: Liver Biochemistry. In the methionine choline deficient diet (MCD) model of non-alcoholic fatty liver disease, Carbon reduces liver injury suggesting that Carbon may be a treatment for non-alcoholic fatty liver disease. (WT: untreated group; WT+C: untreated group+C; MCD: Diet alone MCD+C: MCD animals treated with Carbon).

Figure 44:
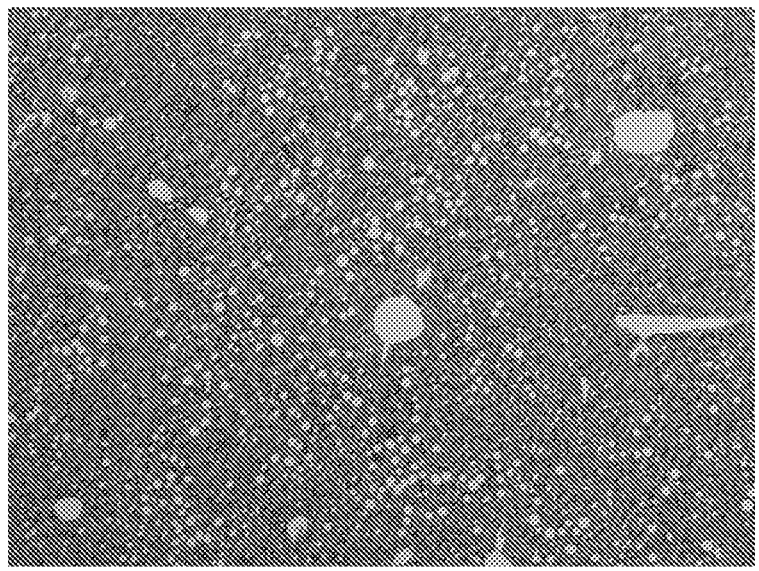
Figure 44:
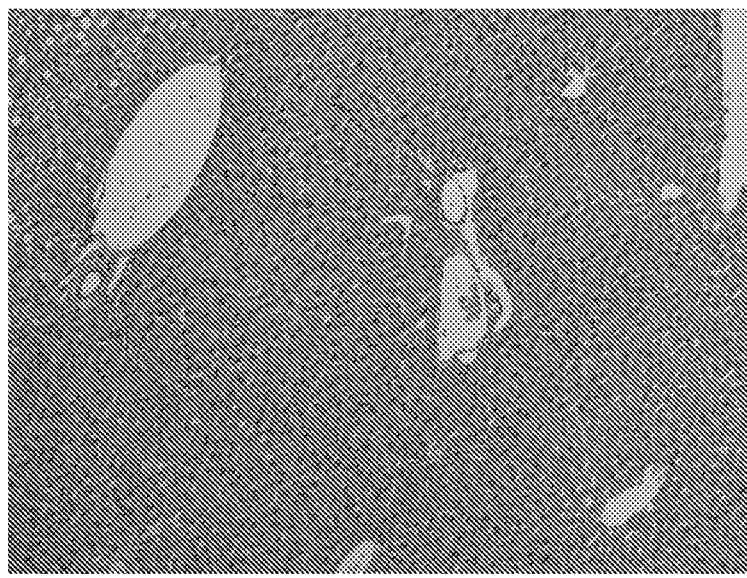

FIG. 44: Liver Histology (H&E staining). In the methionine choline deficient (MCD) model of non-alcoholic fatty liver disease, Carbon reduces fat accumulation suggesting that Carbon may be a treatment for non-alcoholic fatty liver disease. (MCD untreated: Diet alone; MCD+Carbon: Diet+Carbon treatment).

Figure 45:
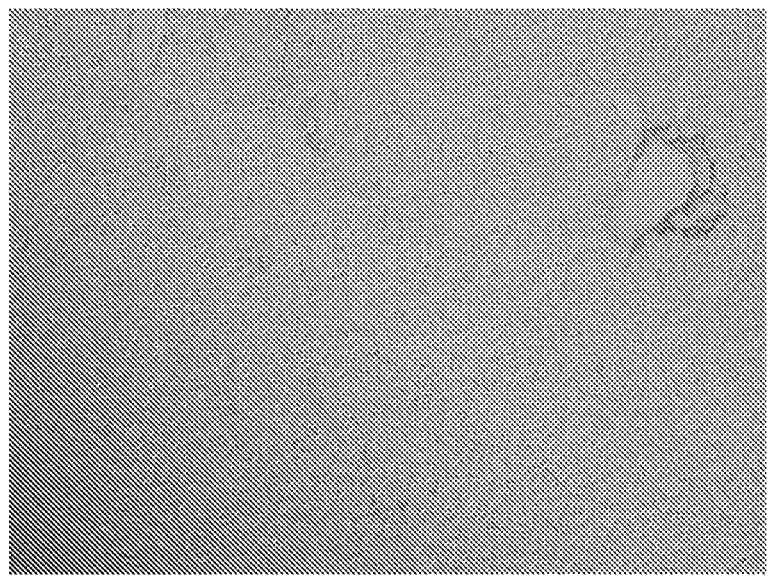
Figure 45:
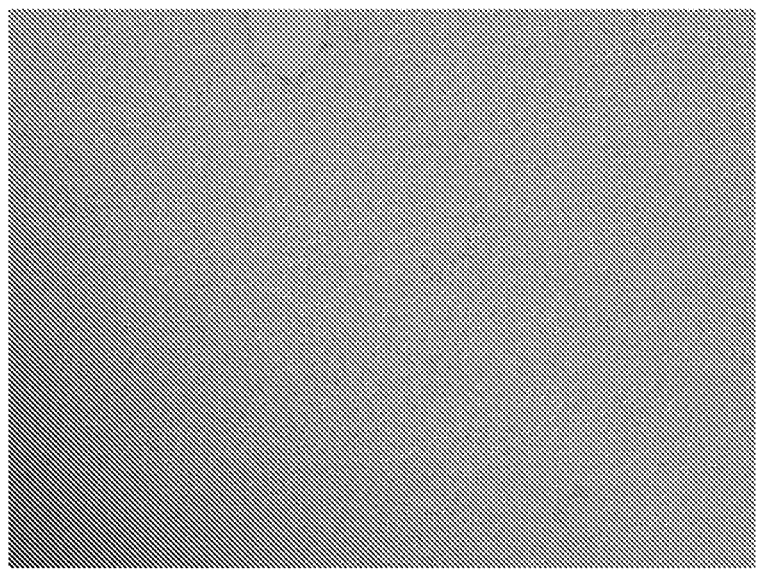

FIG. 45: In the MCD model of non-alcoholic fatty liver disease, Carbon reduces histological fibrosis suggesting that Carbon may be a treatment for hepatic fibrosis. MCD untreated: Diet alone; MCD+Carbon: Diet+Carbon treatment).

DETAILED DESCRIPTION OF THE INVENTION

Throughout this specification, the word "comprise", or variations such as "comprised" or "comprising", will be understood to imply the inclusion of a stated element, integer or step, or group of elements, integers or steps, but not the exclusion of any other element, integer or step, or group of elements, integers or steps.

As used herein the term "carbon particle of controlled porosity" is equivalent to "porous carbon particle".

As used herein, the term "micropore" refers to pores with diameter of 2 nm or less, as measured by nitrogen adsorption and mercury porosimetry methods and as defined by IUPAC.

As used herein, the term "mesopore" refers to pores with diameter of greater than 2 nm and less than 50 nm, as measured by nitrogen adsorption and mercury porosimetry methods and as defined by IUPAC.

As used herein, the term "macropore" refers to pores with diameter of 50 nm or more, as measured by nitrogen adsorption and mercury porosimetry methods and as defined by IUPAC.

The reference to any prior art in this specification is not, and should not be taken as, an acknowledgement or any form of suggestion that that prior art forms part of the general knowledge in Australia or elsewhere.

Currently, the range of treatment or preventions available for patients with liver disease is limited. For many patients the only option is transplant, yet there is no effective treatment or prevention available to extend the lifetime of this group of patients. There is thus a need to find treatment or prevention regimes which can be used to improve the condition of individuals suffering from liver disease.

Gut-derived endotoxaemia is central to the pathogenesis of chronic liver disease and occurs as a consequence of bacterial translocation. Endotoxaemia has been implicated in the pathogenesis of early and end stage cirrhosis, playing a key role in the pathogenesis of acute-on-chronic liver failure, associated with multiple organ failure and a high mortality. A dysregulated inflammatory response is thought to mediate this effect.

Endotoxaemia is also implicated in the pathogenesis of other liver diseases such as ALD and NAFLD, as well as in the pathogenesis of spontaneous bacterial peritonitis, hepatorenal syndrome, variceal haemorrhage, hyperdynamic circulation and hepatic encephalopathy. Multiple lines of evidence implicate endotoxin in immune dysfunction correlated clinically with increased sepsis rates. The pathogenesis of alcoholic liver disease (ALD) is linked directly to ethanol metabolism by intestinal bacteria and the production of acetaldehyde. Acetaldehyde causes a breakdown of normal gut barrier function leading to bacterial translocation into the portal circulation and the release of systemic endotoxin resulting in liver inflammation and injury. Non-alcoholic fatty liver disease (NAFLD) is associated with bacterial translocation and endogenous ethanol production by intraluminal bacteria. Therefore acetaldehyde may play an important role in mucosal injury in this context also.

As highlighted above, bacterial translocation, endotoxaemia and the associated immune/inflammatory response have been implicated in the progression of ALD, NAFLD and complications of cirrhosis. Anatomical and functional gut barrier integrity is a key determinant of bacterial translocation rates and thus endotoxaemia. Binding of bacterial-derived toxin, toxic metabolites and local cytokines should in principle diminish mucosal injury and endotoxaemia. This should have the effect of diminishing liver injury, slowing disease progression and improving neutrophil function. A frequently used strategy to diminish portal endotoxaemia is that of selective intestinal decontamination using oral antibiotics. This represents a good short term strategy with improvement of complications associated with liver dysfunction including hepatic encephalopathy, portal hypertension, hepatorenal syndrome and bacterial peritonitis. However, data demonstrating increases in antibiotic resistance and super-infection limits their role.

The present inventors have investigated the capacity of porous carbon particles having controlled porosity to adsorb biological molecules and their application in treating or preventing liver disease, thus providing an alternative strategy to treatment using conventional antibiotics.

In one aspect, therefore, the invention relates to porous carbon particles for use in the treatment or prevention of liver disease, wherein the particles comprise mesopores of diameter 2-50 nm and small macropores of diameter 50 nm and above. In another embodiment, the porous carbon particles of the present invention comprise micropores of diameter 2 nm or less and mesopores/small macropores of diameter 30 nm to 500 nm, but substantially no mesopores of diameter greater than 2 nm and less than 30 nm, and substantially no large macropores of diameter greater than 500 nm.

The present inventors have found that such non absorbable porous carbon particles having a controlled porosity to provide a relatively high proportion of pores in the meso-to-macroporous range, or in the micro- and small macro ranges, are suitable adsorbants of the pathogenic mediators discussed above and are able to modulate the function of Hepatic Kupffer cells which produce damaging free radicals, possibly through reduction in the translocation of toll-like receptor ligands. The porous carbon particles are non-absorbable and therefore mediate their effect locally at the gut-barrier interface. However unlike conventional non-absorbable antibiotics, the porous carbon particles of the present invention have been shown not to affect detrimentally the growth of bacteria which are important to maintain gut ecology.

Conventionally produced activated carbon (e.g. granular activated carbon) is normally microporous, having pores of diameter less than 2 nm (IUPAC definition), with little or no pore volume in the mesopore (2-50 nm) or macropore (greater than 50 nm) range.

The porous carbon particles for use in the present invention may have 20% to 90% of the total pore volume is made up of pores having a mean diameter of 2 nm or less (micropores), and 75% or more of the remainder of the total pore volume (i.e. the pore volume made up of pores having a mean diameter greater than 2 nm) is made up of pores having a mean diameter of from 30 nm to 500 nm (mesopores/small macropores).

Thus, the porous carbon particles may have a bimodal distribution of pore sizes whereby the total pore volume is distributed between the micropore and large mesopore/small macropore ranges, with substantially no mesopores of diameter less than 30 nm or large macropores. The presence of large macropores is preferably minimised as pores of mean diameter above 500 nm will reduce the physical strength of the particles and provide little or no improvement in adsorption.

Typically, mesopores of diameter less than 30 nm make up 20% of the total pore volume or less, more preferably 15% or less, still more preferably 10% or less. Typically, large macropores make up 20% of the total pore volume or less, more preferably 15% or less, still more preferably 10% or less. Typically, mesopores of diameter less than 30 nm and large macropores together make up 20% of the total pore volume or less, preferably 15% or less, more preferably 10% or less.

Typically, 25% to 70%, preferably 35% to 60%, more preferably 45% to 55% of the total pore volume is made up of pores having a mean diameter of 2 nm or less.

Typically, 80% or more, preferably 85% or more, more preferably 90% or more of the remainder of the total pore volume is made up of pores having a mean diameter of from 30 nm to 500 nm, preferably 30 nm to 300 nm, more preferably 50 to 200 nm.

Typically, the total pore volume as measured by nitrogen adsorption is from 0.5 to 2.5 $cm^3g^{-1}$, preferably 1.0 to 2.0 $cm^3g^{-1}$, more preferably 1.2 to 1.8 $cm^3g^{-1}$. In one embodiment the total pore volume as measured by nitrogen adsorption is 1.3 to 1.8 $cm^3g^{-1}$. In one embodiment the total pore volume as measured by nitrogen adsorption is 1.3 to 1.4 $cm^3g^{-1}$.

Typically, the pore volume attributable to micropores having a mean diameter of 2 nm or less is 0.2 $cm^3g^{-1}$ or more, preferably 0.2 to 0.5 $cm^3g^{-1}$, more preferably 0.3 to 0.4 $cm^3g^{-1}$.

Typically, the bulk density of the porous carbon particles is 0.10 $gcm^{-3}$ or more, preferably 0.15 $gcm^{-3}$ or more, more preferably 0.20 $gcm^{-3}$ or more. Particles having a higher bulk density result in a reduced overall volume of carbon required for oral administration, which is beneficial e.g. for patient compliance. In one embodiment the bulk density of the porous carbon particles is 0.10 $gcm^{-3}$ to 0.30 $gcm^{-3}$, preferably 0.15 $gcm^{-3}$ to 0.25 $gcm^{-3}$, more preferably 0.18 $gcm^{-3}$ to 0.22 $gcm^{-3}$.

In contrast, in one embodiment, in the porous carbon at least 20% of the total pore volume is made up of pores having a mean diameter of from 2 to 200 nm.

Preferably, at least 20% of the total pore volume of the porous carbon particles is made up of pores having a mean diameter of from 20 to 200 nm, preferably from 30 to 200 nm, preferably from 30 to 150 nm, more preferably from 50 to 120 nm, or from 60 to 100 nm. The contribution of pores of these sizes to the total pore volume is preferably greater than 25%, more preferably greater than 30%. Suitably, pores of the aforementioned sizes make up from 25 to 75% of the total pore volume, preferably from 30 to 60%, preferably 30 to 50%, more preferably 30 to 40% of the total pore volume.

The porous carbon particles for use in the present invention may also comprise micropores having a mean diameter of from 0.6 to 2 nm. The contribution of such micropores to the total pore volume may be up to 50%, for example from 5 to 30%.

The porous carbon particles may also comprise larger macropores, having a diameter of greater than 200 nm, for example greater than 500 nm. The contribution of such macropores having a diameter of greater than 200 nm to the total pore volume may be up to 74%, for example from 25 to 70%.

Preferably, the total volume of pores having a mean diameter of from 30 to 150 nm is from 0.2 to 2.0 cm$^3$/g, preferably 0.5 to 1.5 cm$^3$/g.

When the particles additionally comprise micropores, the total volume of micropores having a mean diameter of from 0.6 to 2 nm is preferably from 0.01 to 1.5 cm$^3$/g.

When the particles additionally comprise larger macropores, the total volume of macropores having a mean diameter of greater than 200 nm is preferably from 0.2 to 2.0 cm$^3$/g, preferably from 0.2 to 1.0 cm$^3$/g.

In one particularly preferred embodiment the porous carbon particles for use in the present invention have the properties set out below.

| | |
|---|---|
| Micropore Pore size | 0.5-2 nm |
| BET surface area | 700 to 2000, preferably 1000-1500 m$^2$/g |
| Micropore Pore volume | 0.1 to 1.1 cm$^3$/g, preferably 0.3 to 1.0 cm$^3$/g |
| Meso/small macropore size | 30-500 nm, preferably 50-300 nm |
| meso/small macropore volume | 0.8 to 2.5 cm$^3$/g |
| Total pore volume | 0.9 to 3.5 cm$^3$/g, preferably 1.1 to 2.0 cm$^3$/g |
| Proportion of micropores (% volume) | 27% to 29% |

In one embodiment, the porous carbon particles for use according to the present invention have at least 20% of the total pore volume of the porous carbon particles made up of pores having a mean diameter of from 20 to 200 nm, and 20% to 90% of the total pore volume is made up of pores having a mean diameter of 2 nm or less, but less than 75% of the remainder of the total pore volume is made up of pores having a mean diameter of from 30 nm to 500 nm.

In one embodiment, the porous carbon particles for use in the present invention have 20% to 90% of the total pore volume made up of pores having a mean diameter of 2 nm or less, and 75% or more of the remainder of the total pore volume made up of pores having a mean diameter of from 30 nm to 500 nm, but at least 80% of the total pore volume of the porous carbon particles made up of pores which do not have a mean diameter of from 20 to 200 nm.

Carbon porosity can be measured using mercury porosimetry (e.g. using an automatic mercury intrusion porosimeter such as the PoreMaster® mercury intrusion porosimeter (Quantachrome Instruments)) and/or gas sorption analysis (e.g. using an Autosorb gas sorption analyser (Quantachrome Instruments)).

Mercury porosimetry measures pores greater than 2 nm, particularly greater than 20 nm, and gas sorption analysis is used to measure micropores and mesopores and generally provides an effective measure of porosity for pores having a mean diameter of 0.5 nm to 50 nm, and so it may be necessary to use both methods, especially to measure particles having bimodal porosity as described above. Above 50 nm results obtained by the nitrogen technique may not agree with those obtained by the mercury techniques. In the case of a discrepancy in results for pores of mean diameter greater than 50 nm, the results obtained by mercury should be used.

Figure 1:
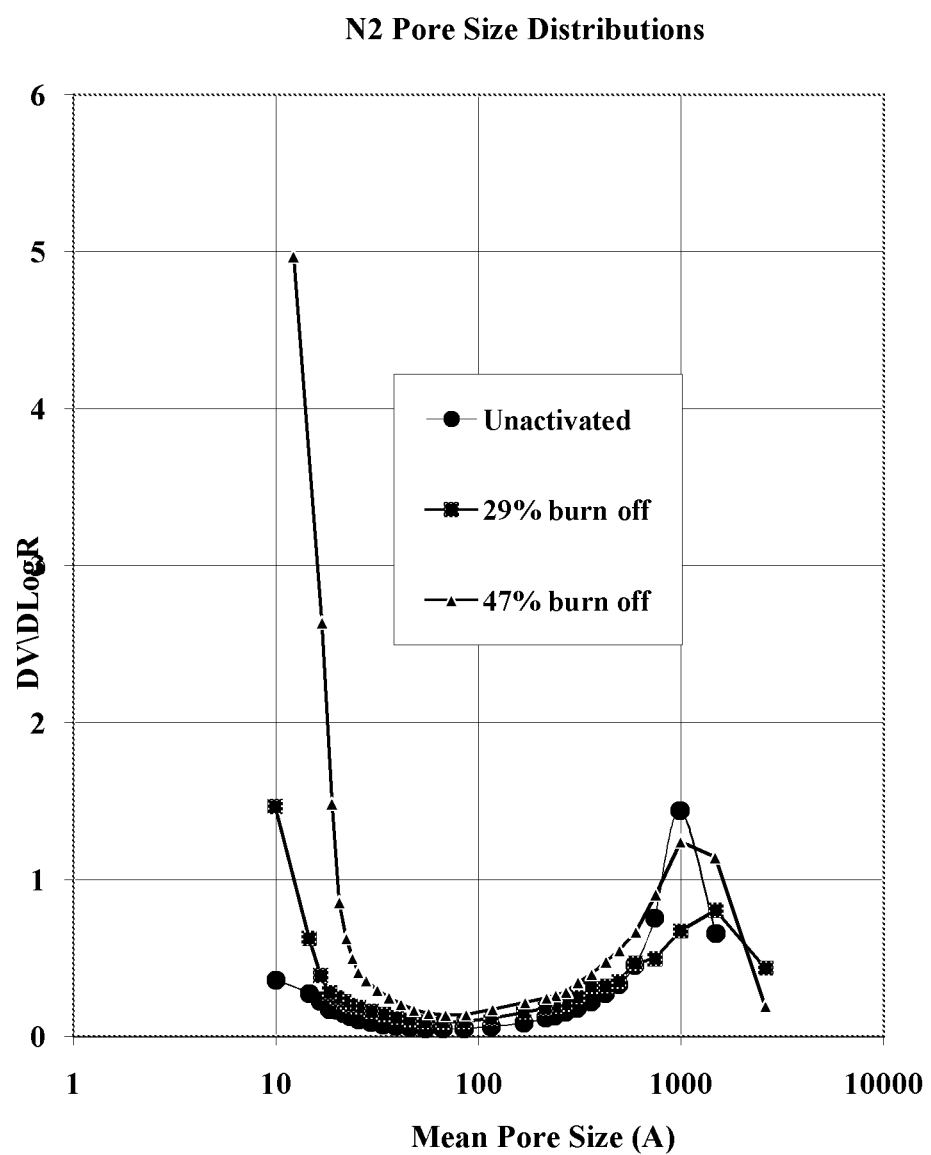
FIG. 1: Pore distribution for phenolic resin derived carbons as measured by nitrogen adsorption and determined using BJH method for TE9 carbons unactivated to activated to 29 and 47% burn off. Activation primarily increases the pores in the micropore (<2 nm diameter). The small macropores (50-500 nm) are largely unaltered with no introduction of pores in the 2-50 nm range (mesopores).
Figure 2:
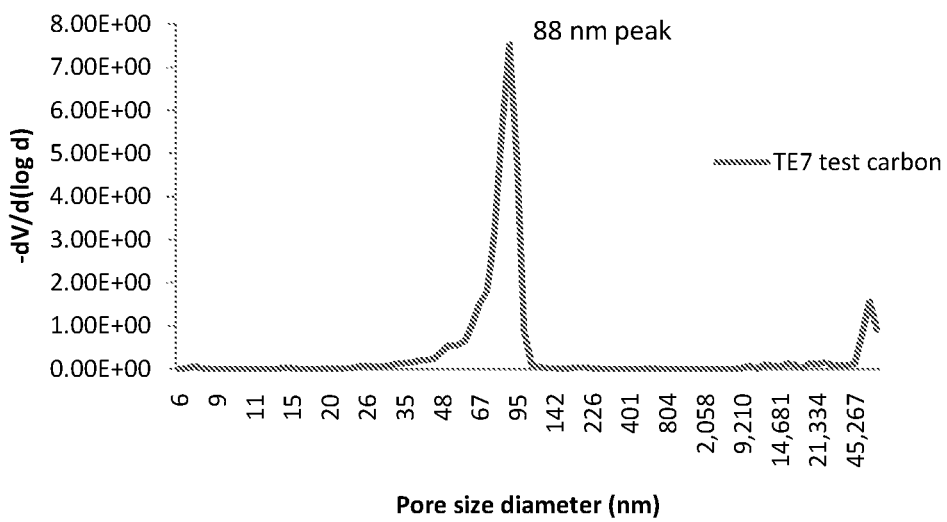
FIG. 2: Representative pore size distribution of porous carbon particles of the invention, measured by Mercury porosimetry (A: TE7 test carbon; B: TE8 test carbon). The larger peak at above 30,000 is due to the voids between the carbon particles and not to porosity.
Figure 2:
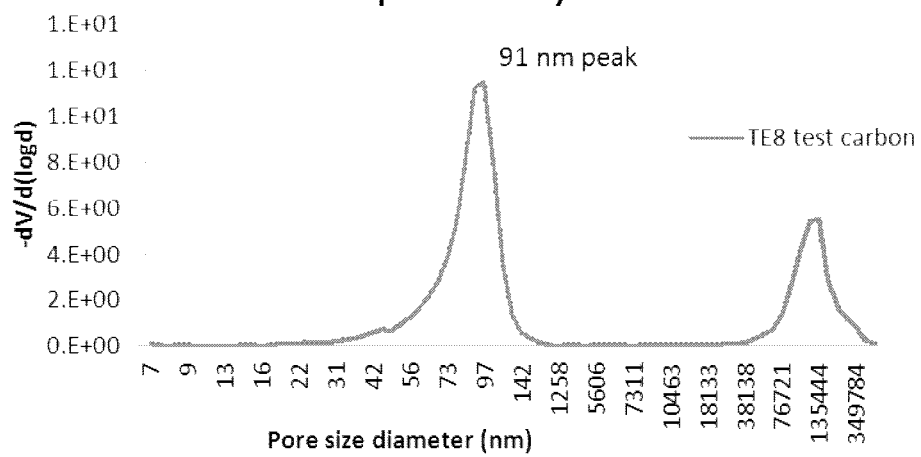

FIG. 2 shows a measure of the pore volume in the larger, small macropores of particles according to the present invention as provided by mercury porosimetry. Micropores are not visible in FIG. 2 because mercury porosimetry measures pores greater than 2 nm. FIG. 1 shows the evolution of the nitrogen pore volume in the <2 nm and 50-500 nm pore range for the TE7 carbon as a function of burn off (degree of activation).

Figure 4:
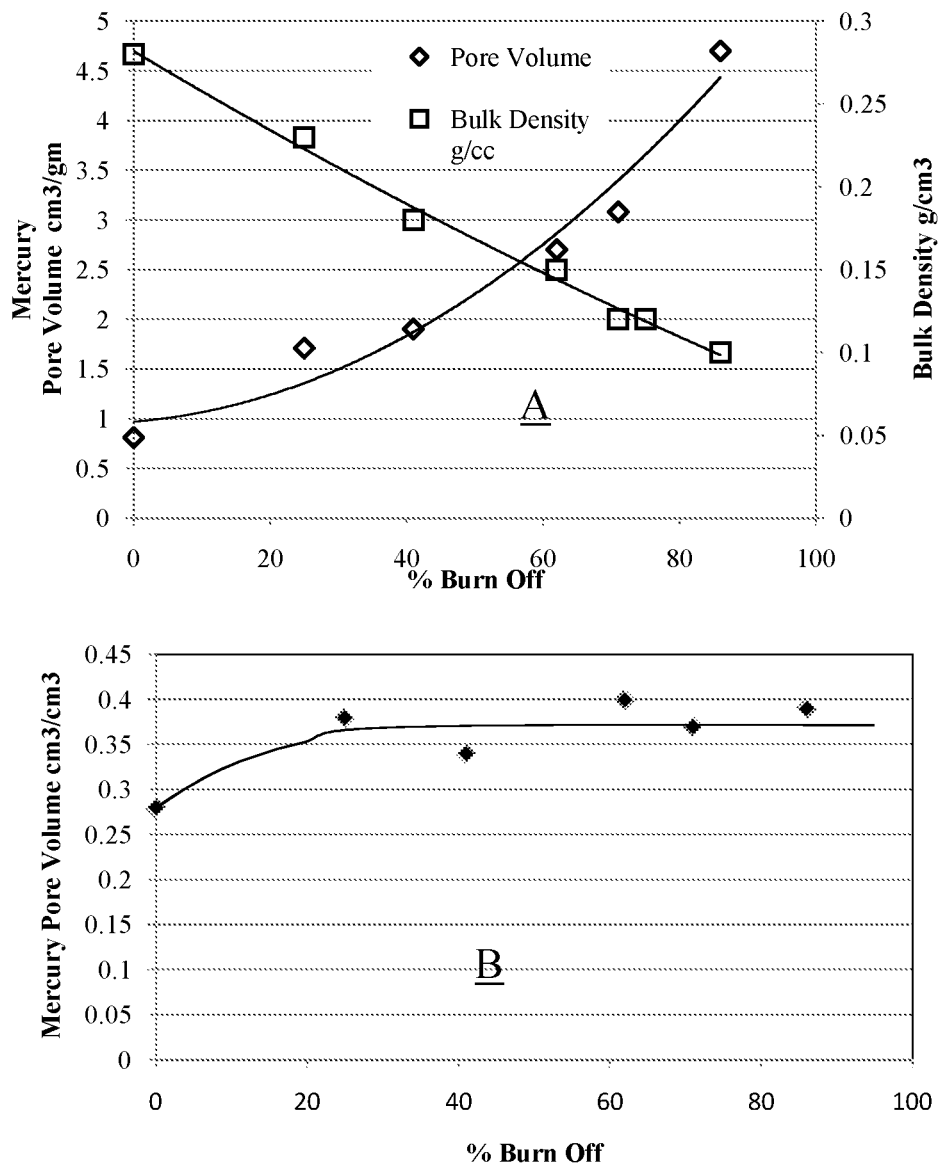
FIG. 4: A Effect of degree of activation on the pore structure as determined by mercury porosimetry, evolution of pore volume on a cm3/gm basis and reduction in bulk density caused by activation; B Effect of degree of activation on pore structure as determined by mercury Porosimetry, change in the mercury pore volume in cm3/cm3 as a function of activation extent.

The change in mercury pore volume with activation is shown in FIG. 4. When the mercury pore volume is reported on a cm$^3$ gm$^{-1}$ basis there is an apparent large increase in pore volume with activation. However this primarily reflects the density decrease with activation. On a volume basis, which is a better reflection of the structure change, the small macropore volume remains constant for all levels of activation, i.e. only the micropore volume is enhanced by activation.

Results obtained by mercury porosimetry may show results at higher pore diameters which correspond to voids between porous carbon particles, and do not reflect the size of pores within the carbon particles. Thus, there will be an effective macropore volume equivalent to ~35% of the volume of the beads attributable to voids, where the void size is ~20% of the bead size. Mercury porosimetry results of 15% of bead size or more, e.g. 20% of bead size or more, can therefore be disregarded when considering porosity. For example, carbon particles of 250-500 µm in size may have an interparticle void size reflected in the mercury data of around 50-100 µm.

Typically, the large mesopore/small macropore volume on a weight basis, determined by mercury porosimetry is 0.60 cm$^3$gm$^{-1}$, preferably higher than 1.1 cm$^3$gm$^{-1}$ and more preferably higher than 1.5 cm$^3$gm$^{-1}$.

The gas sorption analysis technique used to measure micropores is typically nitrogen sorption analysis.

The micro pores in the carbons can be increased by activation and the change in surface area and pore volume with activation is shown in table 2. Preferably, the porous carbon particles have a specific surface area as measured by a BET (Brunauer-Emmett-Teller) method of at least 700 m$^2$/g. The specific surface area may be in excess of 900 m$^2$/g, typically in excess of 1000 m$^2$/g. In one embodiment the specific surface area is over 1200 m$^2$/g. Suitable specific surface areas are in the range of 1000 to 2500 m$^2$/g, preferably 1400 to 2000 m$^2$/g. In one embodiment the specific surface area is from 700 m$^2$/g to 2000 m$^2$/g, typically 900 m$^2$/g to 1400 m$^2$/g, preferably 1000 m$^2$/g to 1200 m$^2$/g. In another embodiment the specific surface area is 1200 m$^2$/g or less, e.g. 700 to 1200 m$^2$/g, 900 to 1200 m$^2$/g or 1000 to 1200 m$^2$/g.

Preferably, the porous carbon particles have a mean diameter of from 2 to 2000 µm, for example from 50 to 2000 µm, from 200 to 1600 µm, or from 100 to 1000 µm. Suitable particles may thus have a mean diameter of, for example, from 200 to 600 µm, preferably 250 to 500 µm. Other suitable particles may have mean diameters of 1000 to 2000 µm, preferably 1000 to 1500 µm. However, particles having a mean diameter of 1000 µm or less are preferred. The particle size can be measured using laser diffraction (e.g. using a Malvern particle sizer (Malvern Instruments)).

Preferably, the porous carbon particles are in the form of spherical particles.

In one embodiment, the porous carbon particles may be surface-modified in order to alter their adsorption capacity for biological molecules.

The porous carbon particles may be in the form of uncoated particles. Such uncoated porous carbon particles have proven biocompatibility. Alternatively, the particles may be coated in order to control their release and adsorption properties. For example, the particles may be coated with a film that will allow predominant release into the large bowel.

The porous carbon particles for use in the present invention may be produced by any suitable method. Suitable methods are described, for example in WO 02/12380.

The present invention also relates to a method of treating or preventing liver disease, comprising administering an effective amount of porous carbon particles wherein at least 20% of the total pore volume is made up of pores having a mean diameter of from 2 to 200 nm, and to use of porous carbon particles wherein at least 20% of the total pore volume is made up of pores having a mean diameter of from 2 to 200 nm in the manufacture of a medicament for the treatment or prevention of liver disease, wherein the porous carbon particles are preferably as described above.

Preparation of Phenolic Resin Derived Spherical Carbon Beads with Bimodal Porosity In relation to this invention there are two types of macropores. In macroporous beads they are located within beads and formed by pore-formers. Their size is typically 30-500 nm, preferably 50-300 nm Typically a precursor resin formulation is used which comprises a significant proportion of pore former, e.g. 250 parts ethylene glycol or other pore former to 100 parts of resin-forming components although high porosity can also be achieved through the use of additives such as urea in combination with the ethylene glycol.

US2008025907A1 (Tennison et al.,) the disclosure of which is incorporated herein by reference) discloses making a mesoporous resin by condensing a nucleophilic component which comprises a phenolic compound or a phenol condensation prepolymer with at least one electrophilic cross-linking agent selected from formaldehyde, paraformaldehyde, furfural and hexamethylene tetramine in the presence of a pore-former selected from the group consisting of a diol (e.g. ethylene glycol), a diol ether, a cyclic ester, a substituted cyclic ester, a substituted linear amide, a substituted cyclic amide, an amino alcohol and a mixture of any of the above with water to form a resin. The pore-former is present in an amount effective to impart macroporosity to the resin (e.g. at least 150 parts by weight of the pore former being used to dissolve 100 parts by weight of the total resin forming components, i.e. nucleophilic component plus electrophilic component), and it is removed from the porous resin after condensation by cascade washing with water or by vacuum drying.

The resulting resin may be carbonised by heating in an inert atmosphere to a temperature of at least 600° C. to give a material having a bimodal distribution of pores, the pore structure as estimated by nitrogen adsorption comprising micropores and mesopores or macropores. The value for the differential of pore volume with respect to the logarithm of pore radius (dV/d log R) for the mesopores is greater than 0.2 for at least some values of pore size in the range 20-500 Å. The mesoporous carbon may have a BET surface area of 250-700 m2/g without activation. It may be activated by heating it at high temperature in the presence of carbon dioxide, steam or a mixture thereof, e.g. by heating it in carbon dioxide at above 800° C. It may then have surface areas of up to 2000 m2/g and even higher e.g. 1000-2000 m2/g. As used herein the term "BET surface area" is determined by the Brunauer, Emmett, and Teller (BET) method according to ASTM D1993-91, see also ASTM D6556-04. For the purposes of the current invention it is preferred to use carbon dioxide.

Phenolic Resins—Nucleophilic Component

Resins for making carbonaceous material can be prepared from any of the starting materials disclosed in US2008025907A1. Nucleophilic components may comprise phenol, bisphenol A, alkyl phenols e.g. cresol, diphenols e.g. resorcinol and hydroquinone and aminophenols e.g. m-amino-phenol.

It is preferred to use as nucleophilic component a phenolic novolac or other similar oligomeric starting material which because it is already partly polymerized makes polymerization to the desired resin a less exothermic and hence more controllable reaction. The preferred novolacs have average molecular weights (AMW) in the range of from 300 to 3000 prior to cross-linking (corresponding to a DP with respect to phenol of about 3-30). Where novolac resins are used, they may be solids with melting points in the region of 100° C. Novolac resins of MW less than 2000 and preferably less than 1500 form crosslinked resins which on carbonisation tend to produce carbons with desired pore size distributions using lower amounts of pore former. Novolacs are thermally stable in that they can be heated so that they become molten and cooled so that they solidify repeatedly without structural change. They are cured on addition of cross-linking agents and heating. Fully cured resins are infusible and insoluble.

Whilst commercial novolacs are largely produced using phenol and formaldehyde, a variety of modifying reagents can be used at the pre-polymer formation stage to introduce a range of different oxygen and nitrogen functionalities and cross-linking sites. These include but are not limited to: —

(a) Dihydric phenols e.g. resorcinol and hydroquinone. Both are more reactive than phenol and can lead to some cross-linking at the pre-polymer production stage. It is also possible to introduce these compounds at the cross-linking stage to provide different cross-linking paths. These also increase the oxygen functionality of the resins.

(b) Nitrogen containing compounds that are active in polycondensation reactions, such as urea, aromatic (aniline, m-amino phenol) and heteroaromatic (melamine) amines. These allow the introduction of specific types of nitrogen functionality into the initial polymer and final carbon and influence the development of the mesoporous structure of both the resins and the final carbons. Like hydroquinone and resorcinol, all the nitrogen containing nucleophilic modifying reagents which can be used possess two or more active sites and are more reactive in condensation reactions than phenol or novolacs. It means that they are first to react with primary cross-linking agents forming secondary cross-linking agents in situ.

The nucleophilic component may be provided alone or in association with a polymerization catalyst which may be a weak organic acid miscible with the novolac and/or soluble in the pore former e.g. salicylic acid, oxalic acid or phthalic acid. Whilst these can be used in the current invention the use of phenol alone preferred to minimise the concentration of more hydrophilic sites.

The concentration of novolac in the pore former may be such that when combined with the solution of cross-linking agent in the same pore former the overall weight ratio of pore former to (novolac+cross-linking agent) is at least 150:100 by weight. The actual ratios of novolac:pore former and cross-linking agent:pore former are set according to convenience in operation e.g. in the case of the process disclosed in WO 2008/043983 (Tennison) by the operational requirements of a bead production plant and are controlled by the viscosity of the novolac:pore former solution such that it remains pumpable and by the ratio of cross-linking agent:pore former such that the cross-linking agent remains in solution throughout the plant Cross-Linking Agents for Phenolic Resins The cross-linking agent is normally used in an amount of from 5 to 40 parts by weight (pbw) per 100 parts by weight of the nucleophilic components e.g. novolac. It may be, for example, an aldehyde e.g. formaldehyde or furfural, it could be hexamethylenetetramine (hexamine), or hydroxymethylated melamine.

Hexamine is preferably used as cross-linking agent. It is preferably used for cross-linking novolac resin at a proportion of 10 to 25 pbw e.g. about 15 to 20 pbw hexamine per 100 pbw of novolac. This ensures formation of the solid resin with maximal cross-linking degree and ensures the stability of the macropore structure during subsequent removal of the pore former.

Pore-Formers

The pore former also acts as solvent. Thus, the pore former is preferably used in sufficient quantities to dissolve the components of the resin system, the weight ratio of pore former to the total components of the resin system resin being preferably at least 1.5:1. Below this level the resulting resins have essentially no macroporosity.

Details of suitable pore formers are given in US2008025907A1 (Tennison). The pore former may be, for example, a diol, a diol-ether, a cyclic ester, a substituted cyclic or linear amide or an amino alcohol e.g. ethylene glycol, 1,4-butylene glycol, diethylene glycol, triethylene glycol, γ-butyrolactone, propylene carbonate, dimethylformamide, N-methyl-2-pyrrolidinone and monoethanolamine, ethylene glycol being preferred, and where the selection is also limited by the thermal properties of the solvent as it should not boil or have an excessive vapour pressure at the temperatures used in the curing process.

It is thought that the mechanism of meso- and macropore generation is due to a phase separation process that occurs during the cross-linking reaction. In the absence of a pore former, as the linear chains of pre-polymer undergo cross-linking, their molecular weight initially increases. Residual low molecular weight components become insoluble in the higher molecular weight regions causing a phase separation into cross-linked high molecular weight domains within the lower molecular weight continuous phase. Further condensation of light components to the outside of the growing domains occurs until the cross-linked phase becomes essentially continuous with residual lower molecular weight pre-polymer trapped between the domains. In the presence of a low level of pore former the pore former is compatible with, and remains within, the cross-linked resin domains, (e.g., <120 parts/100 parts Novolac for the Novolac-Hexamine-Ethylene Glycol reaction system), whilst the remainder forms a solution with the partially cross-linked polymer between the domains. In the presence of higher levels of pore former, which exceed the capacity of the cross-linked resin, the pore former adds to the low MW polymer fraction increasing the volume of material in the voids between the domains that gives rise to the mesoporosity and/or macroporosity. In general, the higher the pore former content, the wider the mesopores, up to macropores, and the higher the pore volume.

This phase separation mechanism provides a variety of ways of controlling the pore development in the cross-linked resin structures. These include chemical composition and concentration of the pore former; chemical composition and quantity of the cross-linking electrophilic agents, presence, chemical nature and concentration of modifying nucleophilic agents, chemical composition of phenolic nucleophilic components (phenol, novolac), the presence of water within the solvent and concentration of any curing catalyst if present.

Production of Resin Precursor and Carbon in Bead Form

In US2008025907A1, production of the resin in both powder and bead form is disclosed. Production of the bead form may be by pouring a solution of a partially cross-linked pre-polymer into a hot liquid such as mineral oil containing a dispersing agent and stirring the mixture. The pre-polymer solution forms into beads which are initially liquid and then, as curing proceeds, become solid. The average bead particle size is controlled by several process parameters including the stirrer type and speed, the oil temperature and viscosity, the pre-polymer solution viscosity and volume ratio of the solution to the oil and the mean size can be adjusted between 5 and 2000 μm. The beads can then be filtered off from the oil. In a preparative example, industrial novolac resin is mixed with ethylene glycol at an elevated temperature, mixed with hexamine and heated to give a viscous solution which is poured into mineral oil containing a drying oil, after which the mixture is further heated to effect curing. On completion of curing, the reaction mixture is cooled, after which the resulting porous resin is filtered off, and washed with hot water to remove pore former. The cured beads are carbonized to porous carbon beads which have a pore structure as indicated above, and may be activated as indicated above. The beads can be produced with a narrow particle size distribution e.g. with a D90:D10 of better than 10 and preferably better than 5.

US2010/0086469 A1 (Tennison) describes and claims a process for producing discrete solid beads of polymeric material e.g. phenolic resin having a porous structure, which process may produce resin beads on an industrial scale without aggregates of resin building up speedily and interrupting production. The process comprises the steps of: (a) combining a stream of a polymerizable liquid precursor e.g. a novolac and hexamine as cross-linking agent dissolved in a first polar organic liquid e.g. ethylene glycol with a stream of a liquid suspension medium which is a second non-polar organic liquid with which the liquid precursor is substantially or completely immiscible e.g. transformer oil containing a drying oil; (b) mixing the combined stream to disperse the polymerizable liquid precursor as droplets in the suspension medium e.g. using an in-line static mixer; (c) allowing the droplets to polymerise in a laminar flow of the suspension medium so as to form discrete solid beads that cannot agglomerate; and (d) recovering the beads from the suspension medium.

Dispersion Medium

For bead production, the pore former comprises a polar organic liquid e.g. ethylene glycol chosen in combination with dispersion medium which is a non-polar organic liquid so as to form a mainly or wholly immiscible combination, the greater the incompatibility between the pore former which forms the dispersed phase and the dispersion medium, the less pore former becomes extracted into the dispersion medium. The pore former desirably has a greater density than the dispersion medium with which it is intended to be used so that droplets of the pore former containing dissolved resin-forming components will pass down a column more rapidly than a descending flow of dispersion medium therein. Both protic and aprotic solvents of different classes of organic compounds match these requirements and can be used as pore formers, both individually and in mixtures. In addition to dissolving the reactive components and any catalyst, the pore former should also, in the case of phenolic resins, be compatible with water and/or other minor condensation products (e.g. ammonia) which are formed by elimination as polymerization proceeds, and the pore former is preferably highly miscible with water so that it can be readily removed from the polymerized resin beads by washing.

The dispersion medium is a liquid which can be heated to the temperature at which curing is carried out e.g. to 160° C. without boiling at ambient pressure and without decomposition and which is immiscible with ethylene glycol and with the dissolved components therein. It may be hydrocarbon-based transformer oil which is a refined mineral oil and is a by-product of the distillation of petroleum. It may be composed principally of C15-C40 alkanes and cycloalkanes, have a density of 0.8-0.9 depending upon grade and have a boiling point at ambient pressure of 260-330° C., also depending upon grade. Transformer oil has a viscosity of about 0.5 poise at 150° C. which is a typical cure temperature. Transformer oil or other dispersion medium may be used in volumes 3-10 times the volume of the combined streams of nucleophilic precursor and crosslinking agent e.g. about 5 times.

Dispersing Agents

Preferred dispersing agents which are dissolved in the dispersion medium before that medium is contacted with the reaction mixture to be dispersed therein to retard droplet coalescence are either sold as drying oils e.g. Danish oil or are produced by partially oxidizing naturally occurring precursors such as tung oil, linseed oil etc. The dispersing agents are consumed as the process proceeds, so that if the dispersion medium is recycled, dispersing agent in the recycled oil stream should be replenished. The dispersing agent is conveniently supplied as a stream in solution in the dispersion medium e.g. transformer oil and e.g. in an amount of 5-10% v/v where Danish oil is used which contains a low concentration of the active component to give final concentration of the dispersant in the dispersion medium 0.2-1% v/v. Higher dispersant concentrations would be used in the case of oxidised vegetable oils.

Solvent Removal from Resin Beads and Granular Materials

The resin beads or granules formed as described above must first be treated to remove the pore former after which they can be carbonised and activated. The pore former can be removed either by water washing or vacuum drying. The beads can be treated directly. If water washing is used this preferably uses at least a two stage process using hot water at ~80 C. This is preferably carried out using a cascade washing process where the water from the second stage, which contains a relatively low level of the pore former, is recycled to the first washing stage. The waste water from the first stage, which contains a high level of the pore former can either be disposed of or the pore former can be recovered by distillation. Vacuum drying can be carried out using any commercially available vacuum dryers although it is preferred that this should use a stirred or moving bed rather than a static tray system.

Carbonisation and Activation of Resin Structures

In US 2010/0098615A1 (Tennison, the disclosure of which is incorporated herein by reference) there is provided a process for carbonizing and activating bead or granular polymeric material and especially the solid beads of polymeric material resulting from the process of US2010/0086469, which comprises supplying the material to an externally fired rotary kiln maintained at carbonizing and activating temperatures, the kiln having a downward slope to progress the material as it rotates, the kiln having an atmosphere free of oxygen provided by a counter-current of carbon dioxide or steam, and annular weirs being provided at intervals along the kiln to control progress of the material.

Alternatively the resin beads can be carbonised and activated on a smaller scale using a batch furnace. Here the carbonisation and activation may be carried out as separate steps where the carbonisation takes place in carbon dioxide at ~800 C and the activation in carbon dioxide at between 850 and 950 C or in steam at between 700 and 850 C.

For the purposes of this invention it is preferred to use carbon dioxide as the activating medium although it is also possible to use other media.

Use of Porous Carbon Particles in the Treatment of Liver Disease

The porous carbon particles described above are useful in the treatment or prevention of liver disease. Liver failure is the final stage of liver disease. Liver failure is divided into types depending on the rapidity of onset. Acute liver failure develops rapidly, but chronic liver failure may take months or years to develop. By definition, liver failure occurs when the liver is so diseased, and functioning so poorly, that encephalopathy is evident. Any progressive liver disease can result in liver failure; examples include: acetaminophen toxicity, cirrhosis, viral hepatitis, and metastatic cancer of the liver. Other signs of liver disease such as jaundice, ascites, fetor hepaticus, and failure of coagulation indicate that the liver is having trouble performing its normal physiological duties, but it is not termed liver failure until the mental status changes appear.

The prognosis for patients with liver disease is difficult to estimate because the condition has many causes.

Accordingly, the present invention may relate to treatment or prevention of an individual whose liver is decompensated or which shows hepatic encephalopathy. The individual's liver may be in the compensated state. The individual may have chronic liver disease. The individual may have liver cirrhosis, for example with or without alcoholic hepatitis. The individual may have acute liver failure. The individual may have hepatic encephalopathy.

The onset of both acute and chronic liver disease may be due to a xenobiotic cause. For example, the individual may have been exposed to a chemical, drug or some other agent which causes liver damage. The individual may have a reaction to an over-the-counter, prescriptive or "recreational" drug which causes liver damage. The individual may have been taking Rezulin™ (troglitazone; Parke-Davis), Serzone™ (nefazodone; Bristol-Myers Squibb) or other drugs thought to cause liver damage. The individual may be one who has had an overdose of a particular drug or exceeded the recommended dosage of a drug capable of causing liver damage. For example, the individual may have taken an overdose of paracetamol. The individual may have been exposed to chemicals which can cause liver damage such as, for example, at their place of work. For example, the individual may have been exposed to such chemicals in an industrial or agricultural context. The individual may have consumed plants which contain compounds which can cause liver damage, in particular this may be the case where the individual is an animal, such as a herbivore. For example, the individual may have consumed a plant containing pyrrolizidine alkaloid such as ragwort. The individual may have been exposed to environmental toxins thought to cause liver disease.

Drug-related liver toxicity comprises more than 50% of all cases with acute liver disease (acute liver failure). Acetaminophen- (also known as paracetamol and N-acetyl-p-aminophenol) toxicity is the most common cause of acute liver failure in the United States and Great Britain. Long-term moderate to heavy alcohol users who take acetaminophen in therapeutic or modestly excessive doses are at risk of severe hepatic injury and possibly acute liver failure. Alcohol use potentiates the toxic effects of acetaminophen. Idiosyncratic drug toxicity also contributes to acute liver failure. Idiosyncratic drug toxicity is thought to be a hypersensitivity response wherein the individual responds to a drug in a pharmacologically abnormal way. This abnormal response can lead to acute liver failure.

The acute liver failure or chronic liver disease may be caused by infection with a pathogenic organism. For example, the liver disease may be due to viral infection. In particular, the individual may be infected, or have been infected, with a virus which causes hepatitis. The individual may have chronic viral hepatitis. The virus may, for example, be hepatitis B, C or D virus. In some cases, and in particular where the individual has viral hepatitis, the individual may also be infected with HIV-I or II. The individual may have AIDS. It is possible that the individual may have been, or be, infected with other organisms which cause liver disease and in particular those which are present in the liver during some stage of their life cycle. For example, the individual may have, or have had, liver fluke.

The individual may have an inherited disease which causes, or increases the risk of, chronic liver disease. For example, the individual may have one or more of hepatic hemochromatosis, Wilson's disease or α-1-antitrypsin deficiency. The individual may have an inherited disorder which causes some kind of structural or functional abnormality in the liver which increases the likelihood of liver fibrosis. The individual may be genetically predisposed to develop an autoimmune disorder which damages the liver and hence which can contribute to liver fibrosis.

The chronic liver disease may be alcohol-induced. A man or woman to be treated may be, or have been, an alcoholic. He or she may be, or have been, consuming on average 50 or more units of alcohol per week, 60 or more units of alcohol per week, 75 or more units of alcohol per week and even 100 or more units of alcohol per week. The man or woman may be, or have been, consuming on average up to 100 units of alcohol per week, up to 150 units of alcohol per week and even up to 200 units of alcohol per week. The measurement of one unit of alcohol differs from country to country. Here, one unit equals 8 grams of ethanol in accordance with the United Kingdom standard.

The man or woman may have been consuming such levels of alcohol for 5 or more years, 10 or more years, 15 or more years or 20 or more years. The individual may have been consuming such levels of alcohol for up to 10 years, up to 20 years, up to 30 years and even up to 40 years. In cases of alcohol-induced liver cirrhosis the individual may be aged, for example, 25 years or over, 35 years or over, 45 years or over and even over 60 years.

The individual may be male or female. Women may be more susceptible to the adverse effects of alcohol than men. Women can develop alcoholic chronic liver disease in a shorter time frame and from smaller amounts of alcohol than men. There seems to be no single factor to account for increased susceptibility to alcoholic liver damage in females, but the effect of hormones on the metabolism of alcohol may play an important role.

Thus, the individual may be suffering from alcoholic hepatitis. Alcoholic hepatitis may range from a mild hepatitis, with abnormal laboratory tests being the only indication of disease, to severe liver dysfunction with complications such as jaundice (yellow skin caused by bilirubin retention), hepatic encephalopathy, ascites, bleeding esophageal varices, abnormal blood clotting and coma.

The individual may have one or more of a number of other conditions known to result in liver damage such as, for example, primary biliary cirrhosis, autoimmune chronic active hepatitis, and/or schistosomiasis (parasitic infection). The individual may have or have had a bile duct blockage.

In some cases, the underlying cause of liver disease may not be known. For example the individual may have been diagnosed as having cryptogenic cirrhosis. Accordingly, the individual may be suspected of having any of the conditions listed herein.

Methods for diagnosing liver disease such as acute liver failure and hepatic encephalopathy are well known in the art and in particular to clinicians and veterinarians in the field. Preferably, the individual will have been diagnosed as having a liver disease and hepatic encephalopathy, for example by a medical or veterinarian professional. The individual may display one or more symptoms associated with liver disease such as one or more of jaundice, ascites, skin changes, fluid retention, nail changes, easy bruising, nose bleeds, oesophageal varices, and in male individuals may have enlargement of breasts. The individual may display exhaustion, fatigue, loss of appetite, nausea, weakness and/or weight loss. The individual may also display one or more symptoms associated with hepatic encephalopathy such as one or more of confusion, disorientation, dementia, stupor, coma, cerebral edema, multiorgan failure (respiratory failure, cardiovascular failure or kidney failure), muscle stiffness/rigidity, seizures or speech impairment. The individual to be treated may or may not be taking other drugs to treat liver disease. The individual to be treated may be at risk of developing hepatic encephalopathy.

The liver disease may have been, or be, confirmed by physical examination including techniques such as ultrasound. Liver biopsies may have been taken to look for build up of fibrosis, necrotic cells, cellular degeneration and/or inflammation and other characteristic features of liver disease. Liver function may have been assessed in the individual to determine whether this is compromised in the individual. The nature and underlying cause of the liver disease may be characterized. Any history of exposure to causative agents of liver disease may be determined.

The individual to be treated may be at risk for hepatic encephalopathic episodes, for example patients who are awaiting liver transplants, surgical and/or portal hypertension patients. A person at risk for hepatic encephalopathic episodes is a person who has not suffered any hepatic encephalopathic episodes or has not suffered any hepatic encephalopathic episode for an extended period of time (about 12 weeks or longer), but has a disorder or medical condition which creates a risk of hepatic encephalopathic episodes. A hepatic encephalopathic episode is a clinical condition characterised by the presence of cerebral dysfunction in patients with liver disease or dysfunction. There is a wide spectrum of mental disturbances in hepatic encephalopathy which range from minimal where the main effects are a reduction in the quality of life, to overt which leads to coma and ultimately death.

The individual on which the method of the invention is practiced may be a liver transplant patient, an individual suffering from reperfusion injury, for example in a graft after liver transplantation or a patient at risk of developing or who has developed multiorgan failure.

Preferably, the liver disease is selected from alcoholic liver disease (ALD), non-alcoholic liver disease (for example non-alcoholic fatty liver disease (NAFLD)), non-alcoholic steatohepatitis (NASH), cirrhosis and/or complications of cirrhosis (for example portal hypertension, ascites, renal failure, hepatic encephalopathy or acute-on-chronic liver failure). The invention may relate to treatment or prevention of inflammation and fibrosis in chronic liver disease, such as ALD, NAFLD or viral hepatitis.

The porous carbon particles described above may also be useful in modulation of the gut-liver axis. Thus the particles may also find use in other conditions where gut translocation is important, such as coronary artery disease, inflammatory bowel disease, irritable bowel syndrome and pouchitis. They may also be useful in treating or preventing hypertension and therefore strokes, as well as in treating or preventing obesity or complications of obesity.

Thus the present invention also relates to a method of modulating the gut-liver axis, comprising administering an effective amount of the porous carbon particles described herein, and to use of the porous carbon particles described herein in the manufacture of a medicament for modulation of the gut-liver axis. The invention also relates to a method of treating or preventing coronary artery disease, inflammatory bowel disease, irritable bowel syndrome, pouchitis, hypertension, stroke, obesity or complications of obesity, comprising administering an effective amount of the porous carbon particles described herein, and to use of the porous carbon particles described herein in the manufacture of a medicament for treatment or prevention of coronary artery disease, inflammatory bowel disease, irritable bowel syndrome, pouchitis, hypertension, stroke, obesity or complications of obesity.

The porous carbon particles of the present invention may be administered in a variety of dosage forms. Thus, the porous carbon particles may be administered orally, for example as tablets, troches, lozenges, aqueous or oily suspensions, dispersible powders or granules. The porous carbon particles may also be administered parenterally, either subcutaneously, intravenously, intramuscularly, intrasternally, transdermally or by infusion techniques. The porous carbon particles may also be administered rectally, for example in the form of a suppository. A physician will be able to determine the required route of administration for each particular patient. Preferably, the porous carbon particles are administered orally or rectally. When administered orally or rectally, the porous carbon particles act intraluminally in the gut, since they are non-absorbable. Preferably, the porous carbon particles are administered orally, for example in free-flowing form (suitably provided in a sachet) or tablet form.

In another embodiment, the porous carbon particles may be used in a method of treating blood extracorporeally, by passing blood through a medical device containing the carbon particles before it is returned to the body, wherein the blood is from an individual having liver disease. This method may be achieved by any suitable means. Blood which has been treated in this way may be returned to the individual for therapeutic purposes, or may be used for another purpose. For example, blood may be treated in this way prior to transfusion into a different individual.

The formulation of the porous carbon particles will depend upon factors such as the nature of the exact agent, whether a pharmaceutical or veterinary use is intended, etc. An agent which is to be used to treat liver disease may be formulated for simultaneous, separate or sequential use.

The porous carbon particles are typically formulated for administration in the present invention with a pharmaceutically acceptable carrier or diluent. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tableting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Formulations for oral administration may be formulated as controlled release formulations, for example they may be formulated for controlled release in the large bowel.

Solutions for intravenous administration or infusion may contain as carrier, for example, sterile water or preferably they may be in the form of sterile, aqueous, isotonic saline solutions.

The dose of the porous carbon particles may be determined according to various parameters, especially according to the substance used; the age, weight and condition of the patient to be treated; the route of administration; and the required regimen.

Again, a physician will be able to determine the required route of administration and dosage for any particular patient. A typical daily dose is from about 0.1 to 2 g per kg of body weight, according to the age, weight and conditions of the individual to be treated, the type and severity of the degeneration and the frequency and route of administration. Daily dosage levels may be, for example, from 0.5 to 15 g, preferably from 1 to 10 g, or if appropriate higher daily dosages such as 10 to 100 g, preferably 20 to 80 g, may be used.

All publications and patent applications mentioned in this specification are indicative of the level of those skilled in the art to which this invention pertains.

All publications and patent applications are herein incorporated by reference to the same extent as if each individual publication or patent application was specifically and individually to be incorporated by reference.

Although the foregoing invention has been described in some detail by way of illustration and example for purposes of understanding, it will be clear to those skilled in the art that certain changes and modifications may be practiced within the scope of the appended claims.

The following Examples illustrate the invention:

Certain Aspects of the Invention

Certain aspects of the invention are disclosed below.
1. Porous carbon particles for use in the treatment or prevention of liver disease, wherein at least 20% of the total pore volume is made up of pores having a mean diameter of from 2 to 200 nm.
2. Porous carbon particles for use according to aspect 1, wherein at least 20% of the total pore volume is made up of pores having a mean diameter of from 30 to 150 nm.

3. Porous carbon particles for use according to aspect 1 or 2, wherein at least 20% of the total pore volume is made up of pores have a mean diameter of from 50 to 120 nm.
4. Porous carbon particles for use according to any one of the preceding aspects, wherein said pores make up at least 25% of the total pore volume.
5. Porous carbon particles for use according to any one of the preceding aspects, wherein said pores make up 30 to 60% of the total pore volume.
6. Porous carbon particles for use according to any one of the preceding aspects, wherein the particles further comprise micropores having a mean diameter of from 0.6 to 2 nm.
7. Porous carbon particles for use according to aspect 6, wherein the micropores make up from 5 to 30% of the total pore volume.
8. Porous carbon particles for use according to any one of the preceding aspects, wherein the particles further comprise pores having a diameter of greater than 200 nm.
9. Porous carbon particles for use according to aspect 8, wherein the pores having a mean diameter of greater than 200 nm make up from 25 to 70% of the total pore volume.
10. Porous carbon particles for use according to any one of the preceding aspects, wherein the total volume of pores having a mean diameter of from 30 to 150 nm is from 0.2 to 2.0 $cm^3/g$.
11. Porous carbon particles for use according to any one of aspects 6 to 10, wherein the total volume of micropores having a mean diameter of from 0.6 to 2 nm is from 0.01 to 1.5 $cm^3/g$.
12. Porous carbon particles for use according to any one of aspects 8 to 11, wherein the total volume of macropores having a mean diameter of greater than 200 nm is from 0.2 to 1.0 $cm^3/g$.
13. Porous carbon particles for use according to any one of the preceding aspects, wherein the total specific surface area as measured by a BET (Brunauer-Emmett-Teller) method is greater than 700 $m^2/g$.
14. Porous carbon particles for use according to aspect 13, wherein the total specific surface area is greater than 1000 $m^2/g$.
15. Porous carbon particles for use according to aspect 14, wherein the total specific surface area is from 1400 to 2000 $m^2/g$.
16. Porous carbon particles for use according to any one of the preceding aspects, wherein the particles have a mean diameter of from 2 to 2000 μm.
17. Porous carbon particles for use according to any one of the preceding aspects, wherein the particles are in the form of spherical particles.
18. Porous carbon particles for use according to any one of the preceding aspects, wherein the particles are administered orally or rectally.
19. Porous carbon particles for use according to aspect 18, wherein the particles are administered orally in free-flowing form or in tablet form.
20. Porous carbon particles for use according to any one of the preceding aspects, wherein the liver disease is selected from alcoholic liver disease (ALD), non-alcoholic liver disease, non-alcoholic steatohepatitis (NASH), cirrhosis and/or complications of cirrhosis.
21. Porous carbon particles for use according to aspect 20, wherein the non-alcoholic liver disease is non-alcoholic fatty liver disease (NAFLD).
22. Porous carbon particles for use according to any one of aspects 1 to 19, for use in treatment or prevention of inflammation and fibrosis in chronic liver disease, such as ALD, NAFLD or viral hepatitis.
23. Porous carbon particles for use according to aspect 20, wherein the complication of cirrhosis is selected from portal hypertension, ascites, renal failure, hepatic encephalopathy and acute-on-chronic liver failure.
24. A method of treating or preventing liver disease, comprising administering an effective amount of porous carbon particles wherein at least 20% of the total pore volume is made up of pores having a mean diameter of from 2 to 200 nm.
25. Use of porous carbon particles wherein at least 20% of the total pore volume is made up of pores having a mean diameter of from 2 to 200 nm in the manufacture of a medicament for the treatment or prevention of liver disease.
26. Porous carbon particles as defined in any one of aspects 1 to 17 for use in modulation of the gut-liver axis.
27. Porous carbon particles for use according to aspect 26, for use in the treatment or prevention of coronary artery disease, inflammatory bowel disease, irritable bowel syndrome, pouchitis, hypertension, stroke, obesity or complications of obesity.

EXAMPLES

Materials and Methods
Carbon Materials

Preparative Example 1

A solution of 100 parts by weight of industrial Novolac resin with an average molecular weight 700-800D (Hexion Specialty Chemicals) in ethylene glycol was heated to 90-95° C. and thoroughly mixed for 2-5 minutes with a solution of 15-20 parts by weight of hexamethylenetetramine (hexamine) in ethylene glycol heated to the same temperature. The resulting clear solution was poured in a stream into 2.5-6 fold volume of stirred hot (150-155° C.) low viscosity mineral oil (insulating oil or transformer oil) containing 0.2-1% (v/v) of a dispersing agent which was an industrial drying oil (Danish oil), a major component being polyunsaturated (oxidised) vegetable oils. The temperature of the mixture fell to 135-140° C., and the mixture was reheated to 150-155° C. over a period of 15-20 minutes. Typically curing occurred within 1-2 minutes at around 140° C. followed by substantial evolution of gas. The further heating to 150-155° C. for 15-20 minutes ensured the completion of curing. The mixture was cooled and the resulting beads were separated from the oil by filtration or centrifugation Ethylene glycol was removed from the resin either by multiple hot water extraction or by drying in vacuum (120° C. at 50 mm Hg). In the above procedure, compared to Example 3 of WO 02/12380, the hexamine content has been increased to 15-20 pbw per 100 pbw of novolac from the previously exemplified 9 pbw, and the temperature of the oil into which the resin solution is poured is increased from 115-120° C. to 150-155° C., and "flash" cure is brought about rather than a "slow" cure as previously exemplified.

Water-washed wet, dried or vacuum-dried resin beads were heat treated to produce carbon materials. A typical procedure comprised but is not restricted to carbonisation in a flow of carbon dioxide with temperature ramping from ambient to 800° C. at 3° C./min, classification by particle size and further "physical" activation of selected fraction in carbon dioxide flow at 900° C. Many variations of this routine known in the art may also be applied. The degree of activation in these samples was approximately 30%.

The meso/macro pore size distribution in the resulting carbons is pre-determined by the porosity of the resin-precursor, which is controlled by the content of the solvent/pore former and the degree of activation of the resulting carbon. Table 1 below gives details of four resin compositions that are precursors to the meso/macro porous carbons, as illustrated by nitrogen porosimetry and mercury porosimetry tests of the activated materials. The predominantly micro-macroporous materials, TE7 and TE8 were used in the subsequent biomedical testing and have a very similar macropore structure. The TE3 and TE5 materials, which have smaller pores in the meso/macro domain are for illustration and give inferior performance in the adsorption of the larger molecules such as TNFα.

The particle size distribution of resulting resin beads depends on various parameters including but not restricted to the type of stirring tool, stirring rate, viscosity of the resin solution, concentration of the dispersing agent, resin solution to oil ratio and temperature of the dispersion. Though the distribution is typically broad the size of the predominant fraction could effectively be shifted between ~10 micron and ~1 mm.

TABLE 1

| Product Code | Novolac solution | | Hexamine solution | |
|---|---|---|---|---|
| | Novolac | Ethylene Glycol | Hexamine | Ethylene Glycol |
| TE3 | 100 pbw | 80 pbw | 20 pbw | 100 pbw |
| TE5 | 100 pbw | 100 pbw | 20 pbw | 120 pbw |
| TE7 | 100 pbw | 150 pbw | 20 pbw | 150 pbw |
| TE8 | 100 pbw | 150 pbw | 20 pbw | 180 pbw |

Figure 11:
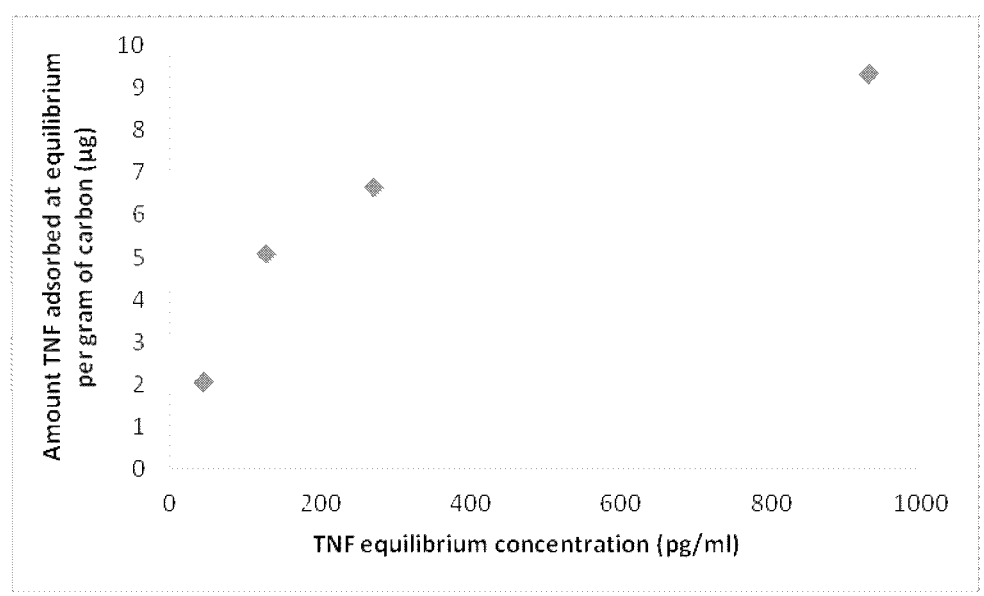
FIG. 11: Removal capacity of TE8 test carbon for TNF from SIF, expressed as an adsorption isotherm showing the amount of TNF adsorbed per gram of carbon (µg) against the equilibrium concentration (mean, n=4).

FIG. 11 shows calculated pore size distributions (BJH model) of activated carbons derived from the TE3, TE5 and TE7 resins respectively (compositions from Table 1): This demonstrates the bimodal nature of the carbon with all of the materials showing a large peak in the <2 nm micro pore size range and a secondary meso/macro peak in the 5-500 nm range where the pore size and the pore volume increases with the glycol pore former concentration as shown in table 1. The preferred materials, TE7 and TE8 have larger meso/small macropores in the 10-500 nm range as measured by nitrogen adsorption. TE3 has a significantly smaller pore volume and the pores extend further into small mesopore (2-50 nm) domain.

Preparative Example 2: Activation of the Carbonised Beads

Figure 3:
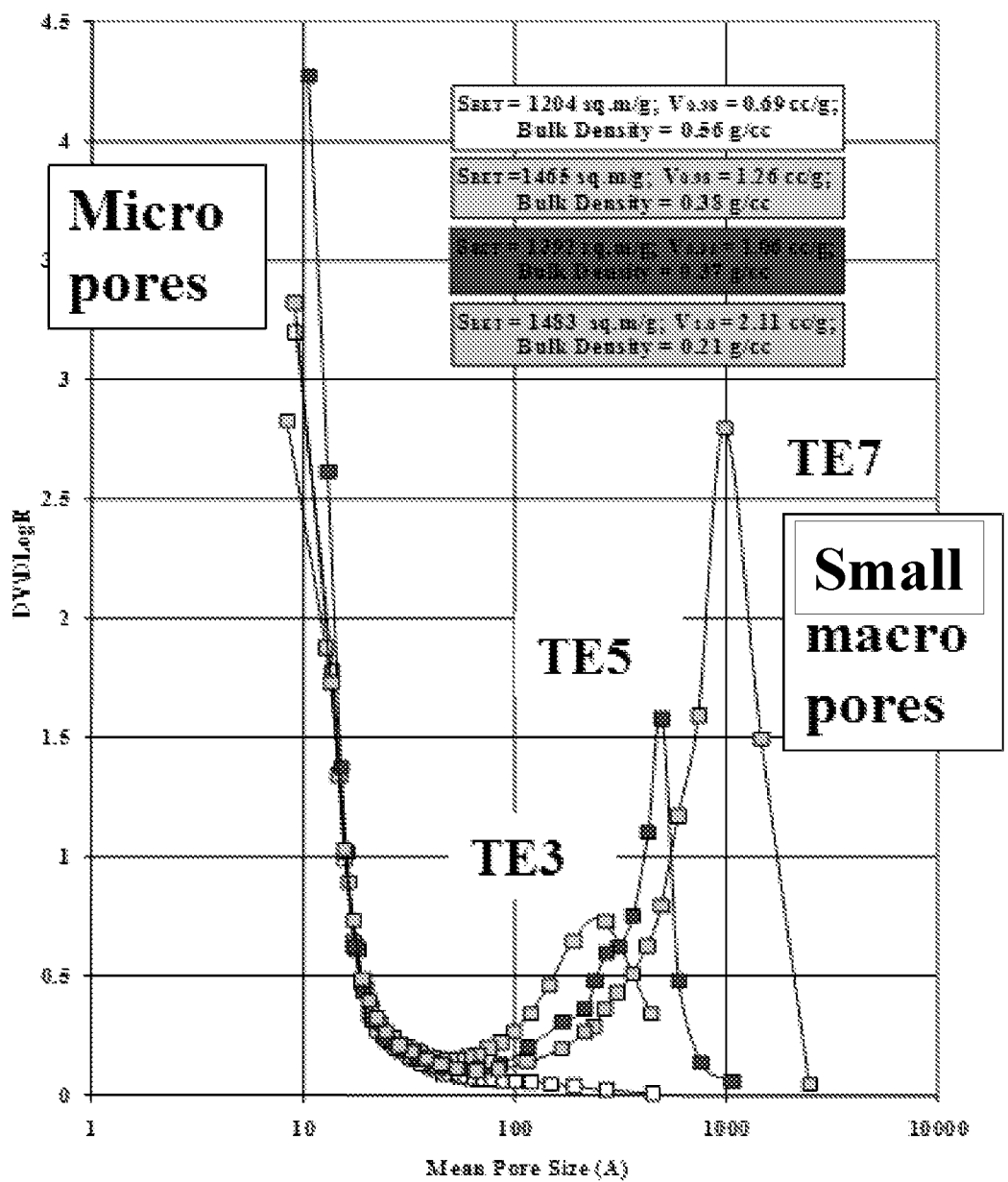
FIG. 3: Increase in the macropore volume (50-500 nm) with the increase in the pore former concentration from TE3 to TE7 for carbon activated to approximately 50% burn off along. No significant introduction of pores in the mesopore range (2-50 nm) or change in the pores in the micropore domain.

The resin beads may be activated in either carbon dioxide or steam. Carbon dioxide is more controllable whilst steam is preferred for larger scale preparations on a cost basis. Activation in carbon dioxide occurs at around 900 C with the degree of burn off controlled by the residence time in the furnace. Steam activation preferably takes place at around 700 C. In both cases the conditions are not critical and the temperature and time can be adjusted to give the required degree of activation as known by anyone skilled in the art. The effect of carbon dioxide activation on the pore structure of the TE8 beads is shown in FIG. 3 with the pore distribution summarised in table 2. The increase in the micro pore volume can be seen from FIG. 3 It can also be seen from table 2 that the pore volume in the micropores (<2 nm) is very low (0.1 cm3/g) in the unactivated sample which also corresponds to the low BET surface area (534 m2/g). Activation to at least 30% burn off significantly increases both the micropore volume and the surface area. The preferred materials for the biomedical adsorption have areas of at least 1000 m2/g, micropore volumes in excess of 0.3 cm3/g.

TABLE 2

Pore structures for CO2 Activated TE8 Carbons

| Material | Density g/cm3 | BET Area m2/g | Total Vol (0.99) 0.99 cm3/g | Incremental Pore Volume | | |
|---|---|---|---|---|---|---|
| | | | | 0-2 nm cm3/g | 2-50 nm cm3/g | >50 nm cm3/g |
| TE8 Unactivated | | 534 | 0.9 | 0.101 | 0.136 | 0.56 |
| 29% activated | 0.22 | 1041 | 1.31 | 0.34 | 0.22 | 0.66 |
| 47% burn off | 0.17 | 1432 | 1.67 | 0.96 | 0.355 | 0.81 |

The change in the macropore volume of the carbon with activation is an artefact of the nitrogen adsorption method but should be >0.5 cm3/g. The larger pore structures should be measured using mercury porosimetry. These are shown for TE7 and TE8 activated to 40% burn off in FIG. 2. The larger pores at >38000 nm are due to interparticle voids between the beads, not to any internal porosity within the beads. The TE7 and TE8 particles have pore diameter peaks at 88 nm and 91 nm respectively, surface area of 1499 m$^2$/g, pore volume of 1.36 cm$^3$/g, bulk density of 0.2 g/cm$^3$, particle size of 240-500 μm and 40% degree of activation. The absence of pores both above the main peak (>300 nm) is readily apparent as is the essential absence of the pores in the mesopore (2-50 nm) domain for both materials. Mercury cannot provide data in pores below ~6 nm due to the pressure involved.

Unless otherwise specified the porous carbon particles used in the following in vitro and in vivo studies were the activated TE7 particles described above.

In Vitro Studies

Investigating the Effect of Direct Contact Incubation of Test Carbons on Bacterial Metabolism Carbon materials (TE7 or TE8 as specified) were weighed into glass universal bottles and dry heat sterilised for 2 hours at 80° C. 1 ml of phosphate buffered saline (PBS) was added to each 0.1 g of material and samples were incubated at 37° C. for 1 hour while shaking at 120 rpm. Tryptone soya broth (TSB) was inoculated with *Escherichia coli* (NCTC 10418) or *Staphylococcus aureus* (NCTC 6571) and incubated overnight at 37° C. while shaking at 120 rpm. The bacterial suspension was pelleted by centrifugation and re-suspended in 1 ml PBS. The absorbance of the suspension was measured at 540 nm and the suspension concentration was adjusted to give a value of 0.5. This dilution factor was then used to prepare a bacterial suspension in TSB. A viability count was carried out on the *E coli* suspension by serial dilution and plating onto agar plates. The inoculum (1 ml) was added to each material and the samples were incubated at 37° C. while shaking at 120 rpm. At timed intervals of 30 mins, 2 and 6 hours 100 μl of bacterial suspension was removed from each sample and placed into the wells of a 96 well plate. Samples were lysed and analysed for ATP content as a measure of cell metabolism using the BacTiter-Glo microbial cell viability assay (Promega).

Investigating the Effect of Carbon Leachate on Bacterial Metabolism

Carbon materials (TE8 and commercially available ACTIDOSE charcoal indicated for poisoning) were weighed into glass universal bottles and dry heat sterilised for 2 hours at 120° C. 2 ml of phosphate buffered saline (PBS) was added to each 0.2 g of material and samples were incubated at 37° C. for 24 hrs while shaking at 120 rpm. TSB was inoculated with *E coli* (NCTC 10418) or *Bacillus subtilis* and incubated overnight at 37° C. while shaking at 120 rpm. The bacterial suspension was pelleted by centrifugation and diluted in TSB to give a final approximate concentration of $1 \times 10^9$ bacteria $ml^{-1}$. In a 100 well Bioscreen plate, 100 µl of extract, 100 µl of inoculum and 100 µl of TSB were added and bacterial growth was measured in a Bioscreen turbidometric analyser monitoring bacterial number at 540 nm for 72 hrs.

Investigating Test Carbon Adsorption of Endotoxin Over Time

Endotoxin removal by TE8 test carbon was measured using a limulus amebocyte lysate (LAL) endosafe endochrome-K test (Charles River Laboratories UK) and Tecan Sunrise incubating plate reader with endoscan-V software. Depyrogenated glassware and endotoxin free plastics were used to minimise endotoxin contamination. TE8 test carbon beads underwent dry heat sterilisation at 250° C. for three hours. Carbons were pre-wetted with simulated intestinal fluid (SIF). SIF was made immediately prior to each experiment according to the United States Pharmacopoeia 26 recipe without pancreatin and using LAL reagent water. A standard lipopolysaccharide (LPS) solution derived from *E coli* 055:B5 was prepared at a concentration of 200 EU $ml^{-1}$ in SIF. SIF was removed from the carbons by aspiration and endotoxin spiked SIF was added to each test carbon at a volume to weight ratio of 10 ml per gram of carbon. Test samples and positive controls without carbon were incubated at 37° C. with shaking and 450 µl of sample was removed at time points of 0, 15, 30, 45 and 60 minutes. The endotoxin concentration of each sample was calculated according to manufacturer's instructions against a standard curve prepared using dilutions from 0.005 to 50 EU $ml^{-1}$.

Investigating Test Carbon Adsorption of TNF

Different weights of carbon bead (TE8 test carbon) ranging from 0.001 to 0.005 g, were placed into sterile labelled eppendorf tubes in quadruplicate and were pre-wetted in 1 ml of SIF in a shaking incubator at 37° C. for 2 hours. Eppendorfs were centrifuged at 8000 rpm for 3 minutes. Supernatant was removed and SIF spiked with 10 ng/ml of recombinant TNF was added. TE8 test carbon adsorbents were incubated at 37° C. while shaking at 90 rpm for 24 hours. Samples were centrifuged at 8000 rpm for 3 minutes and supernatant was collected and stored at −20° C. Samples were diluted in assay diluent before measurement of TNF concentration by ELISA according to the manufacturer's instructions (BD Biosciences).

Investigating the Effect of Carbon Adsorption on Acetaldehyde

Different weights of carbon bead (TE8 test carbon) ranging from 0.001 to 0.005 g, were placed into sterile labelled eppendorf tubes in quadruplicate and were pre-wetted in 1 ml of SIF in a shaking incubator at 37° C. for 2 hours. 7.2 mM spike, 0.1 g/ml) of acetaldehyde was added (n=3, mean+/−SE). Eppendorfs were centrifuged at 8000 rpm for 3 minutes. Acetaldehyde (AT) adsorption was measured using a derivatisation method with 2-diphenylacetyl-1,3-indandione-1-hydrazone (DIH) and detection by HPLC. (FIG. 5B)

In Vivo Studies

All animal experiments were conducted according to Home Office guidelines under the UK Animals in Scientific Procedures Act 1986. Male Sprague-Dawley rats (body weight 280-300 g) were used (Charles River Laboratories UK Ltd.). All rats were housed in the unit and given free access to standard powdered rodent chow and water, with a light/dark cycle of 12 hours, at a temperature of 19° C. to 23° C. and humidity of approximately 50%.

Bile Duct Ligation Model

Under halothane anaesthesia 131 male Sprague-Dawley rats underwent bile duct-ligation or sham biliary surgery. Rats were pair-fed powdered chow+/−pre-hydrated Mast-carbon (250-500 µm) (TE7) at a dose of 0.4 g/100 g body weight per day from two weeks after bile duct ligation until completion of the experiment at 4-5 weeks from initial surgery. Intraperitoneal *Klebsiella* lipopolysaccharide (LPS) (0.33 mg/kg) was administered to 4 subgroups 3.5 hours prior to completion of study. The following groups were studied: Sham (n=15), Sham+carbon (n=17), Sham+LPS (n=11), Sham+LPS+carbon (n=10), BDL (n=22), BDL+carbon (n=25), BDL+LPS+carbon (n=10), BDL+LPS+carbon (n=16).

Intestinal Permeability Assays

Intestinal permeability assays were conducted 1 day prior to completion of the experiment. Animals were placed in metabolic cages for overnight acclimatisation. Baseline urine samples were collected in cryotubes and stored at −70° C. 0.6 ml of a solution of lactulose (277 mM), L(+)-Rhamnose (10 mM) and 3-methyl-o-pyranose (2.0 mM) was then administered by gavage and urine collected for the subsequent 5 hours. Urine samples were analysed using mass spectroscopy. Animals were returned back to their group cages for re-acclimatisation and fasted prior to termination.

Haemodynamic Measurements and Sample Collection

Under halothane anaesthesia (5 ml/min induction 2 ml/min maintenance) an internal carotid catheter (0.96 outer diameter Portex fine-bore polythene tubing, Scientific Laboratory Supplies Ltd., Nottingham, UK) was inserted as previously described. The catheter was held in place for the duration of the study by both proximal and distal holding sutures. The catheter was transduced and mean arterial pressure determined. A laparotomy was then performed under sterile conditions and a catheter placed in the portal vein. Arterial and portal venous catheters were transduced. Concomitant arterial and portal venous plasma was collected aseptically into lithium heparin and EDTA tubes until a state of exsanguination was achieved. 5 ml of ice-cold PBS was then perfused into the liver to achieve organ blanching. The liver was extracted and placed in 10 ml of ice cold PBS. Plasma was centrifuged at 3,500 rpm for 10 minutes at 4° C. The supernatant was transferred immediately to cryotubes and stored at −70° C.

Duodenum, mid-jejunum, terminal ileum and ascending colon was collected and stored in formaline and electron microscopy preservation solution (200 mM sodium cacodylate, 4% gluteraldehyde, pH=7.2-4). Histological specimens were collected with a bed of mesentery with no attempt to irrigate or decontaminate the lumen. Samples were also collected from all four sites following decontamination of the lumen and irrigation with saline solution. These samples were transferred immediately to cryotubes and stored at −70° C. Liver, kidney and brain tissue was also collected and stored in formaline and cryotubes and stored at −70° C.

Isolation of Liver Non-Parenchymal Cells

Perfused liver tissue was dissected with a scapel and homogenized in Hanks balanced salt solution (with calcium and magnesium+collagenase 0.01% and DNAse I (0.01%). The homogenate was transferred to a 50 ml Falcon tube and incubated at 37° C. prior to filtration through a 100 mcm cell strainer. This was then centrifuged at 500 rpm for 5 minutes at 4° C. and the supernatant subsequently centrifuged at 2000 rpm for 10 minutes at 4° C. The supernatant was discarded and the pellet resuspended in PF4 (HBSS with no calcium or magnesium, DNAse I 0.01%, bovine serum albumin (0.25%)) and centrifuged at 2000 rpm for 10 minutes at 4° C. The pellet was then resuspended in 3.9 ml of RPMI 1640 and mixed gently with 2.1 ml (RPMI and optiprep 22%). RPMI was then layered on top followed by 25 minute centrifugation 2800 rpm without brake at 4° C. The non-parenchymal cells were isolated from the interface, resuspended in an equivalent volume of PF4 and centrifuged at 2000 rpm at 4° C. for 10 minutes. $10 \times 10^6$ cells were used in all subsequent assays.

Kupffer Cell Phagocytic Function

The cells were centrifuged at 2000 rpm for 5 minutes at 4° C. and the supernatant discarded. 200 ul of latex beads containing media were added to the pellet and incubated at 37° C. in the dark for 20 minutes. 5 ml of ice cold PBS was then added and centrifuged at 2000 rpm for 5 minutes at 4° C. The pellet was then washed with 5 ml of cold PBS and centrifuged. Fc blocker was then added and incubated for 10 minutes at 4° C. Anti-CD163 antibody was then added and incubated for 30 minutes at 4° C. in the dark.

Kupffer Cell Reactive Oxygen Species (ROS) Production 20 ug/ml of *E. coli* endotoxin was added to $1 \times 10^6$ non-parenchymal cells sample and incubated for 30 minutes at 37° C. ROS inducer at a final concentration of 200-500 uM was used for the positive control. The samples were then centrifuged at 500 g for 5 minutes and the supernatant discarded. The cells were then resuspended in 5 ml of wash buffer, centrifuged at 500 g for 5 minutes and the supernatant removed. The cells were re-suspended in 500 ul of ROS detection solution and incubated for 30 minutes at 37° C. in the dark. Following centrifugation, the cells were resuspended in 100 ul of FACS buffer, Fc blocker added (1:25) and incubated for 10 minutes at 4° C. Anti-CD163 antibody was added and the cells incubated for 30 minutes at 4° C. in the dark. The cells were then washed with 1 ml of FACS buffer, centrifuged and resuspended in 100 mcl FACS buffer solution.

Cytokine Analysis

Portal venous TNFα, IL-4, IL-10 levels were determined using the BD™ Cytometric Bead Array (CBA) kit. 50 μL of the mixed capture beads were added to each assay well of a pre-wetted plate. 50 μL of standard or sample was then added to the assay wells. The plate was agitated for 5 minutes using a digital shaker at 500 RPM and the plate incubated for 1 hour at room temperature. 50 μL of mixed PE detection reagent was then added to each assay well. The plate was then agitated for 5 minutes using a digital shaker at 500 RPM and incubated at room temperature for 2 hours. The plate was vacuum aspirated until the wells were drained. 150 μL of wash buffer was added to each assay well. The plate was then agitated on a digital shaker at 500 RPM for 5 minutes to resuspend the beads. The samples were then analysed by flow cytometry and data analysed using FACS Diva software.

Endotoxin Measurement

The chromogenic limulus amoebocyte lysate kinetic assay (Charles River Laboratories) was used for the detection of endotoxin. Portal venous plasma (100 mcl) was diluted 1:10 with endotoxin-free water and incubated at 75° C. for 30 minutes. 100 mcl of sample and 100 mcl of LAL reagent were mixed in a 96-well plate and analysed at 405 nm with spectrometer using the Endoscan V software. Results are expressed as EU/ml.

Neutrophil Isolation

Whole blood (4 ml) from healthy volunteers was layered over 5 ml of Polymorphoprep and spun for 30 minutes at 400 g at room temperature. Neutrophils were harvested from the second interface and washed with phosphate buffered saline. Neutrophils were counted and resuspended in PBS at a density of $5 \times 10^5$ in 50 mcl:50 mcl of cell suspension and 50 mcl plasma were used per assay. Viability was assessed.

Neutrophil Function

Effect of co-incubation of portal venous plasma on oxidative burst and phagocytosis of normal human neutrophils was determined using Phagoburst and Phagotest assays. The Phagoburst kit (Orpegan Pharma) was used to determine the percentage of neutrophils which produce reactive oxidant species as previously described (FACS Cantoll, BD bioscience). The Phagotest (Orpegan Pharma was used to measure phagocytosis by using FITC-labeled opsonised *E. coli* bacteria as described before. After incubation of cells and plasma for 90 minutes they were washed with PBS and incubated with CD16-PE (3 mcl) (Immunotools). The mean fluorescent intensity of the respective antibodies on neutrophils were analysed by flow cytometry (FACS Canto II, BD bioscience).

Biochemical Analysis

Biochemical profile was determined using standard techniques (COBAS).

Histological Analysis

Liver tissue was processed in accordance with standard protocol and Haematoxylin and Eosin together with Sirius Red staining was performed. Histological staging was conducted by a consultant histopathologist using a 14 point secondary biliary cirrhosis scoring system. Sirius red staining was quantified using computer assisted digital image analysis. Collagen proportionate area was determined using Zeiss KS300 image analysis software. TLR-4 expression in the colon, liver and kidney was determined by immunohistochemistry.

Brain Water Analysis

Brain water was quantified in accordance with standard protocol. 100 g of brain tissue was placed in 100° C. incubator for 24 hours. The percentage water loss was calculated.

Statistical Analysis

Data are expressed as mean±standard error of the mean (SEM). Software used included Graphpad Prism 5.0 (GraphPad software, Inc., San Diego, Calif.).

Results

In Vitro Studies

Figure 6:
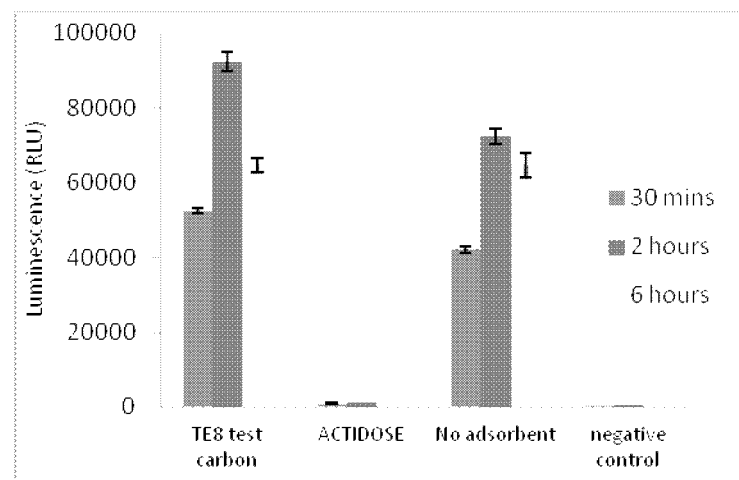
FIG. 6: The effect of TE8 test carbon on bacterial growth measured using the BacTitre-Glo microbial cell viability assay to assess luminescence signal following direct contact with $E\ coli$ over time (inoculum was $3.9 \times 10^9$ bacteria $ml^{-1}$) (mean+/−sem, n=3).
Figure 7:
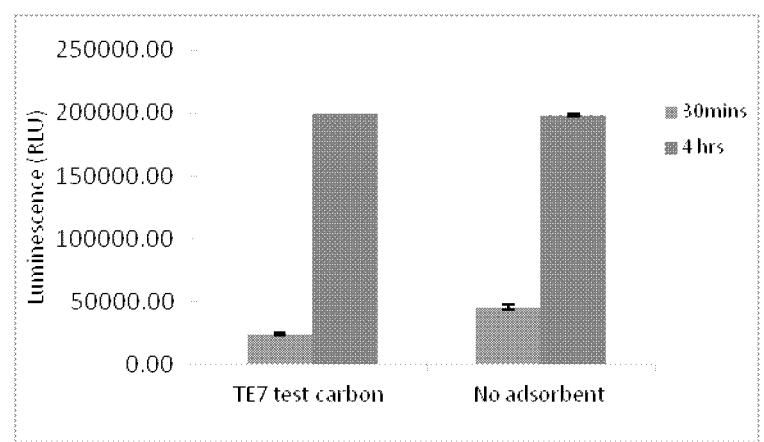
FIG. 7: The effect of TE7 test carbon on bacterial growth was measured using the BacTiter-Glo microbial cell viability assay to assess luminescence signal following direct contact with $S.\ aureus$ over time (inoculum was $7.5 \times 10^7$ bacteria $ml^{-1}$) (mean+/−sem, n=3). The data suggests that the carbon does not kill these bacteria ex-vivo.

Example 1: Investigating the Effect of Direct Contact Incubation of Test Carbons on Bacterial Metabolism The direct incubation of TE8 test carbon with bacterial suspensions of either *E. coli* or *S. aureus* in TSB indicated that the TE8 carbon does not affect bacterial growth for either species following direct contact of 4 to 6 hours (FIGS. 6 and 7). The luminescence measurement is an indirect measure of cell viability and cell number via the determination of bacterial ATP. Levels of luminescence, reflective of bacterial metabolism on sample contact, were comparable to the no adsorbent control for both species over the time course of the experiment. In contrast, the control commercial ACTIDOSE oral carbon greatly reduced the luminescence signal after only 30 minutes incubation of bacteria with the carbon.

Figure 8:
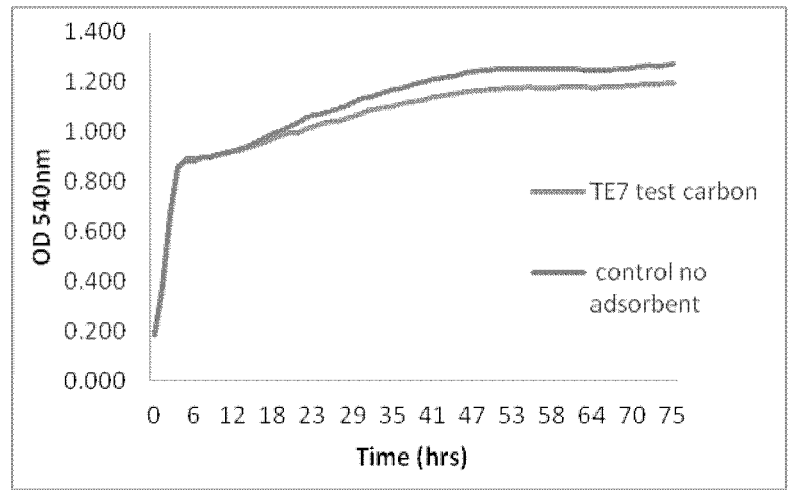
FIG. 8: The effect of TE7 test carbon leachate on the growth characteristics of $E\ coli$ over time was measured by increasing turbidity (540 nm) using a Biscreen turbidometric analyser (mean, n=4). The data suggests that the carbon does not kill these bacteria ex-vivo.
Figure 9:
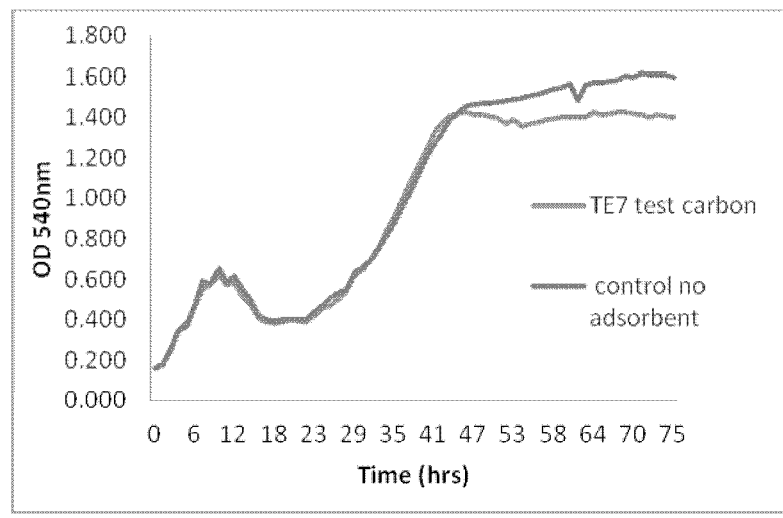
FIG. 9: The effect of TE7 test carbon leachate on the growth characteristics of $B\ subtilis$ over time was measured by increasing turbidity (540 nm) using a Biscreen turbidometric analyser (mean, n=4). The data suggests that the carbon does not kill these bacteria ex-vivo.

Example 2: Investigating the Effect of Carbon Leachate on Bacterial Metabolism The direct incubation of TE7 carbon leachate with bacterial suspensions of either *E coli* or *Bacillus subtilis* in TSB indicated that the TE7 carbon leachate does not affect bacterial growth for either species for up to 72 hrs incubation (FIGS. 8 and 9). The optical density (OD) measurement is an indirect measure of bacterial number. OD values for the TE7 sample were comparable to the no adsorbent control for both species over the time course of the experiment.

Example 3: Investigating Test Carbon Adsorption of Endotoxin Over Time

Figure 10:
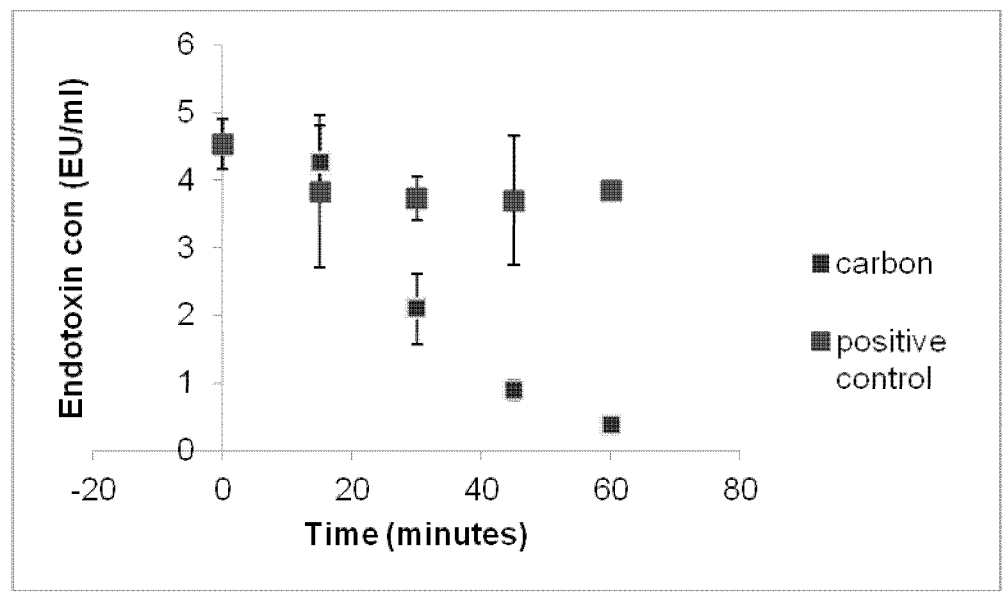
FIG. 10: A. The removal of endotoxin by test carbons over time compared to no carbon controls (n=3, mean+/−SEM); B. The removal of endotoxin by test carbons over time compared to no carbon controls; higher endotoxin spike (0.1 g, 200 EU/ml spike in SIF) (n=3).
Figure 10:
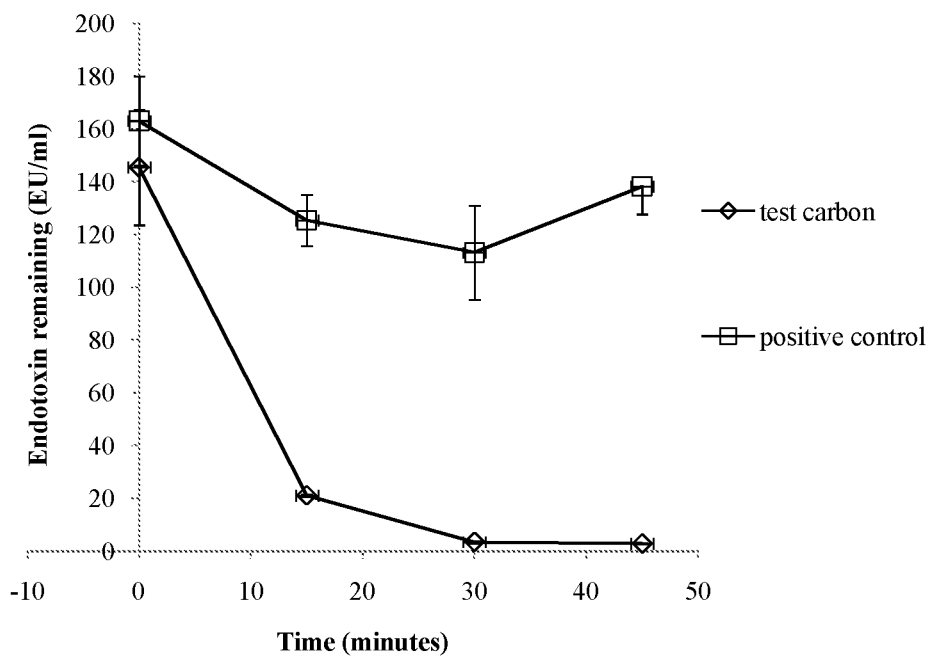

The concentration of endotoxin detected in the SIF solution initially spiked with 200 EU ml-1 declined from a detected value of 160 EU ml$^{-1}$ at time 0 to 30 EU ml$^{-1}$ following 60 minutes incubation with the test carbons (FIG. 10). The control solution maintained a steady 160 EU ml$^{-1}$ concentration over time.

Example 4: Investigating Test Carbon Adsorption of TNF

The removal capacity of TE8 test carbon for the inflammatory cytokine TNF from SIF is shown in the adsorption isotherm (FIG. 11). The maximal amount of TNF adsorbed at equilibrium by the TE8 carbon was determined to be 10 µg g$^{-1}$ of carbon.

Example 5: In Vivo Studies

A significant reduction in portal pressure was observed in BDL+LPS (mean 18.05 mmHg untreated, 10.17 mmHg with carbon, p=0.0007) and BDL (mean 12.57 mmHg untreated, 11.02 mmHg with carbon, p=0.0043) groups following carbon treatment. No significant change in mean arterial pressure was observed (FIG. 14).

Figure 12:
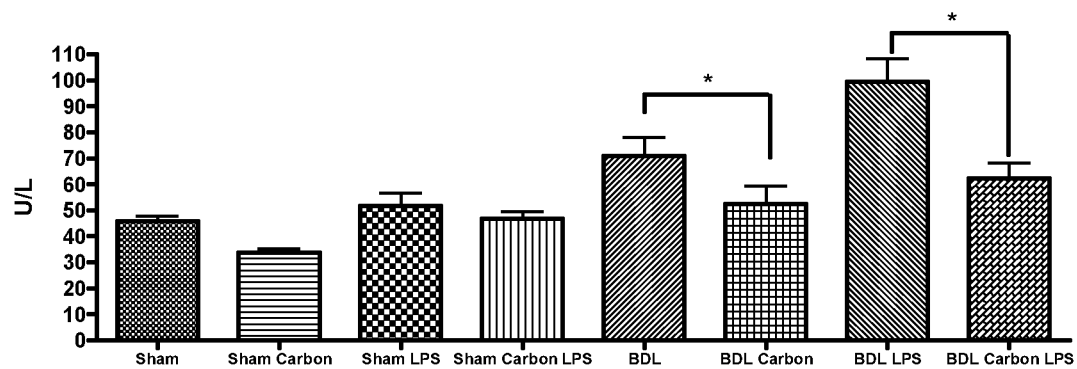
FIG. 12: Liver biochemistry—ALT: A significant reduction in alanine transaminase (ALT) was observed in the carbon treated BDL and BDL+LPS groups compared to untreated groups. Carbon treatment was associated with a reduction in ALT from 99 U/ml to 62 U/ml in BDL+LPS rats (p=0.0152) and from 71 U/ml to 52 U/ml (p=0.0422) in BDL rats. (Sham: Sham operated, BDL: Bile-duct ligation

A significant reduction in alanine transaminase (ALT) was observed in the carbon treated BDL and BDL+LPS groups compared to untreated groups. Carbon treatment was associated with a reduction in ALT from 99 U/ml to 62 U/ml in BDL+LPS rats (p=0.0152) and from 71 U/ml to 52 U/ml (p=0.0422) in BDL rats (FIG. 12). An increase in Kupffer cell population was observed in BDL and BDL+LPS rats. Treatment with carbon resulted in a significant reduction towards sham control values in both groups (p=0.0286, p=0.0357). Total liver ROS production was found to be increased in BDL rats compared to sham consistent with an increase in liver injury. Carbon treatment in BDL rats was associated with a marked reduction in total ROS production approaching sham values. Kupffer cell phagocytosis was observed to be increased in BDL and BDL+LPS rats. A normalization of phagocytosis towards sham values was observed with carbon treatment (FIGS. 17 to 21).

A non-significant reduction in GMFI was observed following incubation of portal venous plasma from BDL and BDL+LPS rats with normal neutrophils. The reduction in GMFI following carbon treatment was from 1115 to 944 in BDL rats and 1104 to 998 in BDL+LPS rats. A trend towards reduction in portal venous IL-4 and IL-10 were observed in carbon-treated BDL rats. Portal venous TNFα and endotoxin levels were observed to be lower in the carbon treated group but this was not statistically significant. TLR-4 and 2 expression in the colon was not found to be different between treatment and non-treatment groups.

No difference in collagen proportionate area were observed between treatment and non-treatment BDL and BDL+LPS groups. Expression of smooth muscle actin in liver was found to be diminished in carbon treated BDL and BDL+LPS groups on immunohistochemistry possibly explaining the mechanism of reduction in activation of the stellate cells.

Gut permeability was normalised in the animals treated with carbon (FIG. 22). A significant increase in the dry final body weight was observed in the BDL carbon-treated group (p=0.0271) (FIG. 15). Histology of the ileum, jejunum and colon remained unaffected following treatment with the Carbon (FIG. 28).

Obesity

The effect of porous carbon nanoparticles on obesity was examined in a model of Ob–/Ob– mice. 10-14 week old leptin deficient genetically obese male mice underwent carbon therapy (0.04 g/10 g/day). Mice underwent hepatic perfusion with 5 ml ice-cold PBS into portal vein. Results were collected by Kupffer cell isolation and characterisation by FACS analysis without cell permeabilisation:
F4/80 (Kupffer cell marker)
CD68 (Macrophage marker)
CD11b (Mediates interaction with stimulated endothelium, phagocytosis, respiratory burst)
ROS (Reactive Oxidant Species) Assay+/–LPS challenge
Phagocytosis Assay Half Methionine Choline Deficient (HMCD) and Methionine Choline Deficient (MCD) Experiments The effect of porous carbon particles was examined in a half methionine choline deficient model of hepatic oxidative stress in order to study inflammatory and fibrotic elements of NAFLD. Carbon was fed to HMCD fed mice from 2 weeks at a dose of 0.4 g/100 g/day. A full MCD diet was used to achieve more advanced disease. Carbon was fed to MCD fed mice from day 1 in a 4 week model at a dose of 0.4 g/100 g/day Distant Organ Effects No significant difference in renal histology with routine staining (H&E and PAMS). TLR-4 expression in the kidney was not significantly different. Serum creatinine, as a reflection of renal function was lower in the BDL+LPS group treated with carbon but not significantly different (FIG. 30). Brain water was lower in the carbon-treated BDL+LPS group but not statistically significant (FIG. 30). No evidence of carbon embolisation was observed at either a macroscopic or microscopic level.

Discussion

We demonstrate in vitro that micro/mesoporous carbons have the optimal porosity to bind intraluminal factors relevant to the pathogenesis of chronic liver disease. A high affinity for free endotoxin was demonstrated but with no significant effect on bacterial growth kinetics. Micro-/mesoporous carbons are therefore acting as endotoxin adsorbents without antibiotic effects. Translocation of bacterial products in the absence of viable bacteria is a recognized phenomenon in cirrhosis. Clinical studies have shown that culture-negative bacterial PCR positivity in serum and ascites is predictive of survival. Translocation of free intraluminal endotoxin has been demonstrated in BDL rats and shown to drive systemic endotoxaemia, implicated in the pathogenesis of ACLF. Therefore micro-/mesoporous carbons, with the capacity to bind free endotoxin, have the potential to diminish this process. Furthermore, in not influencing bacterial growth kinetics, carbons are not likely to be associated with the side effects attributed to antibiotic therapy. These include antibiotic-induced dysbiosis with a shift in the commensal flora towards resistant bacterial populations in the gut with potentially more deleterious effects. In addition, antibiotics result in endotoxin generation and have a variable influence on endotoxin kinetics dependent on antibiotic class. In the absence of antibiotic activity, this effect will not be observed with carbon therapy.

Endotoxaemia is known to drive a dysregulated inflammatory response in cirrhosis. The in vitro data in this study confirms that micro-mesoporous carbons have a high affinity for pro-inflammatory cytokines of potential relevance to the pathogenesis of cirrhosis and acute on chronic liver failure. Clinical studies describe an association of portal venous cytokine levels with the natural history of disease including portal haemodynamic status. Therefore abrogation of a portal-derived cytokine response by carbon has the potential to impact on portal hypertension.

We demonstrate a significant reduction in portal pressure in BDL and BDL+LPS rats following oral administration of micro-/mesoporous carbon. The most marked percentage reduction in portal pressure was observed in BDL+LPS treated groups. This suggests that carbon has a marked effect on endotoxin sensitivity in BDL animals in particular with regards to portal pressure responses. Carbon therapy however had no significant impact on mean arterial pressure suggesting that the haemodynamic effects are confined to the portal circulation.

Kupffer cell population and function were also observed to be modulated by carbon-treatment. Normalisation of Kupffer cell populations towards sham levels was observed in carbon-treated BDL and BDL+LPS rats. The most striking finding was a significant reduction in LPS-induced Kupffer cell ROS activity. This suggests that Kupffer cells in carbon-treated BDL rats are less primed to subsequent endotoxin challenge.

Biochemically this finding was paralleled by a significant reduction in alanine transaminase suggesting diminished ROS-induced liver injury. Absolute levels of endotoxin in portal venous plasma were not found to be significantly different between treated and non-treated BDL animals. One possible explanation for the non-significant difference in portal venous endotoxin may be the relative insensitivity of the LAL assay. The lipid A structure of endotoxin is of physiological relevance yet not detectable by the LAL assay. Therefore there is a potential for discordance between absolute values detected and physiological effects of endotoxin with this assay. The LAL assay has also been found to be particularly insensitive in the detection of endotoxin derived from commensal members of the enterobacteriacae family. That Kupffer cell endotoxin sensitivity is diminished is of more relevance physiologically with carbon therapy resulting in normalization of Kupffer cell population and function.

Intestinal permeability is improved by oral carbon as evidenced by the lactulose rhamnose assay. No morphological abnormalities of the colon were observed. (FIGS. 28 and 22.)

Cytokine analysis and effect of portal venous plasma on neutrophil burst was evaluated. A non-significant reduction in resting burst was observed in neutrophils co-incubated with plasma from carbon-treated BDL rats compared to the untreated control. Neutrophil dysfunction is known to be mediated by a humoral factor and multiple lines of evidence implicate endotoxin in pathogenesis. That increased oxidative burst was conferred by a humoral factor strongly implicates endotoxin in pathogenesis. A reduction in portal venous IL-4 and IL-10 was also observed. IL-4 has been implicated in Kupffer cell activation yet IL-10 has been implicated in dampening Kupffer cell responses within the context of the adiponectin/interleukin-10/heme oxygenase-1 pathway. It is perhaps not unsurprising if carbon is indiscriminant in cytokine binding that both pro- and anti-inflammatory cytokine responses are diminished in parallel. In fact patients manifesting with acute-on-chronic liver failure exhibit pronounced pro- and anti-inflammatory responses concurrently. There is a potential role for diminishing both of these within the portal circulation without impacting on systemic immune function. As frequently observed in biological systems, there is considerable heterogeneity in the values observed rendering the trends non-significant and therefore require further evaluation. (FIGS. 23 to 26.)

While carbon has no significant effect on *E. coli* and *S. aureus* growth kinetics in in vitro studies (FIGS. 7 and 8), a modulation in faecal bacterial populations was demonstrated in vivo following carbon therapy (FIGS. 31 to 33). A marked effect was observed with *bacteroides* populations. Carbon may therefore influence growth kinetics of non-*E. coli bacteroides* or influence the composition of the gut microflora by binding bacterial metabolites or other intercellular signaling molecules A reduction in liver smooth muscle actin expression was observed in carbon-treated animals. This suggests that the downstream effects of carbon treatment include a modulation of stellate cell function. Collagen proportionate area as a measure of fibrosis was not found to be significantly different following carbon treatment possibly because the animals were only treated for the final two weeks but the reduction in smooth muscle actin suggests that carbon treatment may result in reduced hepatic fibrosis. Taken together, this data suggests that the effects of carbon on portal haemodynamics are mediated at a sinusoidal level. Given the observed effects on Kupffer cell population and function, we postulate that micro-/mesoporous carbon therapy results in diminished translocation of bacterial products and consequent inflammatory response resulting in diminished Kupffer cell priming, ROS production and stellate cell activation and therefore fibrosis.

A significant improvement in final body weight was observed in carbon-treated compared to untreated BDL rats. No significant difference in final body weight was observed between the sham groups. Weight loss in cirrhosis is attributed to an increased catabolic state and diminished appetite particularly in the context of systemic inflammatory response. As the animals in this experiment were pair-fed and in context of the above findings, we attribute the observed improvement in weight to a diminished catabolic state.

Oral carbon therapy was associated with a significant reduction in ALT with trend towards weight reduction in carbon-treated Ob–Ob– mice. ALT was also reduced in two other models of non-alcoholic fatty liver disease, namely the half choline methionine deficient diet and methionine choline deficient diet. This reduction in injury was associated with a reduction in hepatic fat accumulation in all the 3 models and evidence of reduction in inflammatory infiltrate in these 3 models as well. This reduction in liver injury and fat accumulation was associated with a reduction in the severity of fibrosis and markers of fibrosis at the gene expression level. Taken together, these data indicate that the carbons are an effective therapy for non alcoholic fatty liver disease and reduces the severity of fibrosis.

The mechanism by which the carbons with controlled porosity achieves this is through modulation of the Kupffer cell function. Treatment with carbon in the models of non-alcoholic fatty liver disease resulted in the modulation of Kupffer cell phenotype resulted in a reduction in total Kupffer cell population and CD11b (cytokine producing) Kupffer cells. An increase was observed in CD68+ Kupffer cells both in terms of phagocytosis and ROS producing cells. A significant reduction in LPS-induced ROS production was observed. (FIGS. 34 to 38).

The deterioration in renal function induced in the BDL animals following administration of LPS was less in the carbon treated animals indicating protection of the kidneys. Lower brain water in the carbon treated BDL+LPS animals suggested potential as treatment of hepatic encephalopathy. Taken together these data suggest a possible role of the carbon as treatment for the prevention of acute on chronic liver failure.

Conclusions

TE7/TE8 activated carbons with micropores and mesopore/small macropores rapidly bind endotoxin and pro-inflammatory cytokines in vitro with no significant impact on bacterial growth kinetics. In vivo oral administration of these carbons results in a significant reduction in portal pressure and liver biochemistry associated with a reduction in Kupffer cell population and endotoxin-induced ROS activity. This was associated with a trend towards reduction in IL-4 and IL-10. No significant difference in collagen staining was observed but carbon treatment was associated with a reduction in smooth muscle actin expression. Taken together, this data suggests that oral TE7/TE8 micro/meso/small macroporous carbon modulates portal haemodynamics at a sinusoidal level by diminishing translocation of bacterial products and the downstream immune/inflammatory response.

TE7/TE8 activated carbons with micropores and mesopore/small macropores exhibit properties rendering them superior to currently available interventions. The range of porosity confers superiority to pure microporous preparations with regards to binding of bioactive molecules such as endotoxin and cytokines. The carbons do not exhibit antibiotic activity and therefore are not associated with the attendant risk of resistance or further dysbiosis. These observations suggest that oral TE7/TE8 microporous/meso/small macroporous carbon therapy has promise as a potential safe and effective interventional strategy to diminish complications of cirrhosis in particular portal hypertension.

Example 6: Effects of Oral Nanoporous Carbon Particles Therapy in Leptin Null Mice as a Model of Non-Alcoholic Steatohepatitis (NASH)

Methods

Male 10-14 week mice: 10 lep⁻/lep⁻ (Ob−/Ob−) null and 10 heterozygote male mice were randomised to receive powdered chow+/−carbon (TE7; 0.4 g/100 g body weight/day) for 4 weeks (WT−n=3; Ob− heterozygote−n=5; Ob− heterozygote+carbon−n=5; Ob−/Ob− untreated−n=5; Ob−/Ob−+carbon−n=5). Extent of liver injury was assessed by serum levels of ALT. Additionally, non-parenchymal cells were isolated and the Kupffer cell (KC) population characterised by flow cytometry as those cells expressing F4/80 (Kupffer cell marker), CD68 (Macrophage marker) and CD11b (Mediates interaction with stimulated endothelium, phagocytosis, respiratory burst). Reactive oxygen species (ROS) production by isolated KCs was also assayed. Hepatic TLR-4 expression as a surrogate of endotoxaemia was determined by immunohistochemistry.

Results

In lep⁻/lep⁻ mice, oral carbon treatment or prevention was associated with a significant reduction in ALT 889±280 IU/ml to 408±42 IU/ml (p<0.05). Total KC population was found to be increased in lep⁻/lep⁻ mice compared to heterozygote control with a significant reduction observed with carbon treatment or prevention (p<0.05). A significant reduction in KCs ROS production was also observed in carbon treated lep⁻/lep⁻ mice (p<0.05) compared to untreated lep⁻/lep⁻ controls. A significant reduction in the F4/80+,CD68−,CD11b+ cell sub-population in lep⁻/lep⁻ in the presence of carbon treatment or prevention group was also observed (p<0.05). Moreover, hepatic TLR-4 expression was reduced in carbon-treated lep⁻/lep⁻ mice compared to non-treated controls. Finally, we observed a trend towards reduction in final body weight in carbon-treated lep⁻/lep⁻ mice compared to untreated controls group (p=0.095).

Conclusions

Oral TE7/TE8 microporous/small macroporous carbon particles through modulating endotoxaemia and Kupffer cell function may be a novel therapy for non-alcoholic fatty liver disease.

Example 7: Acetaldehyde Removal

Figure 5:
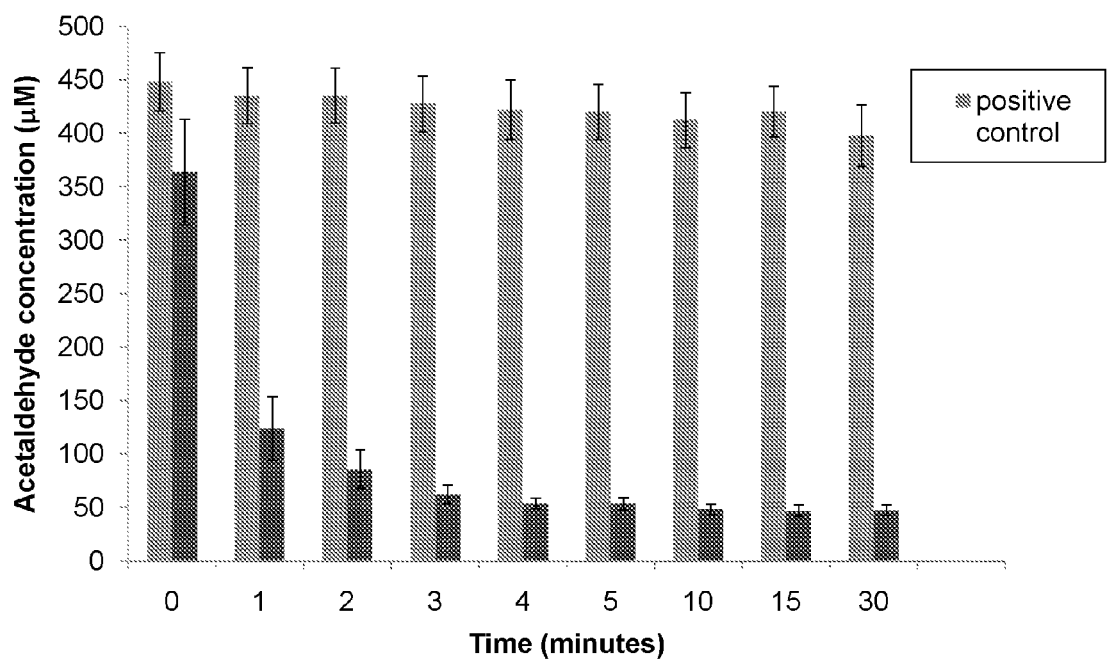
FIG. 5: A. Acetaldehyde removal over time (500 µM (22 mg/L) Ac spike, n=3, mean+/−SEM, room temp, DIE derivatizing agent, HPLC ELS detection method); B. % Acetaldehyde (AT) adsorption by test carbon over time (7.2 mM spike, 0.1 g/ml) (n=3, mean+/−SEM).
Figure 5:
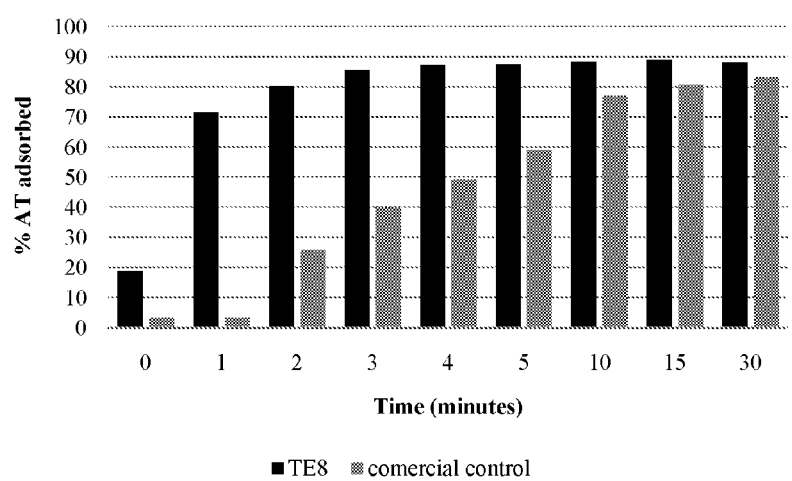

FIG. 5 shows acetaldehyde removal over time. Ac is very reactive, so a DIH derivatizing agent used according to Rideout method. This forms a stable azine fluorescent derivative detectable at 430 nm.

Example 8. Effects of Oral Nanoporous Carbon Particles Therapy in Half Methionine Choline Deficient Diet (HMCD) Fed Mice as a Model of Non-Alcoholic Steatohepatitis (NASH)

Methods

10 Male 10-14 week mice were treated with methionine choline deficient diet (MCD; 4 weeks); 10 mice were fed control diet (4 weeks). In each of the groups, animals were randomized to receive powdered chow+/−carbon (TE7; 0.4 g/100 g body weight/day) for 2 weeks. Extent of liver injury was assessed by serum levels of ALT and H and E stain on histology. Severity of fibrosis was ascertained using Sirius red staining. Gene expression for markers of fibrosis, Collagen 1 A2 and TGF beta were measured in the liver tissue.

Results

Treatment with carbon normalised the ALT levels and markedly reduced hepatic steatosis and inflammatory cell infiltration in the HMCD mice. This was associated with significant reduction in fibrosis markers. Gene expression of collagen 1A2 and TGF beta were reduced significantly in the animals treated with the carbon. (FIGS. 39-43)

Conclusions

Oral TE7/TE8 microporous/meso carbon particles through modulating endotoxaemia and KC function may be a novel therapy for non-alcoholic fatty liver disease.

Example 9. Effects of Oral Nanoporous Carbon Particles Therapy in Methionine Choline Deficient Diet (MCD) Fed Mice as a Model of Non-Alcoholic Steatohepatitis (NASH)

Methods

10 Male 10-14 week mice were treated with methionine choline deficient diet (MCD; 4 weeks); 10 mice were fed control diet (4 weeks). In each of the groups, animals were randomized to receive powdered chow+/−carbon (TE7; 0.4 g/100 g body weight/day) for 2 weeks. Extent of liver injury was assessed by serum levels of ALT and H and E stain on histology. Severity of fibrosis was ascertained using Sirius red staining.

Results

Treatment with carbon normalised the ALT levels and markedly reduced hepatic steatosis and inflammatory cell infiltration in the MCD mice. This was associated with significant reduction in fibrosis. (FIGS. 44 to 46)

Conclusions

Oral TE7/TE8 microporous/meso carbon particles through modulating endotoxaemia and KC function may be a novel therapy for non-alcoholic fatty liver disease.

The invention claimed is:

1. A method of treating liver disease or preventing progression of liver disease to cirrhosis and its complications, comprising: administering an effective amount of porous carbon particles wherein 20% to 90% of a total pore volume of the porous carbon particles is made up of pores having a mean diameter of 2 nm or less and 75% or more of the remainder of the total pore volume is made up of pores having a mean diameter of from 30 nm to 500 nm, wherein the porous carbon particles are administered orally or rectally.

2. A method according to claim 1, wherein 85% or more of the remainder of the total pore volume is made up of pores having a mean diameter of from 30 nm to 500 nm.

3. A method according to claim 2, wherein 90% or more of the remainder of the total pore volume of the porous carbon particles is made up of pores having a mean diameter of from 30 nm to 500 nm.

4. A method according to claim 1, wherein the 75% or more, 85% or more or 90% or more of the remainder of the total pore volume of the porous carbon particles is made up of pores having a mean diameter of from 50 nm to 300 nm.

5. A method according to claim 1, wherein the 75% or more, 85% or more or 90% or more of the remainder of the total pore volume of the porous carbon particles is made up of pores having a mean diameter of from 50 nm to 200 nm.

6. A method according to claim 1, wherein 35% to 60% of the total pore volume of the porous carbon particles is made up of pores having a mean diameter of 2 nm or less.

7. A method according to claim 1, wherein 45% to 55% of the total pore volume of the porous carbon particles is made up of pores having a mean diameter of 2 nm or less.

8. A method according to claim 1, wherein the total pore volume of the porous carbon particles is from 0.5 to 2.5 $cm^3 g^{-1}$.

9. A method according to claim 1, wherein the total pore volume of the porous carbon particles is from 1.0 to 2.0 $cm^3 g^{-1}$.

10. A method according to claim 1, wherein bulk density of the porous carbon particles is 0.10 $gcm^{-3}$ to 0.30 $gcm^{-3}$.

11. A method according to claim 1, wherein bulk density of the porous carbon particles is 0.15 $gcm^{-3}$ to 0.25 $gcm^{-3}$.

12. A method according to claim 1, wherein the specific surface area of the porous carbon particles is from 700 $m^2/g$ to 2000 $m^2/g$.

13. A method according to claim 1, wherein the specific surface area of the porous carbon particles is from 900 $m^2/g$ to 1400 $m^2/g$.

14. A method according to claim 1, wherein the porous carbon particles are in the form of spherical particles.

15. A method according to claim 1, wherein the porous carbon particles are administered orally in free-flowing form or in tablet form.

16. A method according to claim 1, wherein the liver disease is selected from alcoholic liver disease (ALD), non-alcoholic liver disease, non-alcoholic steatohepatitis (NASH), cirrhosis and/or complications of cirrhosis.

17. A method according to claim 16, wherein the non-alcoholic liver disease is non-alcoholic fatty liver disease (NAFLD).

18. A method according to claim 1, wherein the method treats inflammation and fibrosis in chronic liver disease selected from ALD, NAFLD and viral hepatitis.

19. A method according to claim 16, wherein the complication of cirrhosis is selected from portal hypertension, ascites, renal failure, hepatic encephalopathy and acute-on-chronic liver failure.

20. A method of modulating the gut-liver axis, comprising administering an effective amount of porous carbon particles, wherein 20% to 90% of a total pore volume of the porous carbon particles is made up of pores having a mean diameter of 2 nm or less and 75% or more of the remainder of the total pore volume is made up of pores having a mean diameter of from 30 nm to 500 nm, wherein the porous carbon particles are administered orally or rectally.

21. A method according to claim 20, wherein the modulation of the gut liver axis is by modulation of gut dysbiosis or obesity, or increased gut permeability.

22. A method of treatment of a disease or condition selected from coronary artery disease, inflammatory bowel disease, irritable bowel syndrome, pouchitis, hypertension, stroke, obesity or complications of obesity, comprising administering an effective amount of porous carbon particles, wherein 20% to 90% of a total pore volume of the porous carbon particles is made up of pores having a mean diameter of 2 nm or less and 75% or more of the remainder of the total pore volume is made up of pores having a mean diameter of from 30 nm to 500 nm, wherein the particles are administered orally or rectally.

23. A method according to claim 22, wherein the disease or condition is associated with gut dysbiosis and/or alterations in gut permeability.

24. Porous carbon particles, wherein 20% to 90% of a total pore volume is made up of pores having a mean diameter of 2 nm or less and 75% or more of the remainder of the total pore volume is made up of pores having a mean diameter of from 30 nm to 500 nm, wherein the particles are coated in order to control their release and adsorption properties.

25. Porous carbon particles according to claim 24, wherein the particles are coated with a film which allows predominant release into the large bowel.

26. A method of treating liver disease or preventing progression of liver disease to cirrhosis and its complications, the method comprising: administering an effective amount of porous carbon particles, wherein 20% to 90% of a total pore volume of the porous carbon particles is made up of pores having a mean diameter of 2 nm or less and 75% or more of the remainder of the total pore volume is made up of pores having a mean diameter of from 30 nm to 500 nm, wherein the particles are coated in order to control their release and adsorption properties.

27. A method of modulating the gut-liver axis, comprising administering an effective amount of porous carbon particles, wherein 20% to 90% of a total pore volume of the porous carbon particles is made up of pores having a mean diameter of 2 nm or less and 75% or more of the remainder of the total pore volume is made up of pores having a mean diameter of from 30 nm to 500 nm, wherein the particles are coated in order to control their release and adsorption properties.

28. A method of treatment of a disease or condition selected from coronary artery disease, inflammatory bowel disease, irritable bowel syndrome, pouchitis, hypertension, stroke, obesity or complications of obesity, the method comprising: administering an effective amount of porous carbon particles, wherein 20% to 90% of a total pore volume of the porous carbon particles is made up of pores having a mean diameter of 2 nm or less and 75% or more of the remainder of the total pore volume is made up of pores having a mean diameter of from 30 nm to 500 nm, wherein the particles are coated in order to control their release and adsorption properties.

* * * * *

UNITED STATES PATENT AND TRADEMARK OFFICE
CERTIFICATE OF CORRECTION

PATENT NO. : 9,844,568 B2  
APPLICATION NO. : 14/385332  
DATED : December 19, 2017  
INVENTOR(S) : Carol A. Howell et al.

Page 1 of 1

It is certified that error appears in the above-identified patent and that said Letters Patent is hereby corrected as shown below:

On the Title Page

Please list Item (71) the Applicant as only:  
UCL Business PLC  
London, United Kingdom Signed and Sealed this  
Thirtieth Day of January, 2018

Joseph Matal  
*Performing the Functions and Duties of the*  
*Under Secretary of Commerce for Intellectual Property and*  
*Director of the United States Patent and Trademark Office*